US008492365B2

(12) United States Patent
Nelson et al.

(10) Patent No.: US 8,492,365 B2
(45) Date of Patent: *Jul. 23, 2013

(54) 7-SUBSTITUTED TETRACYCLINE COMPOUNDS

(75) Inventors: Mark L. Nelson, Wellesley, MA (US); Roger Frechette, Reading, MA (US); Peter Viski, Brookline, MA (US); Mohamed Ismail, Bedford, MA (US); Todd Bowser, Charlton, MA (US); Beena Bhatia, Arlington, MA (US); David Messersmith, Somerville, MA (US); Laura McIntyre, Arlington, MA (US); Darrell Koza, Westerly, RI (US); Glen Rennie, South Weymouth, MA (US); Paul Sheahan, Hopkinton, MA (US); Paul Hawkins, Cambridge, MA (US); Atul Verma, Arlington, MA (US); Tadeusz Warchol, Acton, MA (US); Upul Bandarage, Newton, MA (US)

(73) Assignees: Trustees of Tufts College, Boston, MA (US); Paratek Pharmaceuticals, Inc., Boston, MA (US)

( * ) Notice: Subject to any disclaimer, the term of this patent is extended or adjusted under 35 U.S.C. 154(b) by 173 days.

This patent is subject to a terminal disclaimer.

(21) Appl. No.: 12/481,368

(22) Filed: Jun. 9, 2009

(65) Prior Publication Data
US 2009/0306022 A1 Dec. 10, 2009

Related U.S. Application Data

(63) Continuation of application No. 10/853,635, filed on May 24, 2004, now Pat. No. 7,595,309, which is a continuation of application No. 09/895,812, filed on Jun. 29, 2001, now Pat. No. 6,818,635.

(60) Provisional application No. 60/275,576, filed on Mar. 13, 2001, provisional application No. 60/216,760, filed on Jul. 7, 2000.

(51) Int. Cl.
A61K 31/65 (2006.01)
A61K 31/42 (2006.01)
A61K 31/426 (2006.01)
A61K 31/4402 (2006.01)
A61K 31/505 (2006.01)
A61K 31/5375 (2006.01)
C07C 237/26 (2006.01)
C07D 239/26 (2006.01)
C07D 295/104 (2006.01)
C07D 261/08 (2006.01)
C07D 277/42 (2006.01)

(52) U.S. Cl.
USPC ........ 514/152; 514/256; 514/357; 514/237.5; 514/379; 514/370; 544/294; 544/154; 548/248; 548/193; 552/202; 552/203; 546/285

(58) Field of Classification Search
None
See application file for complete search history.

(56) References Cited

U.S. PATENT DOCUMENTS

| | | |
|---|---|---|
| 2,980,584 A | 4/1961 | Hammer |
| 2,990,331 A | 6/1961 | Neumann et al. |
| 3,062,717 A | 11/1962 | Hammer |
| 3,148,212 A | 9/1964 | Boothe et al. |
| 3,165,531 A | 1/1965 | Nelson et al. |
| 3,219,671 A | 11/1965 | Hlavka et al. |
| 3,226,436 A * | 12/1965 | Boothe et al. .................. 552/205 |
| RE26,253 E | 8/1967 | Petisi et al. |
| 3,338,963 A | 8/1967 | Petisi et al. |
| RE26,271 E | 9/1967 | Boothe et al. |
| 3,341,585 A | 9/1967 | Bitha et al. |
| 3,345,379 A | 10/1967 | Martell et al. |
| 3,345,410 A | 10/1967 | Winterbottom et al. |
| 3,350,557 A | 10/1967 | Szymanski |
| 3,360,561 A | 12/1967 | Zambrano |
| 3,373,196 A | 3/1968 | Bitha et al. |
| 3,397,230 A | 8/1968 | Winterbottom et al. |
| 3,403,179 A | 9/1968 | Zambrano |
| 3,433,834 A | 3/1969 | Winterbottom et al. |
| 3,454,697 A | 7/1969 | Joyner et al. |
| 3,483,251 A | 12/1969 | Zambrano |
| 3,518,306 A | 6/1970 | Martell et al. |
| 3,557,280 A | 1/1971 | Weber et al. |
| 3,579,579 A | 5/1971 | Ross et al. |
| 3,609,188 A | 9/1971 | Esse et al. |
| 3,674,859 A | 7/1972 | Beutel et al. |
| 3,901,942 A | 8/1975 | Bernardi et al. |
| 3,957,980 A | 5/1976 | Noseworthy |

(Continued)

FOREIGN PATENT DOCUMENTS

| | | |
|---|---|---|
| ES | 302920 A1 | 3/1965 |
| GB | 1413347 A | 11/1975 |

(Continued)

OTHER PUBLICATIONS

U.S. Appl. No. 12/102,623, filed Apr. 2008, Berniac.*
U.S. Appl. No. 11/803,854, filed May 2007, Draper.*
U.S. Appl. No. 10/996,119, filed Nov. 2004, Levy.*
U.S. Appl. No. 10/692,764, filed Oct. 2003, Levy.*
U.S. Appl. No. 11/348,608, filed Feb. 2006, Berniac.*
Barden, Timothy C. et al., "'Glycylcyclines'. 3. 9-Aminodoxycyclinecarboxamides," J. Med. Chem., vol. 37:3205-3211 (1994).
Berge, S.M. et al. "Pharmaceutical Salts", J. Pharm. Sci. 66(1):1-19 (1977).
Canadian Office Action for Application No. 2415718, Dated Nov. 20, 2006.
Koza, D.J. "Synthesis of 7-substituted tetracycline derivatives," Org. Lett. 2(6):815-817 (2000).

(Continued)

Primary Examiner — Michael Barker
(74) Attorney, Agent, or Firm — McCarter & English, LLP

(57) ABSTRACT

The present invention pertains, at least in part, to novel 7-substituted tetracycline compounds. These tetracycline compounds can be used to treat numerous tetracycline compound-responsive states, such as bacterial infections and neoplasms, as well as other known applications for minocycline and tetracycline compounds in general, such as blocking tetracycline efflux and modulation of gene expression.

17 Claims, No Drawings

U.S. PATENT DOCUMENTS

| | | | |
|---|---|---|---|
| 3,988,468 A | 10/1976 | Rogalski et al. |
| 4,018,889 A | 4/1977 | Armstrong |
| 4,024,272 A | 5/1977 | Rogalski et al. |
| 4,126,680 A | 11/1978 | Armstrong |
| 4,849,136 A | 7/1989 | Saito et al. |
| 5,248,797 A | 9/1993 | Sum |
| 5,281,628 A | 1/1994 | Hlavka et al. |
| 5,284,963 A | 2/1994 | Sum et al. |
| 5,326,759 A | 7/1994 | Hlavka et al. |
| 5,328,902 A | 7/1994 | Sum et al. |
| 5,371,076 A | 12/1994 | Lee et al. |
| 5,380,888 A | 1/1995 | Sum et al. |
| 5,386,041 A | 1/1995 | Sum et al. |
| 5,401,729 A | 3/1995 | Sum et al. |
| 5,401,863 A | 3/1995 | Hlavka et al. |
| 5,420,272 A | 5/1995 | Sum et al. |
| 5,430,162 A | 7/1995 | Sum et al. |
| 5,442,059 A | 8/1995 | Sum et al. |
| 5,457,096 A | 10/1995 | Sum et al. |
| 5,466,684 A | 11/1995 | Sum et al. |
| 5,494,903 A | 2/1996 | Hlavka et al. |
| 5,495,018 A | 2/1996 | Sum et al. |
| 5,495,030 A | 2/1996 | Sum et al. |
| 5,495,031 A | 2/1996 | Sum et al. |
| 5,495,032 A | 2/1996 | Sum et al. |
| 5,512,553 A | 4/1996 | Sum et al. |
| 5,529,990 A | 6/1996 | Hlavka et al. |
| 5,530,117 A | 6/1996 | Hlavka et al. |
| 5,532,227 A | 7/1996 | Golub et al. |
| 5,567,692 A | 10/1996 | Sum et al. |
| 5,567,693 A | 10/1996 | Backer et al. |
| 5,639,742 A | 6/1997 | Lee et al. |
| 5,675,030 A | 10/1997 | Krishnan et al. |
| 5,789,395 A | 8/1998 | Amin et al. |
| 5,834,450 A | 11/1998 | Su |
| 5,843,925 A | 12/1998 | Backer et al. |
| 5,886,175 A | 3/1999 | Sum et al. |
| 6,506,740 B1 | 1/2003 | Ashley et al. |
| 6,617,318 B1 | 9/2003 | Nelson et al. |
| 6,624,168 B2 | 9/2003 | Nelson et al. |
| 6,638,922 B2 | 10/2003 | Ashley et al. |
| 6,642,270 B2 | 11/2003 | Nelson et al. |
| 6,683,068 B2 | 1/2004 | Nelson et al. |
| 6,818,634 B2 | 11/2004 | Nelson et al. |
| 6,818,635 B2 | 11/2004 | Nelson et al. |
| 6,833,365 B2 | 12/2004 | Levy et al. |
| 6,841,546 B2 * | 1/2005 | Draper et al. ............... 514/152 |
| 6,894,036 B2 | 5/2005 | Ashley et al. |
| 6,946,453 B2 | 9/2005 | Ashley et al. |
| 7,001,918 B2 | 2/2006 | Huss et al. |
| 7,045,507 B2 * | 5/2006 | Draper et al. ............... 514/31 |
| 7,056,902 B2 | 6/2006 | Nelson et al. |
| 7,094,806 B2 | 8/2006 | Nelson et al. |
| 2002/0128237 A1 | 9/2002 | Nelson et al. |
| 2002/0128238 A1 | 9/2002 | Nelson et al. |
| 2002/0132798 A1 | 9/2002 | Nelson et al. |
| 2004/0021801 A1 | 2/2004 | Tak et al. |
| 2004/0138183 A1 | 7/2004 | Nelson et al. |
| 2004/0152674 A1 | 8/2004 | Levy et al. |
| 2004/0176334 A1 | 9/2004 | Nelson et al. |
| 2004/0214800 A1 | 10/2004 | Levy et al. |
| 2004/0242548 A1 | 12/2004 | Draper et al. |
| 2004/0266740 A1 | 12/2004 | Huss et al. |
| 2005/0026875 A1 | 2/2005 | Nelson et al. |
| 2005/0026876 A1 | 2/2005 | Nelson et al. |
| 2005/0038002 A1 | 2/2005 | Nelson et al. |
| 2005/0070510 A1 | 3/2005 | Draper et al. |
| 2005/0119235 A1 | 6/2005 | Nelson et al. |
| 2005/0143352 A1 | 6/2005 | Nelson et al. |
| 2005/0143353 A1 | 6/2005 | Nelson et al. |
| 2005/0187198 A1 | 8/2005 | Nelson et al. |
| 2005/0215532 A1 | 9/2005 | Levy et al. |
| 2005/0250744 A1 | 11/2005 | Levy et al. |
| 2005/0288262 A1 | 12/2005 | Bandarage et al. |
| 2006/0003971 A1 | 1/2006 | Nelson |
| 2006/0084634 A1 | 4/2006 | Huss et al. |
| 2006/0089336 A1 | 4/2006 | Nelson et al. |
| 2006/0148765 A1 | 7/2006 | Nelson et al. |
| 2006/0166944 A1 | 7/2006 | Berniac et al. |
| 2006/0166945 A1 | 7/2006 | Abato et al. |
| 2006/0166946 A1 | 7/2006 | Nelson et al. |
| 2006/0194773 A1 | 8/2006 | Levy et al. |
| 2006/0205698 A1 | 9/2006 | Nelson et al. |
| 2006/0229282 A1 | 10/2006 | Nelson et al. |
| 2006/0234988 A1 | 10/2006 | Nelson et al. |
| 2006/0287283 A1 | 12/2006 | Amoo et al. |

FOREIGN PATENT DOCUMENTS

| | | |
|---|---|---|
| GB | 1469384 A | 4/1977 |
| JP | 64-029346 | 1/1989 |
| WO | WO-96/34852 A1 | 11/1996 |
| WO | WO-00/28983 A1 | 5/2000 |
| WO | WO-01/13958 A2 | 3/2001 |
| WO | WO-01/19784 A1 | 3/2001 |
| WO | WO-01/87824 A2 | 11/2001 |
| WO | WO-01/98259 A1 | 12/2001 |
| WO | WO-02/04407 A2 | 1/2002 |

OTHER PUBLICATIONS

Koza, Darrell J., et al., "Palladium Catalyzed C-N Bond Formation in the Synthesis of 7-Amio-Substituted Tetracyclines," *J. Org. Chem.*, vol. 67:5025-5027 (2002).

Martell, Michael J. Jr. et al., "The 6-Deoxytetracyclines. IX. Imidomethylation," *J. Med. Chem.*, vol. 10(3):359-363 (1967).

Nilsson, B.M. et al. "Derivatives of the muscarinic agent N-methyl-N-(1-methyl-4-pyrrolidino-2-butynyl)acetamide," *J. Med. Chem.* 31(3):577-82 (1988).

Patini, et al., Chem. Rev., 1996, 96, pp. 3147-3176, especially p. 3147.

STN RE=53108-36-4, "Tetracycline derivatives," (2007).

STN RN=53108-34-2, "Tetracycline derivatives," (2007).

Van den Bogert, C. et al. "Doxycycline in combination chemotherapy of a rat leukemia," *Cancer Res.*, 48:6686-6690 (Dec. 1, 1988).

Kirchlechner, Richard et al. "Synthesis of 6-thiaminocycline, a thiaanalog of the antibiotic minocycline" Archiv der Pharmazie, 315(6), 519-25 (1982).

Bernardi, L. et al., "Tetracycline Derivatives", Farmaco. Ed. Sc., 1975, vol. 30, pp. 1025-1030.

Li, Y.M. et al., "Capillary Zone Electrophoresis of Minocycline", *J. Pharm. Biomed. Anal.*, 1996, vol. 14, pp. 1095-1099.

Sum, P. et al., "Glycylcyclines. 1. A New Generation of Potent Antibacterial Agents through Modification of 9-Aminotetracyclines", *J. Med. Chem.*, 1994, vol. 37, pp. 184-188.

* cited by examiner

7-SUBSTITUTED TETRACYCLINE COMPOUNDS

RELATED APPLICATIONS

This application is a continuation application of U.S. Ser. No. 10/853,635, filed on May 24, 2004, which is a continuation of U.S. Ser. No. 09/895,812, now U.S. Pat. No. 6,818,635, filed on Jun. 29, 2001, which claims priority to U.S. Provisional Patent Application Ser. No. 60/275,576, filed on Mar. 13, 2001; and to U.S. Provisional Patent Application Ser. No. 60/216,760, filed on Jul. 7, 2000; the entire contents of each of these applications are hereby incorporated herein by reference.

BACKGROUND OF THE INVENTION

The development of the tetracycline antibiotics was the direct result of a systematic screening of soil specimens collected from many parts of the world for evidence of microorganisms capable of producing bacteriocidal and/or bacteriostatic compositions. The first of these novel compounds was introduced in 1948 under the name chlortetracycline. Two years later, oxytetracycline became available. The elucidation of the chemical structure of these compounds confirmed their similarity and furnished the analytical basis for the production of a third member of this group in 1952, tetracycline. A new family of tetracycline compounds, without the ring-attached methyl group present in earlier tetracyclines, was prepared in 1957 and became publicly available in 1967; and minocycline was in use by 1972.

Recently, research efforts have focused on developing new tetracycline antibiotic compositions effective under varying therapeutic conditions and routes of administration. New tetracycline analogues have also been investigated which may prove to be equal to or more effective than the originally introduced tetracycline compounds. Examples include U.S. Pat. Nos. 2,980,584; 2,990,331; 3,062,717; 3,165,531; 3,454,697; 3,557,280; 3,674,859; 3,957,980; 4,018,889; 4,024,272; and 4,126,680. These patents are representative of the range of pharmaceutically active tetracycline and tetracycline analogue compositions.

Historically, soon after their initial development and introduction, the tetracyclines were found to be highly effective pharmacologically against rickettsiae; a number of gram-positive and gram-negative bacteria; and the agents responsible for lymphogranuloma venereum, inclusion conjunctivitis, and psittacosis. Hence, tetracyclines became known as "broad spectrum" antibiotics. With the subsequent establishment of their in vitro antimicrobial activity, effectiveness in experimental infections, and pharmacological properties, the tetracyclines as a class rapidly became widely used for therapeutic purposes. However, this widespread use of tetracyclines for both major and minor illnesses and diseases led directly to the emergence of resistance to these antibiotics even among highly susceptible bacterial species both commensal and pathogenic (e.g., *pneumococci* and *Salmonella*). The rise of tetracycline-resistant organisms has resulted in a general decline in use of tetracyclines and tetracycline analogue compositions as antibiotics of choice.

SUMMARY OF THE INVENTION

The invention pertains, at least in part, to 7-substituted tetracycline compound of Formula I:

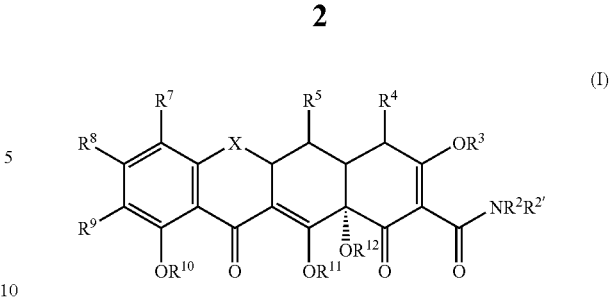

wherein:

X is $CHC(R^{13}Y'Y)$, $CR^{6'}R^{6}$, $C=CR^{6'}R^{6}$, S, $NR^{6}$, or O;

$R^{2}$, $R^{2'}$, $R^{4'}$, and $R^{4''}$ are each independently hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

$R^{4}$ is $NR^{4'}R^{4''}$, alkyl, alkenyl, alkynyl, hydroxyl, halogen, or hydrogen;

$R^{2'}$, $R^{3}$, $R^{10}$, $R^{11}$ and $R^{12}$ are each hydrogen or a pro-drug moiety;

$R^{5}$ is hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;

$R^{6}$ and $R^{6'}$ are each independently hydrogen, methylene, absent, hydroxyl, halogen, thiol, alkyl, alkenyl, alkynyl, aryl, alkoxy, alkylthio, alkylsulfinyl, alkylsulfonyl, alkylamino, or an arylalkyl;

$R^{7}$ is hydrogen, nitro, alkyl, alkenyl, alkynyl, aryl, heterocyclic, alkoxy, alkylthio, alkylsulfinyl, alkylsulfonyl, arylalkyl, amino, amido, arylalkenyl, arylalkynyl, or $-(CH_{2})_{0-3}NR^{7c}C(=W')WR^{7a}$;

$R^{9}$ is hydrogen, nitro, alkyl, alkenyl, alkynyl, aryl, alkoxy, alkylthio, alkylsulfinyl, alkylsulfonyl, arylalkyl, amino, amido, arylalkenyl, arylalkynyl, thionitroso(e.g., $-N=S$), or $-(CH_{2})_{0-3}NR^{9c}C(=Z')ZR^{9a}$;

Z is $CR^{9d}R^{9e}$, S, $NR^{9b}$ or O;

Z' is O, S, or $NR^{9f}$;

W is $CR^{7d}R^{7e}$, S, $NR^{7b}$ or O;

W' is O, $NR^{7f}$S;

$R^{7a}$, $R^{7b}$, $R^{7c}$, $R^{7d}$, $R^{7e}$, $R^{9a}$, $R^{9b}$, $R^{9c}$, $R^{9d}$, and $R^{9e}$ are each independently hydrogen, acyl, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

$R^{8}$ is hydrogen, hydroxyl, halogen, thiol, alkyl, alkenyl, alkynyl, aryl, alkoxy, alkylthio, alkylsulfinyl, alkylsulfonyl, alkylamino, or an arylalkyl;

$R^{13}$ is hydrogen, hydroxy, alkyl, alkenyl, alkynyl, alkoxy, alkylthio, alkylsulfinyl, alkylsulfonyl, alkylamino, or an arylalkyl; and Y' and Y are each independently hydrogen, halogen, hydroxyl, cyano, sulfhydryl, amino, amido, alkyl, alkenyl, alkynyl, alkoxy, alkylthio, alkylsulfinyl, alkylsulfonyl, alkylamino, or an arylalkyl, and pharmaceutically acceptable salts thereof.

The invention also pertains to 7-substituted sancycline compounds of the formula:

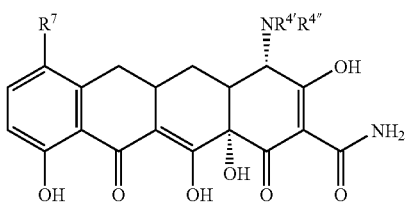

(II)

wherein:
$R^{4'}$ and $R^{4''}$ are each alkyl;
$R^7$ is a fused ring moiety of the formula

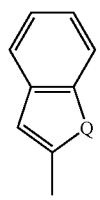

where Q is C or a heteroatom; an acylfuranyl group; a tri-, tetra- or penta-halo substituted phenyl group; an aminomethylphenyl group; an acylaminomethyl group; an alkylesterphenyl group; an acylphenyl group; an acylalkynyl group; an acylalkoxyphenyl group; a methylphenyl group; a dimethylphenyl group; a carboxyphenyl group; a carboxyalkynyl group; a thiophene group; a halothiophene group; an alkoxycarbonylphenyl group; an alkoxyphenyl group; an alkoxyphenylalkynyl group; an alkoxypyridyl group; an alkylenepyridine group; a cyclopentyl or cyclopentenyl group; a cyclohexylalkynyl group; a cyclohexenylalkynyl group; a cyclohexenylhaloalkenyl group; a hydroxycyclohexylalkynyl group; a phenylalkynyl group; a phenylalkenyl group; an aminoalkynyl group; a cyclobutylalkenyl group; a pyridylalkynyl group; a pyridylalkenyl group; a nitrophenylalkynyl group; a nitrophenylalkenyl group; a cyanoalkynyl group; an alkynyl group; a cyanoalkenyl group; a cyanophenyl group; a dialkylamidoalkenyl group; a dialkylamidophenyl group; an aminophenylethyl group; an aminophenylethynyl group; a haloethenyl group; a halophenylalkynyl group; or an alkylester-substituted pentenyl group; and pharmaceutically acceptable salts thereof.

The invention also pertains to a method for treating a tetracycline responsive state in a subject, by administering to the subject a 7-substituted tetracycline compound of the invention (e.g., of Formula I or II), such that the tetracycline responsive state is treated.

The invention also includes pharmaceutical compositions comprising an effective amount of a 7-substituted tetracycline compound of the invention and, optionally, a pharmaceutically acceptable carrier.

DETAILED DESCRIPTION OF THE INVENTION

The present invention pertains, at least in part, to novel 7-substituted tetracycline compounds. These tetracycline compounds can be used to treat numerous tetracycline compound-responsive states, such as bacterial infections and neoplasms, as well as other known applications for minocycline and tetracycline compounds in general, such as blocking tetracycline efflux and modulation of gene expression.

The term "tetracycline compound" includes many compounds with a similar ring structure to tetracycline. Examples of tetracycline compounds include: tetracycline, chlortetracycline, oxytetracycline, demeclocycline, methacycline, sancycline, doxycycline, and minocycline. Other derivatives and analogues comprising a similar four ring structure are also included. Table 1 depicts tetracycline and several known tetracycline derivatives.

TABLE I

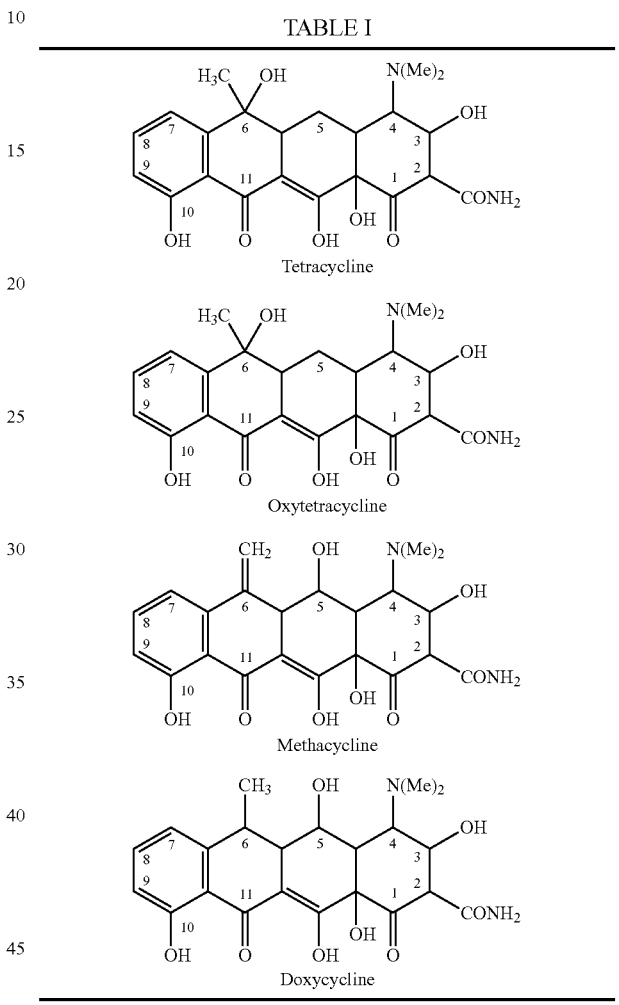

The term "7-substituted tetracycline compounds" includes tetracycline compounds with substitution at the 7 position. In one embodiment, the substitution at the 7-position enhances the ability of the tetracycline compound to perform its intended function, e.g., treat tetracycline responsive states. In an embodiment, the 7-substituted tetracycline compound is 7-substituted tetracycline (e.g., wherein $R^4$ is $NR^{4'}R^{4''}$, $R^{4'}$ and $R^{4''}$ are methyl, $R^5$ is hydrogen and X is $CR^6R^{6'}$, wherein $R^6$ is methyl and $R^{6'}$ is hydroxy); 7-substituted doxycycline (e.g., wherein $R^4$ is $NR^{4'}R^{4''}$, $R^{4'}$ and $R^{4''}$ are methyl, $R^5$ is hydroxyl and X is $CR^6R^{6'}$, wherein $R^6$ is methyl and $R^{6'}$ is hydrogen); 7-substituted tetracycline compound, wherein X is $CR^6R^{6'}$, $R^4$, $R^5$, $R^{6'}$, and $R^6$ are hydrogen; or 7-substituted sancycline (wherein $R^4$ is $NR^{4'}R^{4''}$, $R^{4'}$ and $R^{4''}$ are methyl; $R^5$ is hydrogen and X is $CR^6R^{6'}$ wherein $R^6$ and $R^{6'}$ are hydrogen atoms.

The invention pertains, at least in part, to 7-substituted tetracycline compound of Formula I:

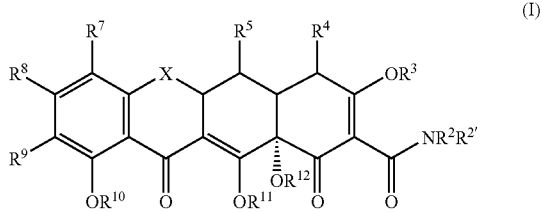

(I)

wherein:

X is CHC(R$^{13}$Y'Y), CR$^{6'}$R$^6$, C=CR$^{6'}$R$^6$, S, NR$^6$, or O;

R$^2$, R$^{2'}$, R$^{4'}$, and R$^{4''}$ are each independently hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

R$^4$ is NR$^{4'}$R$^{4''}$, alkyl, alkenyl, alkynyl, hydroxyl, halogen, or hydrogen;

R$^{2'}$, R$^3$, R$^{10}$, R$^{11}$ and R$^{12}$ are each hydrogen or a pro-drug moiety;

R$^5$ is hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;

R$^6$ and R$^{6'}$ are each independently hydrogen, methylene, absent, hydroxyl, halogen, thiol, alkyl, alkenyl, alkynyl, aryl, alkoxy, alkylthio, alkylsulfinyl, alkylsulfonyl, alkylamino, arylalkyl, or, when taken together,;

R$^7$ is nitro, alkyl, alkenyl, alkynyl, aryl, alkoxy, alkylthio, alkylsulfinyl, alkylsulfonyl, arylalkyl, amino, amido, arylalkenyl, arylalkynyl, or —(CH$_2$)$_{0-3}$NR$^{7c}$C(=W')WR$^{7a}$;

R$^9$ is hydrogen, nitro, alkyl, alkenyl, alkynyl, aryl, alkoxy, alkylthio, alkylsulfinyl, alkylsulfonyl, arylalkyl, amino, amido, arylalkenyl, arylalkynyl, thionitroso(e.g., —N=S), or —(CH$_2$)$_{0-3}$NR$^{9e}$C(=Z')ZR$^{9a}$;

Z is CR$^{9d}$R$^{9e}$S, NR$^{9b}$ or O;

Z' is O, S, or NR$^{9f}$;

W is CR$^{7d}$R$^{7e}$, S, NR$^{7b}$ or O;

W' is O, NR$^{7f}$S;

R$^{7a}$, R$^{7b}$, R$^{7c}$, R$^{7d}$, R$^{7e}$, R$^{9a}$, R$^{9b}$, R$^{9c}$, R$^{9d}$, and R$^{9e}$ are each independently hydrogen, acyl, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

R$^8$ is hydrogen, hydroxyl, halogen, thiol, alkyl, alkenyl, alkynyl, aryl, alkoxy, alkylthio, alkylsulfinyl, alkylsulfonyl, alkylamino, or an arylalkyl;

R$^{13}$ is hydrogen, hydroxy, alkyl, alkenyl, alkynyl, alkoxy, alkylthio, alkylsulfinyl, alkylsulfonyl, alkylamino, or an arylalkyl; and Y' and Y are each independently hydrogen, halogen, hydroxyl, cyano, sulfhydryl, amino, amido, alkyl, alkenyl, alkynyl, alkoxy, alkylthio, alkylsulfinyl, alkylsulfonyl, alkylamino, or an arylalkyl, and pharmaceutically acceptable salts thereof. In certain embodiment, R$^7$ is not nitro or amino.

In an embodiment, X is CR$^6$R$^{6'}$; R$^2$, R$^{2'}$, R$^6$, R$^{6'}$, R$^8$, R$^9$, R$^{10}$, R$^{11}$, and R$^{12}$ are each hydrogen; R$^4$ is NR$^{4'}$R$^{4''}$; R$^{4'}$ and R$^{4''}$ are lower alkyl (e.g., methyl); and R$^5$ is hydroxy or hydrogen.

In an embodiment, R$^7$ is aryl. Examples of aryl R$^7$ groups include substituted or unsubstituted phenyl. The phenyl R$^7$ group can be substituted with any substituent which allow the tetracycline compound to perform its intended function. Examples of substituents include, but are not limited to, alkyl, alkenyl, halogen, hydroxyl, alkoxy, alkylcarbonyloxy, alkyloxycarbonyl, arylcarbonyloxy, alkoxycarbonylamino, alkoxycarbonyloxy, aryloxycarbonyloxy, carboxylate, alkylcarbonyl, alkylaminoacarbonyl, arylalkyl aminocarbonyl, alkenylaminocarbonyl, alkylcarbonyl, arylcarbonyl, aminoalkyl, arylalkylcarbonyl, alkenylcarbonyl, alkoxycarbonyl, silyl, aminocarbonyl, alkylthiocarbonyl, phosphate, aralkyl, phosphonato, phosphinato, cyano, amino, acylamino, amido, imino, sulfhydryl, alkylthio, sulfate, arylthio, thiocarboxylate, alkylsulfinyl, sulfonato, sulfamoyl, sulfonamido, nitro, cyano, azido, heterocyclyl, alkylaryl, aryl and heteroaryl.

In a further embodiment, the phenyl R$^7$ group is substituted with substituted or unsubstituted alkyl. Examples of substituents of the alkyl include heterocycles such as, morpholine, piperdine, and pyrrolidine. In another further embodiment, the phenyl R$^7$ group is substituted with an amino group. The amino group also may be further substituted e.g., with an alkyl, alkenyl, alkynyl, carbonyl, alkoxy or aryl (e.g., substituted or unsubstituted, heteroaryl, phenyl, etc.) group. The phenyl amino substituent may be substituted with any substituent or combination of substituents which allow it to perform its intended function. Examples of such substituents include halogens (e.g., fluorine, chlorine, bromine, iodine, etc.), amino (e.g., which can in turn be substituted with an alkyl, carbonyl, alkenyl, alkynyl, or aryl moiety), and arylamino (e.g., phenylamino).

The R$^7$ phenyl group may also be substituted with alkoxy groups. Examples of alkoxy groups include, but are not limited to, methoxy, ethoxy, propoxy, butoxy, perfluoromethoxy, perchloromethoxy, methylenedioxy, etc. The phenyl group may also be substituted with an amide group such as a carbamate moiety (e.g., an alkoxycarbonylamino group).

The aryl group R$^7$ group also may be substituted or unsubstituted biaryl, e.g., naphthyl, fluorenyl, etc. The biaryl R$^7$ group can be substituted with any substituent which allow it to perform its intended function. Examples of substituents include but are not limited to, alkyl, alkenyl, halogen, hydroxyl, alkoxy, alkylcarbonyloxy, alkyloxycarbonyl, carboxy, arylcarbonyloxy, alkoxycarbonylamino, alkoxycarbonyloxy, aryloxycarbonyloxy, carboxylate, alkylcarbonyl, alkylaminoacarbonyl, arylalkyl aminocarbonyl, alkenylaminocarbonyl, alkylcarbonyl, arylcarbonyl, aminoalkyl, arylalkylcarbonyl, alkenylcarbonyl, alkoxycarbonyl, silyl, aminocarbonyl, alkylthiocarbonyl, phosphate, aralkyl, phosphonato, phosphinato, cyano, amino, acylamino, amido, imino, sulfhydryl, alkylthio, sulfate, arylthio, thiocarboxylate, alkylsulfinyl, sulfonato, sulfamoyl, sulfonamido, nitro, cyano, azido, heterocyclyl, alkylaryl, aryl and heteroaryl.

In an embodiment, the substituent is amino or formyl.

The aryl R$^7$ group also may be heteroaryl. Examples of heteroaryl R$^7$ moieties include, but are not limited to, furanyl, imidazolyl, benzothiophenyl, benzofuranyl, quinolinyl, isoquinolinyl, pyridinyl, pyrazolyl, benzodioxazolyl, benzoxazolyl, benzothiazolyl, benzoimidazolyl, methylenedioxyphenyl, indolyl, thienyl, pyrimidyl, pyrazinyl, purinyl, pyrazolyl, oxazolyl, isooxazolyl, naphthridinyl, thiazolyl, isothiazolyl, and deazapurinyl. In certain embodiments, the heteroaryl R$^7$ group is thiazolyl, thiophenyl, or furanyl.

R$^7$ also may be substituted or unsubstituted alkyl. The alkyl group can be a straight or branched chain, e.g., methyl, ethyl, i-propyl, n-propyl, n-butyl, i-butyl, t-butyl, pentyl, hexyl. etc. The alkyl group may also comprise a ring, e.g., a cycloalkyl (e.g., cyclopentyl, cyclohexyl, cyclopropyl, or cyclobutyl). The alkyl R$^7$ group may be substituted with any substituent or combination of substituents which allows the compound to perform its intended function. Examples of substituents include, but are not limited to, alkenyl, halogen, hydroxyl, alkoxy, alkylcarbonyloxy, alkyloxycarbonyl, carboxy, arylcarbonyloxy, alkoxycarbonylamino, alkoxycarbonyloxy, aryloxycarbonyloxy, carboxylate, alkylcarbonyl, alkylaminoacarbonyl, arylalkyl aminocarbonyl, alkenylaminocarbonyl, alkylcarbonyl, arylcarbonyl, aminoalkyl, arylalkylcarbonyl, alkenylcarbonyl, alkoxycarbonyl, silyl, aminocarbonyl, alkylthiocarbonyl, phosphate, aralkyl, phosphonato, phosphinato, cyano, amino, acylamino, amido, imino, sulfhydryl, alkylthio, sulfate, arylthio, thiocarboxylate, alkylsulfinyl, sulfonato, sulfamoyl, sulfonamido, nitro, cyano, azido, heterocyclyl, alkylaryl, aryl and heteroaryl.

In certain embodiments, the alkyl group is substituted with an amino, hydroxy, carboxy, carbonyl (e.g., substituted carbonyl, e.g., morpholinyl carbonyl), heterocyclic or aryl groups. Examples heterocyclic groups include, for example, furanyl, imidazolyl, benzothiophenyl, benzofuranyl, quinolinyl, isoquinolinyl, benzodioxazolyl, benzoxazolyl, benzothiazolyl, benzoimidazolyl, methylenedioxyphenyl, indolyl, thienyl, pyridinyl, pyrazolyl, pyrimidyl, pyrazinyl, purinyl, pyrazolyl, oxazolyl, isooxazolyl, naphthridinyl, thiazolyl, isothiazolyl, and deazapurinyl. In a further embodiment, the aryl group is pyridinyl.

In a further embodiment, the aralkyl $R^7$ group comprises substituted or unsubstituted phenyl. This phenyl group also may be substituted with any substituent which allows it to perform its intended function. Examples of substituents include, but are not limited to, sulfonamido, alkyl, and the other substituents listed supra for alkyl $R^7$ groups.

$R^7$ also may be substituted or unsubstituted alkenyl. Examples of substituents include those which allow the compound to perform its intended function. Examples of substituents include but are not limited to alkyl, halogen, hydroxyl, alkoxy, alkylcarbonyloxy, alkyloxycarbonyl, carboxy, arylcarbonyloxy, alkoxycarbonylamino, alkoxycarbonyloxy, aryloxycarbonyloxy, carboxylate, alkylcarbonyl, alkylaminoacarbonyl, arylalkyl aminocarbonyl, alkenylaminocarbonyl, alkylcarbonyl, arylcarbonyl, aminoalkyl, arylalkylcarbonyl, alkenylcarbonyl, alkoxycarbonyl, silyl, aminocarbonyl, alkylthiocarbonyl, phosphate, aralkyl, phosphonato, phosphinato, cyano, amino, acylamino, amido, imino, sulfhydryl, alkylthio, sulfate, arylthio, thiocarboxylate, alkylsulfinyl, sulfonato, sulfamoyl, sulfonamido, nitro, cyano, azido, heterocyclyl, alkylaryl, aryl and heteroaryl moieties.

In a further embodiment, the alkenyl $R^7$ group is substituted with an aminocarbonyl (e.g., alkylaminocarbonyl, dialkylaminocarbonyl, dimethylaminocarbonyl) or alkoxycarbonyl. The alkenyl $R^7$ group also may be substituted with one or more halogens (e.g., fluorine, chlorine, bromine, iodine, etc.), hydroxy groups, heteroaryl groups (e.g., furanyl, imidazolyl, benzothiophenyl, benzofuranyl, quinolinyl, isoquinolinyl, benzodioxazolyl, benzoxazolyl, benzothiazolyl, benzoimidazolyl, methylenedioxyphenyl, indolyl, thienyl, pyridinyl, pyrazolyl, pyrimidyl, pyrazinyl, purinyl, pyrazolyl, oxazolyl, isooxazolyl, naphthridinyl, thiazolyl, isothiazolyl, deazapurinyl, etc.). In an embodiment, the heteroaryl substituent s thiazolyl.

In a further embodiment, the alkenyl $R^7$ group is substituted with a substituted or unsubstituted phenyl. The phenyl can be substituted with any substituent which allows it to perform its intended function. Examples of substituents include those listed supra for other phenyl moieties. Other examples of substituents include, but are not limited to, halogens (e.g., fluorine, chlorine, bromine, iodine, etc.), alkoxy (e.g., methoxy, ethoxy, propoxy, perfluoromethyl, perchloromethyl, etc.), hydroxy, or alkyl (e.g., methyl, ethyl, propyl, butyl, pentyl, hexyl, etc.) groups.

Another example of $R^7$ include substituted and unsubstituted alkynyls. The alkynyl moieties can be substituted with any substituent or combination of substituents which allow the tetracycline compound of the invention to perform its intended function. Examples of the substituents include, but are not limited to alkyl, halogen, hydroxyl, alkoxy, alkylcarbonyloxy, alkyloxycarbonyl, carboxy, arylcarbonyloxy, alkoxycarbonylamino, alkoxycarbonyloxy, aryloxycarbonyloxy, carboxylate, alkylcarbonyl, alkylaminoacarbonyl, arylalkyl aminocarbonyl, alkenylaminocarbonyl, alkylcarbonyl, arylcarbonyl, aminoalkyl, arylalkylcarbonyl, alkenylcarbonyl, alkoxycarbonyl, silyl, aminocarbonyl, alkylthiocarbonyl, phosphate, aralkyl, phosphonato, phosphinato, cyano, amino, acylamino, amido, imino, sulfhydryl, alkylthio, sulfate, arylthio, thiocarboxylate, alkylsulfinyl, sulfonato, sulfamoyl, sulfonamido, nitro, cyano, azido, heterocyclyl, alkylaryl, aryl and heteroaryl moieties.

In an embodiment, the alkynyl $R^7$ moiety is substituted with an aryl, e.g., substituted or unsubstituted heteroaryl, phenyl, etc. This aryl moiety may be substituted with any substituent or combinations of substituents listed supra for the alkynyl $R^7$ moiety. Examples of advantageous substituents include, but are not limited to, carbonylamino (e.g., alkylcarbonylamino, dialkylcarbonylamino, arylcarbonylamino, etc.) and sulphonamido groups.

In another embodiment, the alkynyl $R^7$ group is substituted with a tetracycline moiety. The term "tetracycline moiety" includes a four ring tetracycline ring system as described above. This may be connected to the alkynyl $R^7$ group through a linker of 1-20 atoms. The linker may be attached to the tetracycline moiety at any position on that ring system which is convenient or allows the compound to perform its intended function. In a certain embodiment, the tetracycline moiety is attached to the linker at its 7 position.

Other examples of $R^7$ moieties include substituted and unsubstituted alkylcarbonyl amino, sulfonamido, imino and carbonyl moieties. The carbonyl moieties may be substituted with a substituted or unsubstituted alkyl group. Examples of possible substituents of the alkyl group include, but are not limited to, aryl moieties such as phenyl and heteroaryls (e.g., pyridinyl, etc.). Examples of substituents of the imino group include, but are not limited to, hydroxy and alkoxy groups.

In another embodiment, $R^7$ is $NR^{7c}(C=W')WR^{7a}$. Examples of tetracycline compounds of the invention include compounds wherein $R^{7c}$ is hydrogen, W' is oxygen and W is oxygen. In certain embodiments, $R^{7a}$ is substituted or unsubstituted phenyl. Examples of substituents include, but are not limited to, alkyl, halogen, hydroxyl, alkoxy, alkylcarbonyloxy, alkyloxycarbonyl, carboxy, alkylcarbonylamino, arylcarbonyloxy, alkoxycarbonylamino, alkoxycarbonyloxy, aryloxycarbonyloxy, carboxylate, alkylcarbonyl, alkylaminoacarbonyl, arylalkyl aminocarbonyl, alkenylaminocarbonyl, alkylcarbonyl, arylcarbonyl, aminoalkyl, arylalkylcarbonyl, alkenylcarbonyl, alkoxycarbonyl, silyl, aminocarbonyl, alkylthiocarbonyl, phosphate, aralkyl, phosphonato, phosphinato, cyano, amino, acylamino, amido, imino, sulfhydryl, alkylthio, sulfate, arylthio, thiocarboxylate, alkylsulfinyl, sulfonato, sulfamoyl, sulfonamido, nitro, cyano, azido, heterocyclyl, alkylaryl, aryl and heteroaryl. In a further embodiment, $R^{7a}$ is substituted or unsubstituted alkyl.

The invention also pertains to 7-substituted sancycline compounds of the formula:

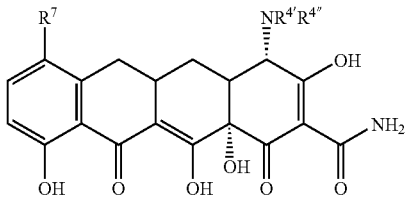

wherein:

$R^{4'}$ and $R^{4''}$ are each alkyl; and $R^7$ is a fused ring moiety of the formula

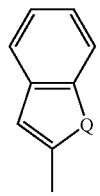

where Q is C or a heteroatom; an acylfuranyl group; a tri-, tetra- or penta-halo substituted phenyl group; an aminomethylphenyl group; an acylaminomethyl group; an alkylesterphenyl group; an acylphenyl group; an acylalkynyl group; an acylalkoxyphenyl group; a methylphenyl group; a dimethylphenyl group; a carboxyphenyl group; a carboxyalkynyl group; a thiophene group; a halothiophene group; an alkoxycarbonylphenyl group; an alkoxyphenyl group; an alkoxyphenylalkynyl group; an alkoxypyridyl group; an alkylenepyridine group; a cyclopentyl or cyclopentenyl group; a cyclohexylalkynyl group; a cyclohexenylalkynyl group; a cyclohexenylhaloalkenyl group; a hydroxycyclohexylalkynyl group; a phenylalkynyl group; a phenylalkenyl group; an aminoalkynyl group; a cyclobutylalkenyl group; a pyridylalkynyl group; a pyridylalkenyl group; a nitrophenylalkynyl group; a nitrophenylalkenyl group; a cyanoalkynyl group; an alkynyl group; a cyanoalkenyl group; a cyanophenyl group; a dialkylamidoalkenyl group; a dialkylamidophenyl group; an aminophenylethyl group; an aminophenylethynyl group; a haloethenyl group; a halophenylalkynyl group; or an alkylester-substituted pentenyl group; and pharmaceutically acceptable salts thereof.

The term "7-substituted sancycline compounds" includes sancycline compounds with a substituent at the 7 position, as described in formula I. In a further embodiment, both $R^{4'}$ and $R^{4''}$ are each methyl.

In a further embodiment, $R^7$ is a fused ring moiety of the formula

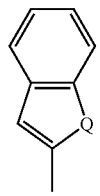

where Q is C or a heteroatom. Examples of sancycline compounds with this $R^7$ substituent include 7-(2-benzofuran)sancycline.

In yet another embodiment, $R^7$ is an acylfuranyl group. Examples of sancycline compounds with this $R^7$ substituent include 7-(3-formylfuranyl)sancycline.

In yet another embodiment, $R^7$ is a tri-, tetra- or penta-halo substituted phenyl group. Examples of sancycline compounds with this $R^7$ substituent include 7-(2,3,4,5,6-pentafluorophenyl)sancycline.

In yet another embodiment, $R^7$ is an aminomethylphenyl group. Examples of sancycline compounds with this $R^7$ substituent include 7-(4-aminomethylphenyl)sancycline.

In yet another embodiment, $R^7$ is an acylaminomethyl group. Examples of sancycline compounds with this $R^7$ substituent include 7-(4-formylaminomethylphenyl)sancycline.

In yet another embodiment, $R^7$ is an alkylesterphenyl group. Examples of sancycline compounds with this $R^7$ substituent include 7-(4-carboxyphenyl methylester)sancycline and 7-(2-carboxyphenylethylester)sancycline.

In yet another embodiment, $R^7$ is an alkylphenyl group. Examples of sancycline compounds with this $R^7$ substituent include 7-(4-tolyl)sancycline.

In yet another embodiment, $R^7$ is an acylphenyl group. Examples of sancycline compounds with this $R^7$ substituent include 7-(3-formylphenyl)sancycline, 7-(4-formylphenyl)sancycline, 7-(3-acetylphenyl)sancycline, 7-(2-acetylphenyl)sancycline, 7-(3-acetylphenyl)sancycline, and 7-(4-acetylphenyl)sancycline.

In yet another embodiment, $R^7$ is an acylalkoxyphenyl group. Examples of sancycline compounds with this $R^7$ substituent include 7-(3-formyl-6-methoxyphenyl)sancycline.

In yet another embodiment, $R^7$ is a methylphenyl group. Examples of sancycline compounds with this $R^7$ substituent include 7-(4-methylphenyl)sancycline.

In yet another embodiment, $R^7$ is a dimethylphenyl group. Examples of sancycline compounds with this $R^7$ substituent include 7-(3,5-dimethylphenyl)sancycline.

In yet another embodiment, $R^7$ is a carboxyphenyl group. Examples of sancycline compounds with this $R^7$ substituent include 7-(3-carboxyphenyl)sancycline.

In yet another embodiment, $R^7$ is a carboxyalkynyl group. Examples of sancycline compounds with this $R^7$ substituent include 7-(carboxyethynyl)sancycline.

In yet another embodiment, $R^7$ is a thiophene group. Examples of sancycline compounds with this $R^7$ substituent include 7-(3-thiophene)sancycline, 7-(3-methyl-2-thiophene)sancycline, and 7-(3-methyl-5-thiophene)sancycline.

In yet another embodiment, $R^7$ is a halothiophene group. Examples of sancycline compounds with this $R^7$ substituent include 7-(3-chloro-2-thiophene)sancycline and 7-(4-chloro-2-thiophene)sancycline.

In yet another embodiment, $R^7$ is an alkoxycarbonylphenyl group. Examples of sancycline compounds with this $R^7$ substituent include 7-(2-ethoxycarbonylphenyl)sancycline.

In yet another embodiment, $R^7$ is an alkoxyphenyl group. Examples of sancycline compounds with this $R^7$ substituent include 7-(2-ethoxyphenyl)sancycline, 7-(3-ethoxyphenyl)sancycline, 7-(4-methoxyphenyl)sancycline, and 7-(2,5-dimethoxyphenyl)sancycline.

In yet another embodiment, $R^7$ is an alkoxyphenylalkynyl group. Examples of sancycline compounds with this $R^7$ substituent include 7-(4-methoxyphenylethynyl)sancycline.

In yet another embodiment, $R^7$ is an alkoxypyridyl group. Examples of sancycline compounds with this $R^7$ substituent include 7-(4-methoxy-5-pyridyl)sancycline.

In yet another embodiment, R⁷ is a cyclopentyl or cyclopentenyl group. Examples of sancycline compounds with this R⁷ substituent include 7-(cyclopentenyl)sancycline.

In yet another embodiment, R⁷ is a cyclohexylalkynyl group. Examples of sancycline compounds with this R⁷ substituent include 7-(cyclohexylethynyl)sancycline.

In yet another embodiment, R⁷ is a cyclohexenylalkynyl group. Examples of sancycline compounds with this R⁷ substituent include 7-(1-ethynyl-1-cyclohexyl)sancycline.

In yet another embodiment, R⁷ is a cyclohexenylhaloalkenyl group. Examples of sancycline compounds with this R⁷ substituent include 7-(1-chlorovinyl-1-cyclohexyl)sancycline.

In yet another embodiment, R⁷ is a hydroxycyclohexylalkynyl group. Examples of sancycline compounds with this R⁷ substituent include 7-(1-ethynyl-1-hydroxycyclohexyl)sancycline.

In yet another embodiment, R⁷ is a phenylalkynyl group. Examples of sancycline compounds with this R⁷ substituent include 7-(phenylethynyl)sancycline, 7-(tolylethynyl)sancycline, and 7-(4-methoxyphenylethynyl)sancycline.

In yet another embodiment, R⁷ is a phenylalkenyl group. Examples of sancycline compounds with this R⁷ substituent include 7-(2-vinylpyridyl)sancycline and 7-(vinylphenyl)sancycline.

In yet another embodiment, R⁷ is an aminoalkynyl group. Examples of sancycline compounds with this R⁷ substituent include 7-(dimethylaminoethynyl)sancycline.

In yet another embodiment, R⁷ is a cyclobutylalkenyl group. Examples of sancycline compounds with this R⁷ substituent include 7-(cyclobutylmethenyl)sancycline.

In yet another embodiment, R⁷ is a pyridylalkynyl group. Examples of sancycline compounds with this R⁷ substituent include 7-(2-pyridylethynyl)sancycline and 7-(3-pyridylethynyl)sancycline.

In yet another embodiment, R⁷ is a pyridylalkenyl group. Examples of sancycline compounds with this R⁷ substituent include 7-(4-pyridylethenyl)sancycline.

In yet another embodiment, R⁷ is a nitrophenylalkynyl group. Examples of sancycline compounds with this R⁷ substituent include 7-(4-nitrophenylethynyl)sancycline.

In yet another embodiment, R⁷ is a nitrophenylalkenyl group. Examples of sancycline compounds with this R⁷ substituent include 7-(4-nitrostyryl)sancycline.

In yet another embodiment, R⁷ is an alkynyl group. Examples of sancycline compounds with this R⁷ substituent include 7-(ethynyl)sancycline.

In yet another embodiment, R⁷ is a cyanoalkynyl group. Examples of sancycline compounds with this R⁷ substituent include 7-(cyano-1-pentynyl)sancycline.

In yet another embodiment, R⁷ is a cyanoalkenyl group. Examples of sancycline compounds with this R⁷ substituent include and 7-(cyanohexenyl)sancycline.

In yet another embodiment, R⁷ is a cyanophenyl group. Examples of sancycline compounds with this R⁷ substituent include 7-(3-cyanophenyl)sancycline and 7-(4-cyanophenyl)sancycline.

In yet another embodiment, R⁷ is a hydroxylphenylethynyl group. Examples of sancycline compounds with this R⁷ substituent include 7-(3-hydroxylphenylethynyl)sancycline.

In yet another embodiment, R⁷ is a dialkylamidoalkenyl group. Examples of sancycline compounds with this R⁷ substituent include 7-(N,N-dimethylacrylamide)sancycline and 7-(dimethylamidoethenyl)sancycline.

In yet another embodiment, R⁷ is a dialkylamidophenyl group. Examples of sancycline compounds with this R⁷ substituent include 7-(3-dimethylamidophenyl)sancycline.

In yet another embodiment, R⁷ is an aminophenylethyl group. Examples of sancycline compounds with this R⁷ substituent include 7-(4-aminophenylethyl)sancycline.

In yet another embodiment, R⁷ is an aminophenylethynyl group. Examples of sancycline compounds with this R⁷ substituent include 7-(4-aminophenylethynyl)sancycline.

In yet another embodiment, R⁷ is a haloethenyl group. Examples of sancycline compounds with this R⁷ substituent include 7-(2-chloroethenyl)sancycline.

In yet another embodiment, R⁷ is a halophenylalkynyl group. Examples of sancycline compounds with this R⁷ substituent include 7-(2-fluorophenylethenyl)sancycline.

In yet another embodiment, R⁷ is an alkylester-substituted pentenyl group. Examples of sancycline compounds with this R⁷ substituent include 7-(1-iodo-1,3-dicarboethoxy-1,3-butadiene)sancycline.

In yet another embodiment, R⁷ is an aminophenylalkynyl group. Examples of sancycline compounds with this R⁷ substituent include 7-(4-aminophenylvinyl)sancycline.

The invention also pertains to the tetracycline compounds shown below:

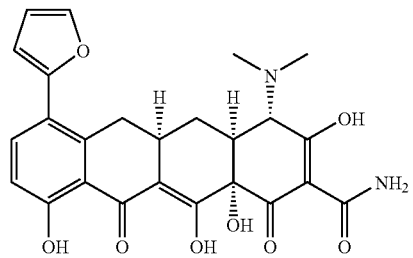
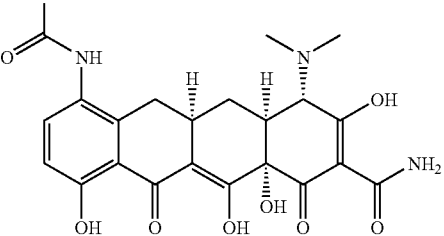
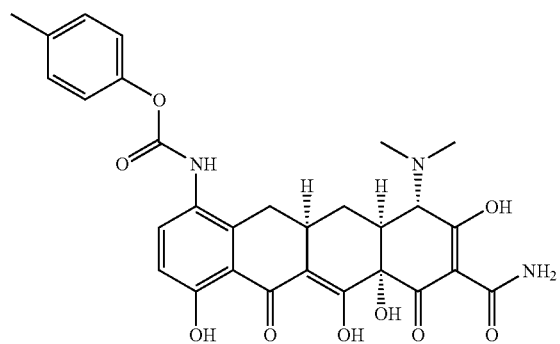
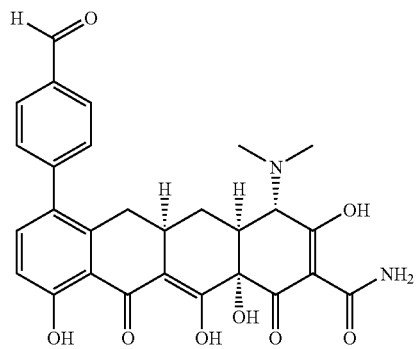
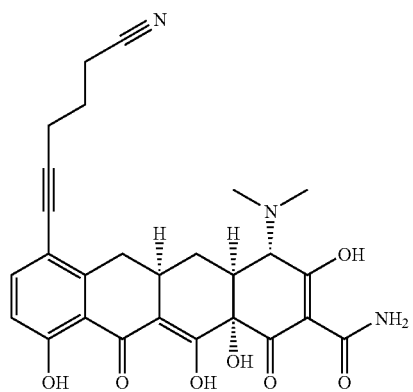
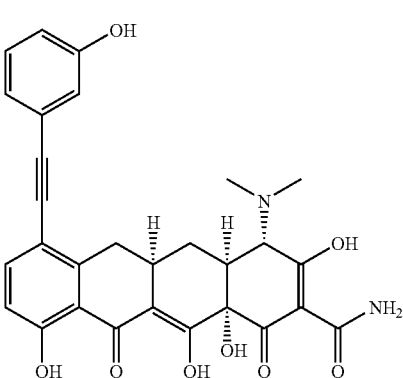
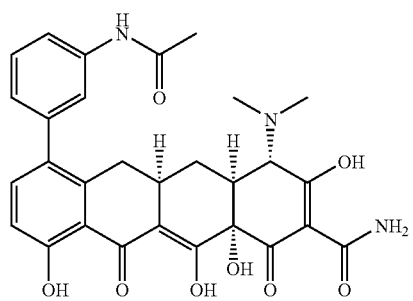
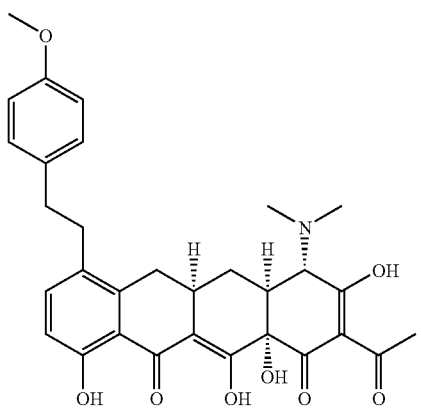

-continued
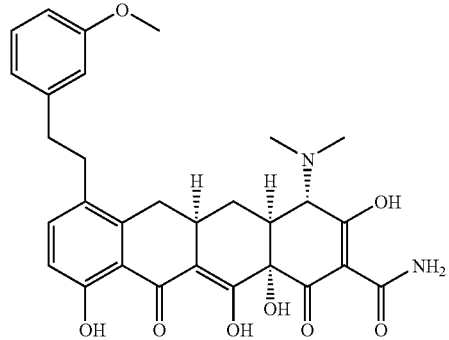
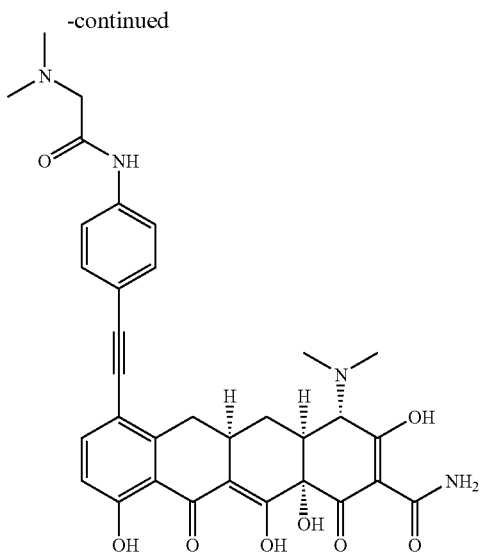
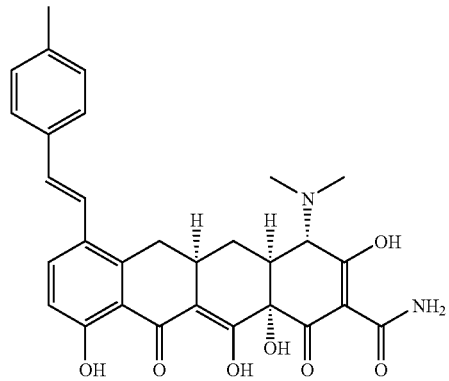
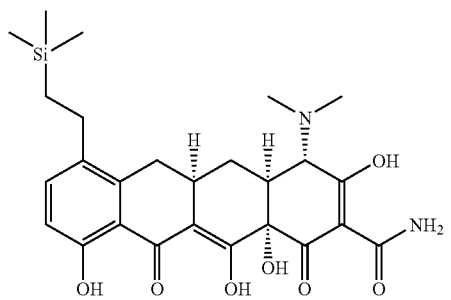
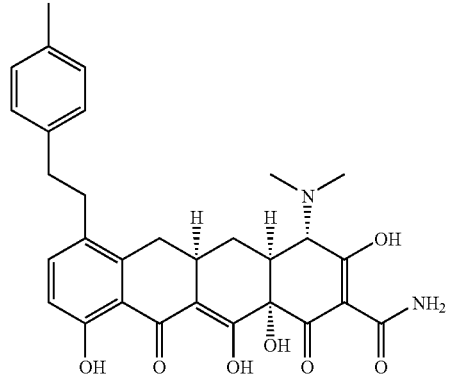
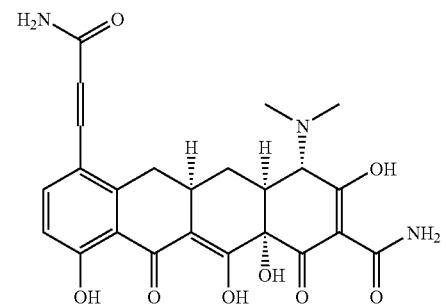
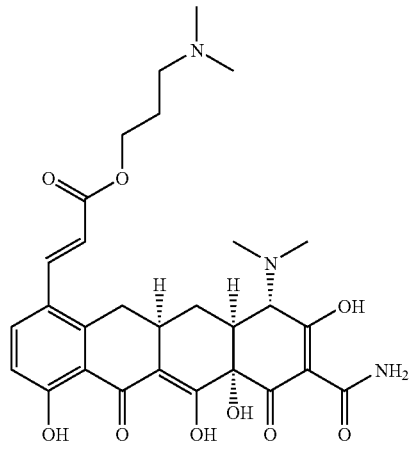
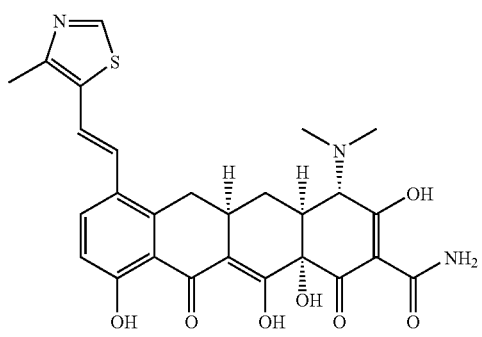

-continued
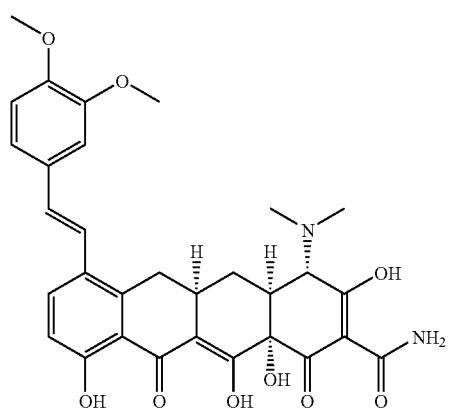
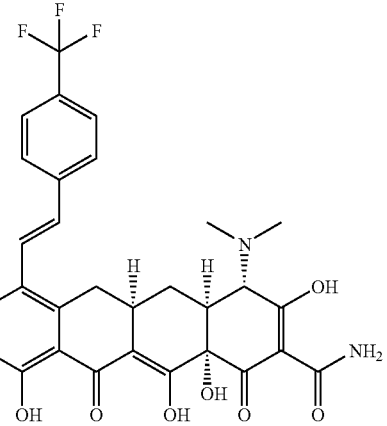
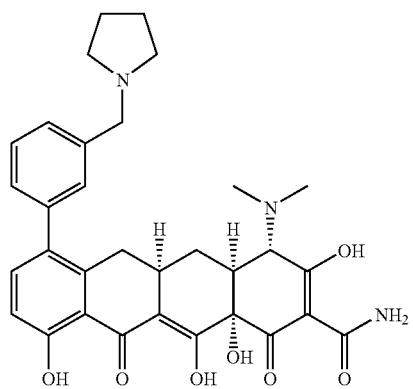
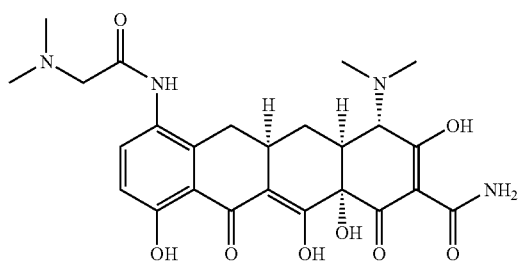
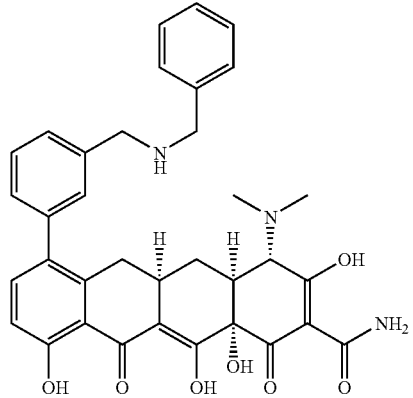
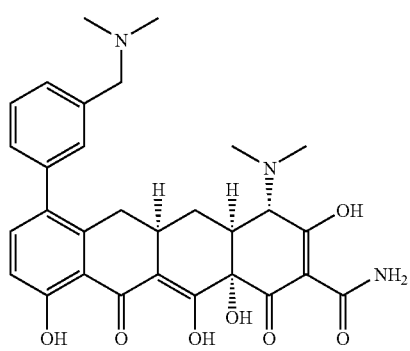
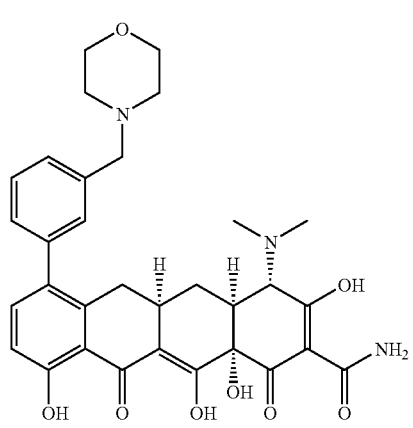
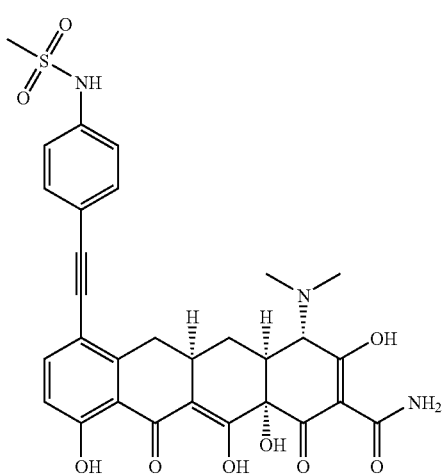

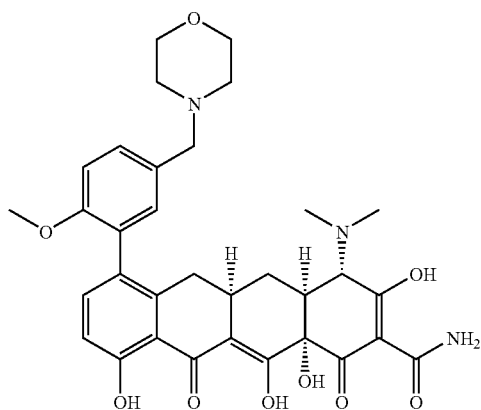
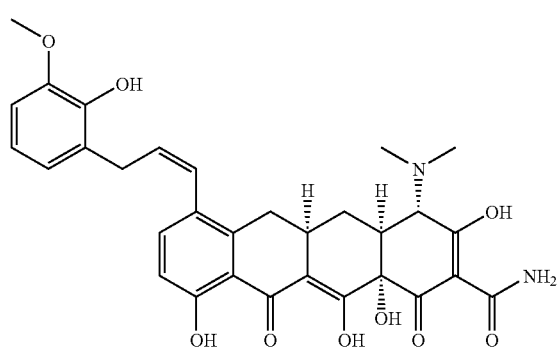
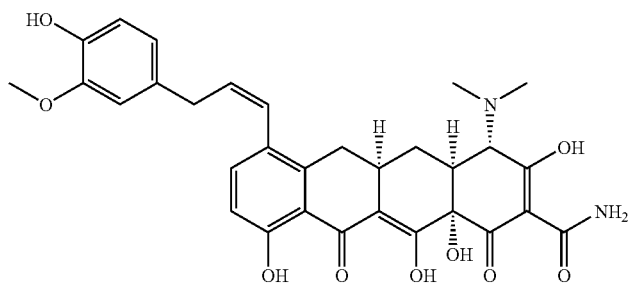
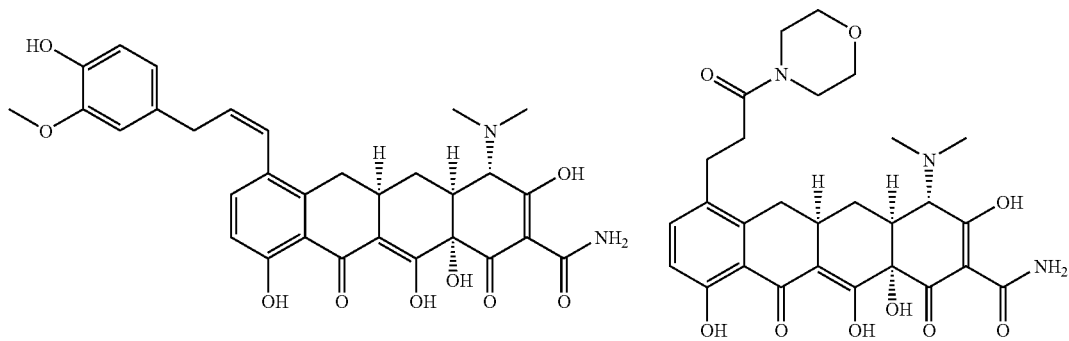
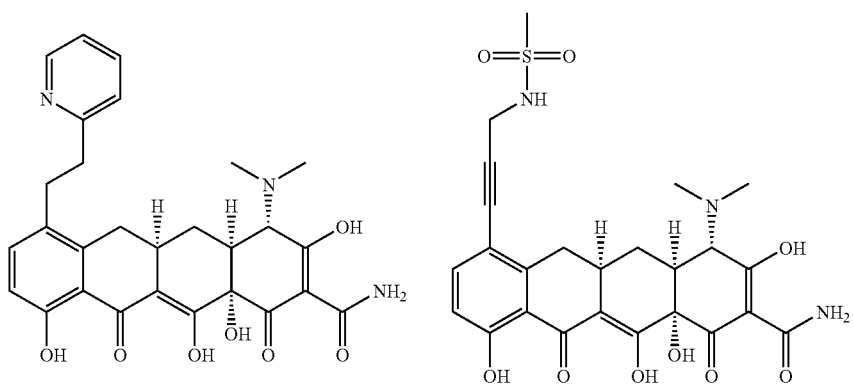

-continued
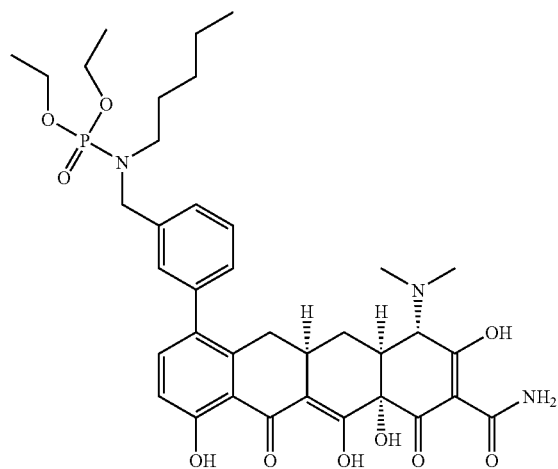
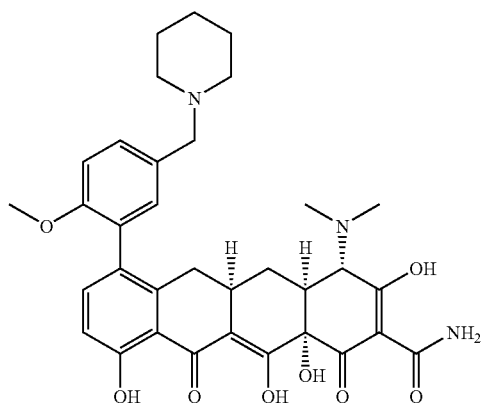
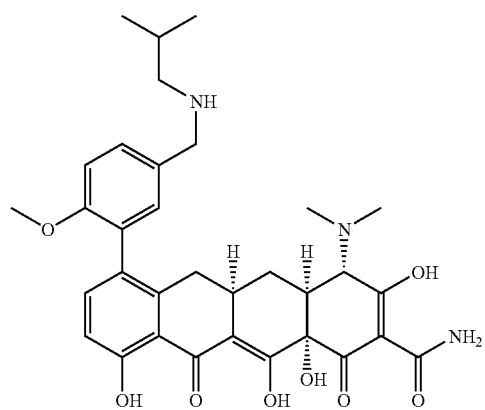
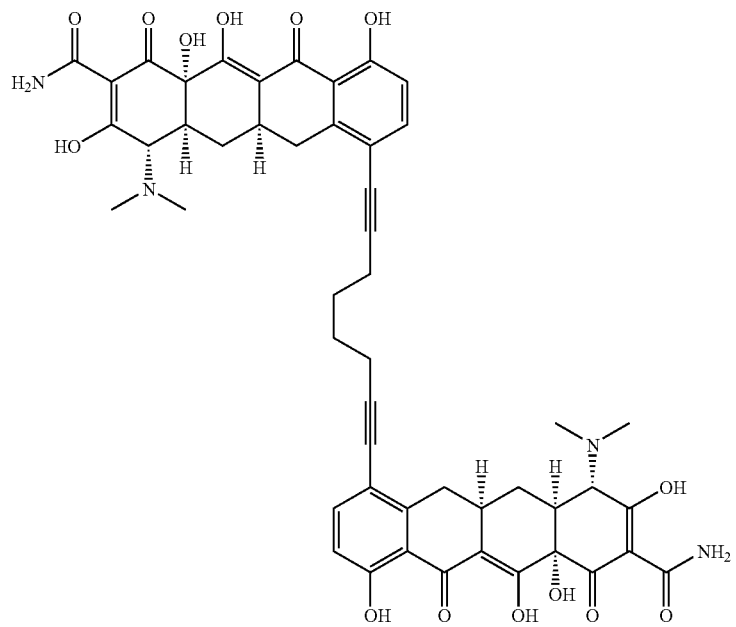

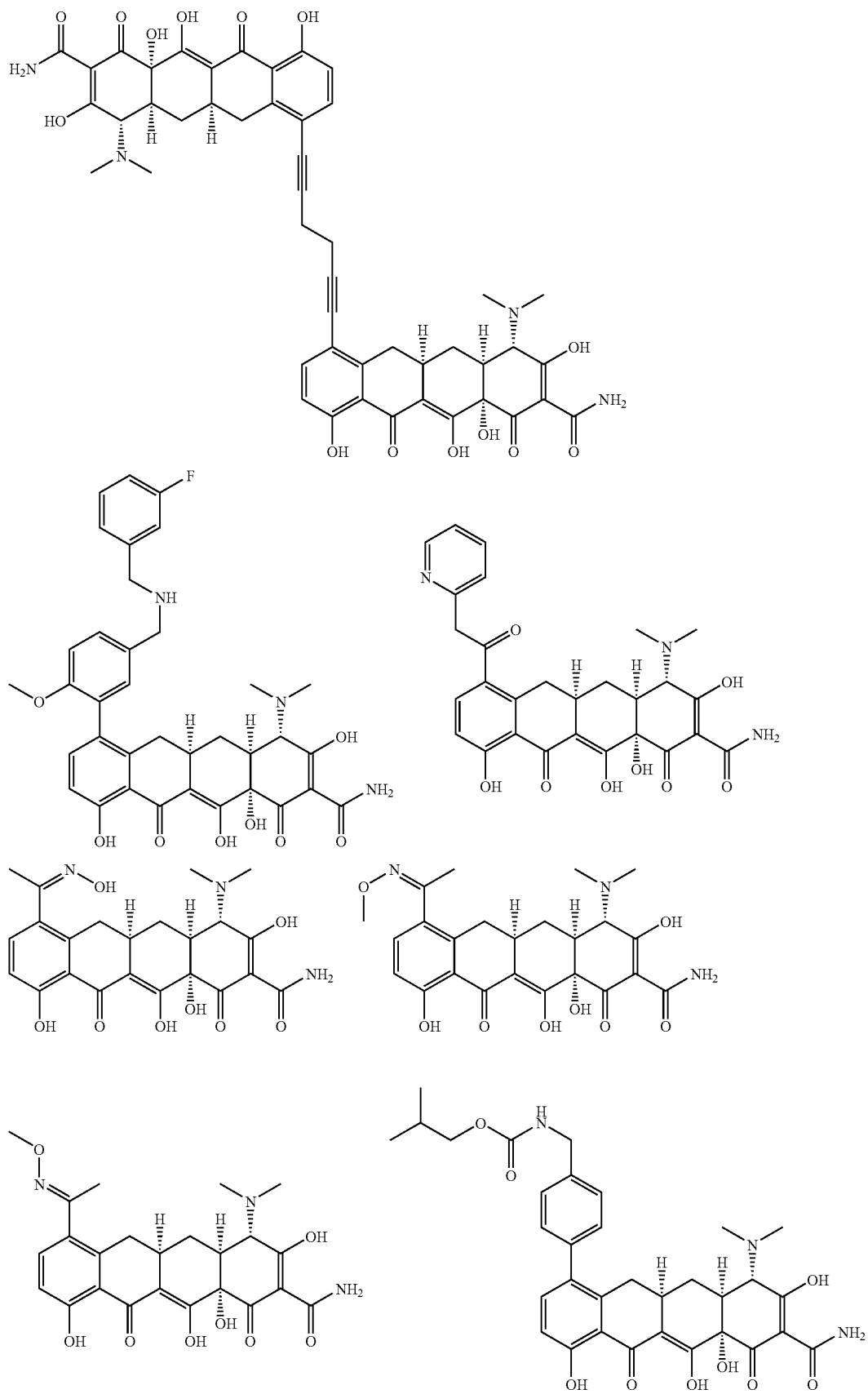

25
26
-continued
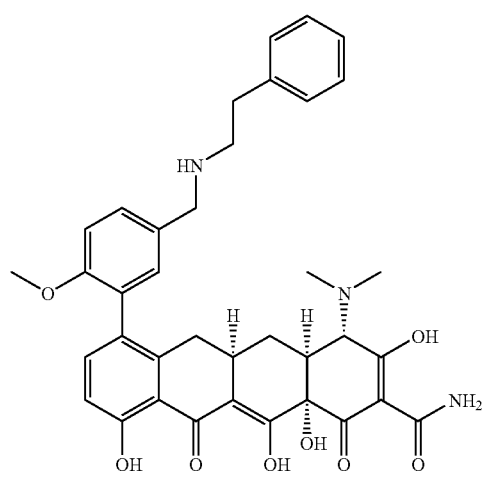
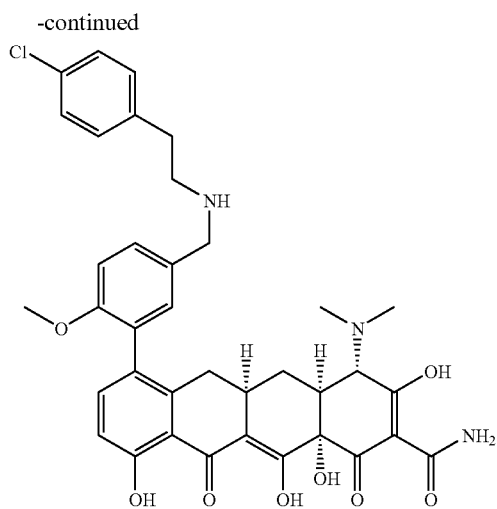
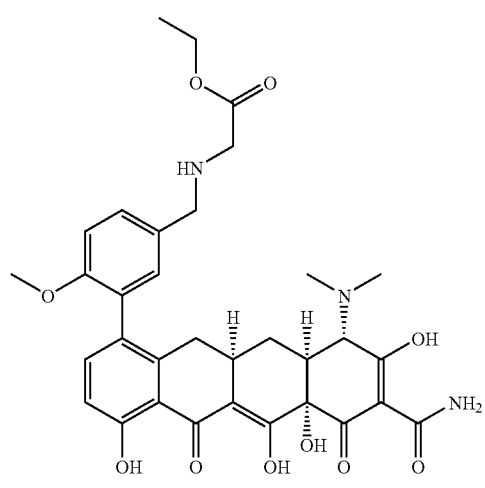
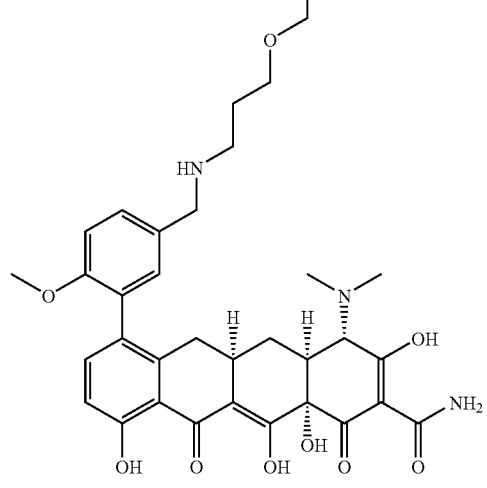
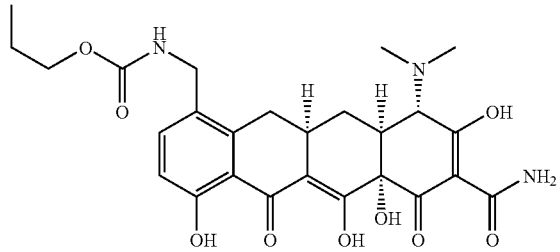
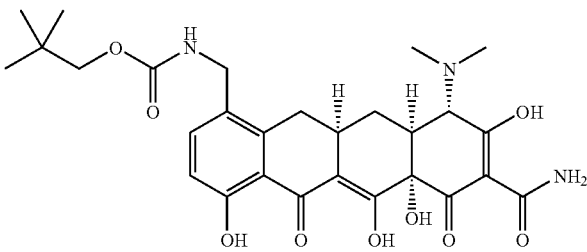
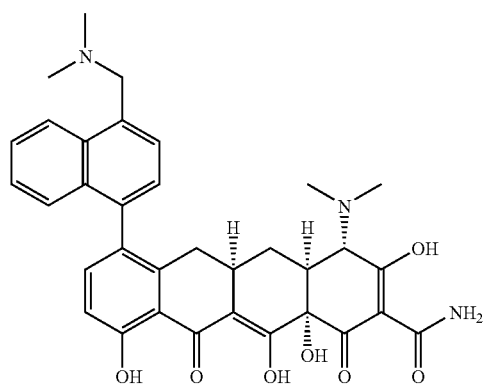
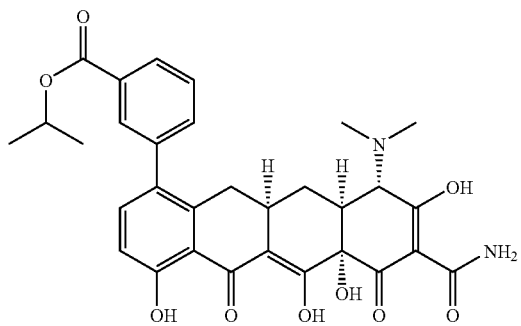

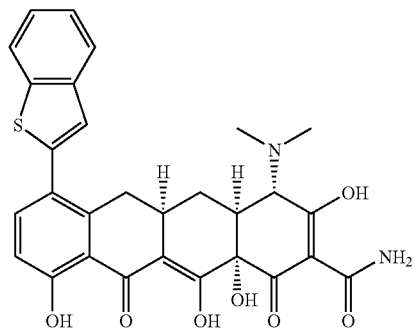
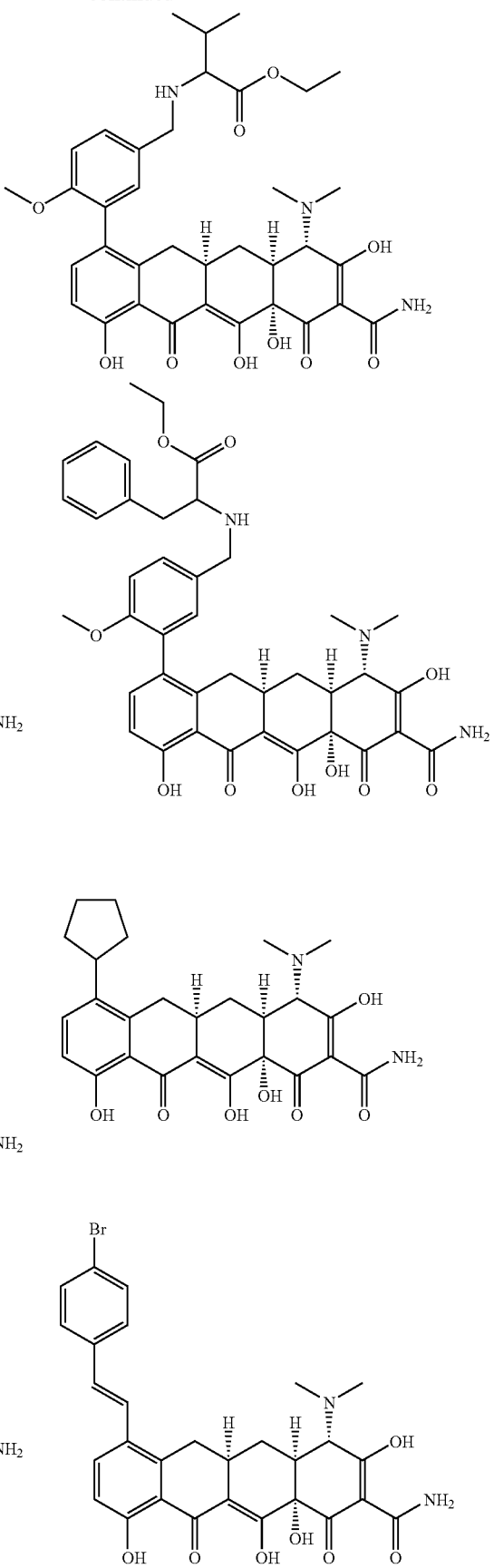

-continued
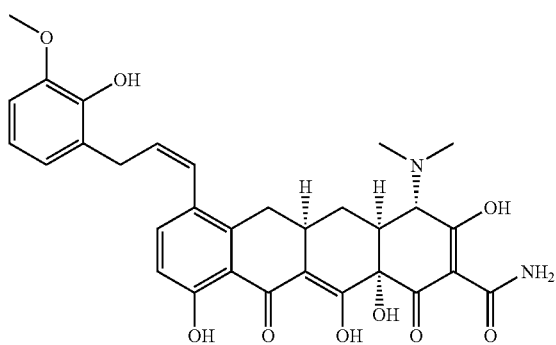
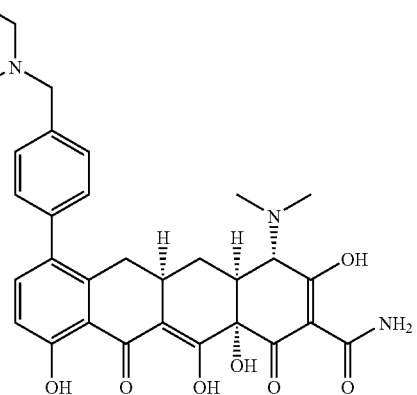
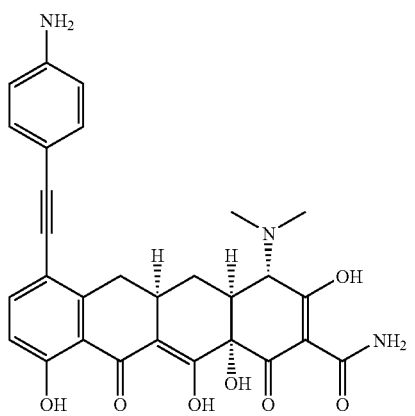
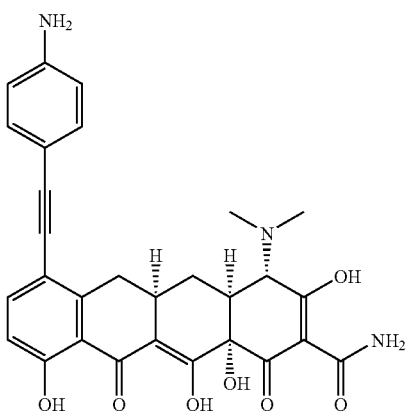
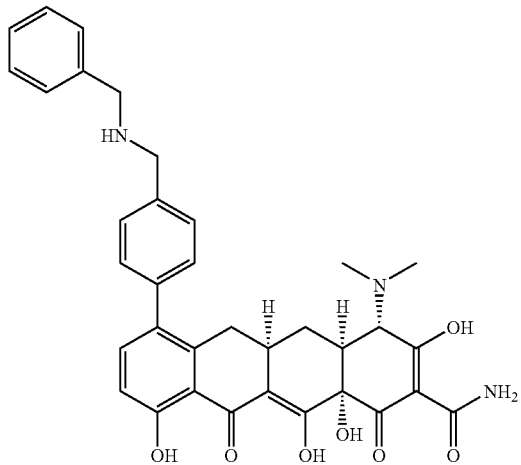
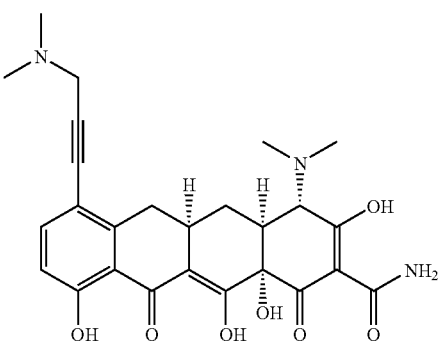
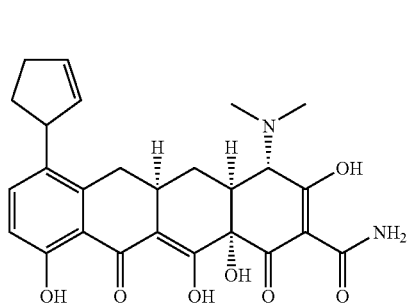
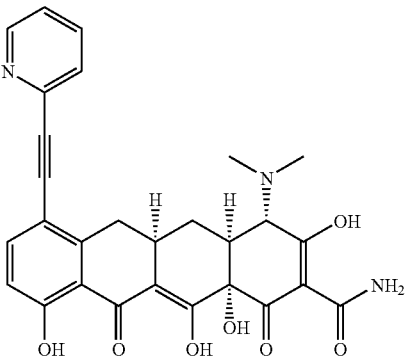

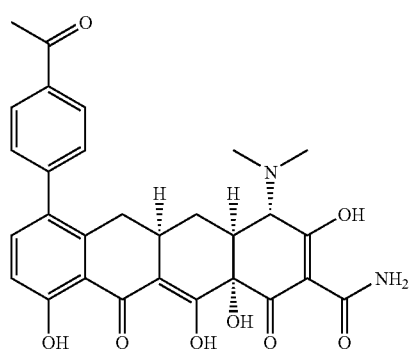
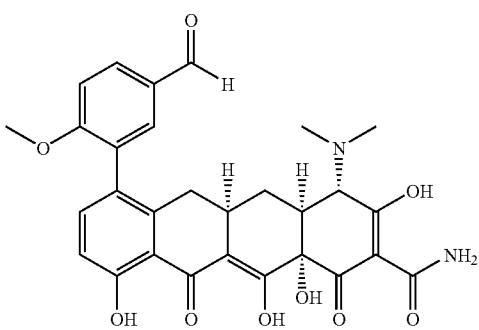

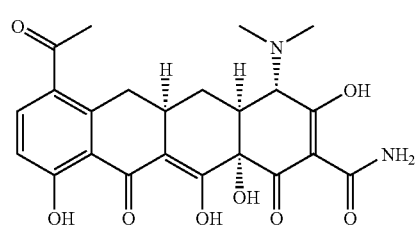
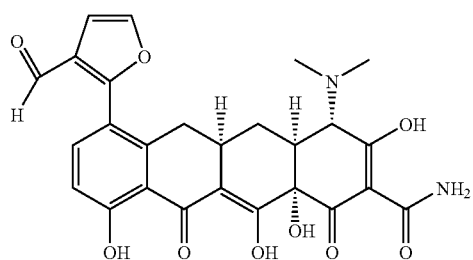

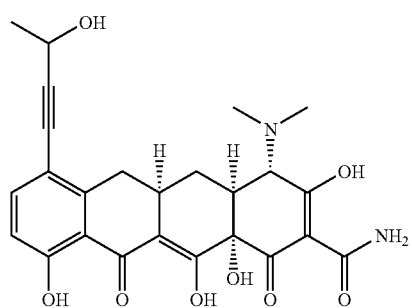
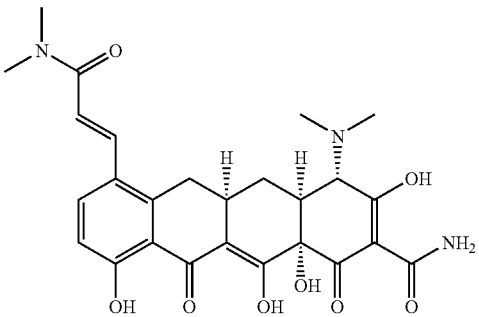

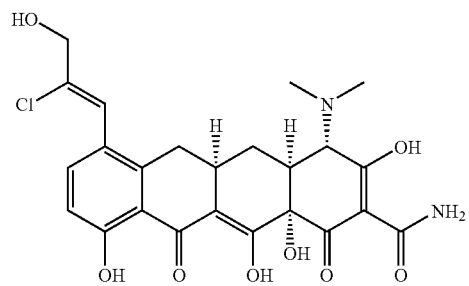

Also included are salts, esters and prodrugs of the compounds shown above.

In a further embodiment, the invention pertains to 7-substituted tetracycline compounds of the formulae:

The invention also pertains to each of the 7-substituted tetracycline compounds shown in Table 2, as well as their pharmaceutically acceptable salts, esters, and prodrugs.

The tetracycline compounds of this invention can be synthesized using the methods described in Schemes 1-8.

Certain 7-substituted tetracycline compounds can be synthesized by the method shown in Scheme 1. Although in each scheme sancycline is used as the tetracycline compound, one of skill in the art will appreciate that the methodology can also be applied to other tetracycline compounds such as tetracycline and doxycycline.

SCHEME 1

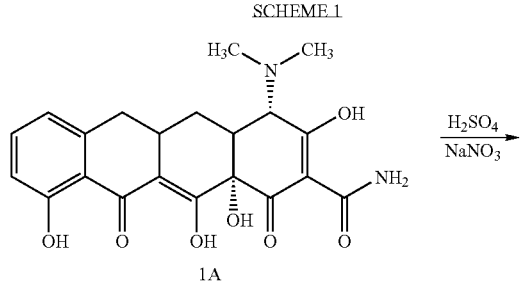
1A

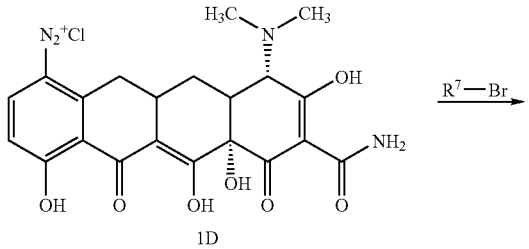
1D

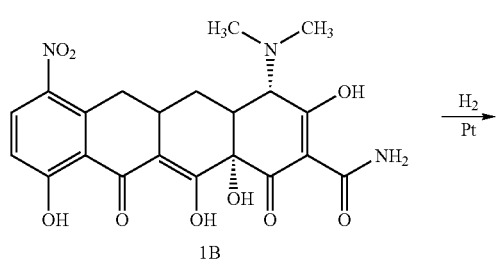
1B

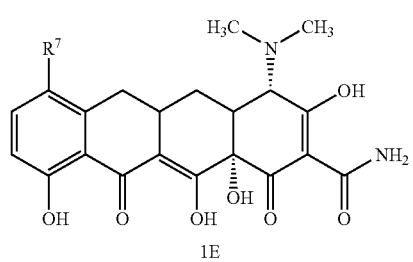
1E

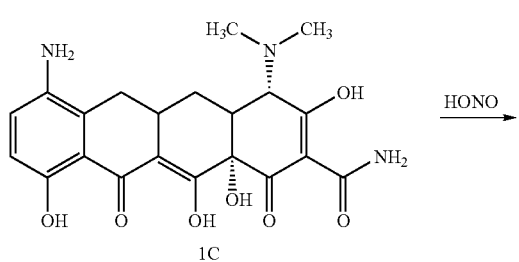
1C

Generally, 7-substituted tetracycline compounds can be synthesized as shown in Scheme 1 for sancycline. Sancycline (1A) is treated with sulfuric acid and sodium nitrate. The resulting product is 7-nitro (1B)sancycline (in a mixture with the 9-position isomers). The nitro sancycline compound is then treated with hydrogen gas and a platinum catalyst to yield the 7-amino sancycline compound, 1C. To synthesize 7 derivatives, the 7-amino sancycline compound is treated with HONO, to yield the diazonium salt (1D). The salt can subsequently be treated with numerous compounds possessing an alkene or n bond functional group such as alkenes, aryls, and alkynyls (e.g., R⁷Br) yielding the 7-substituted sancycline compound (1E).

SCHEME 2

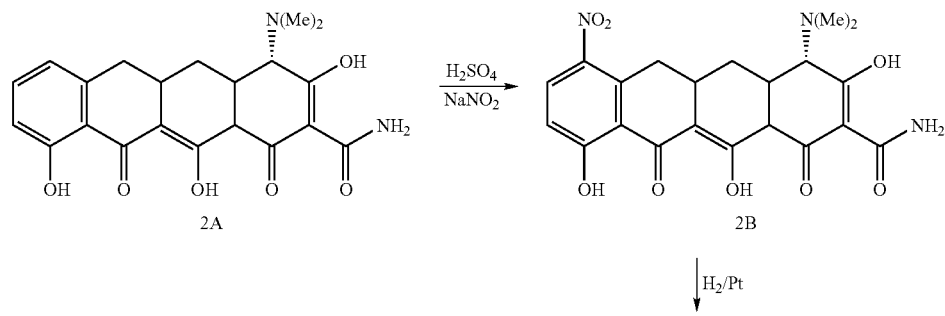

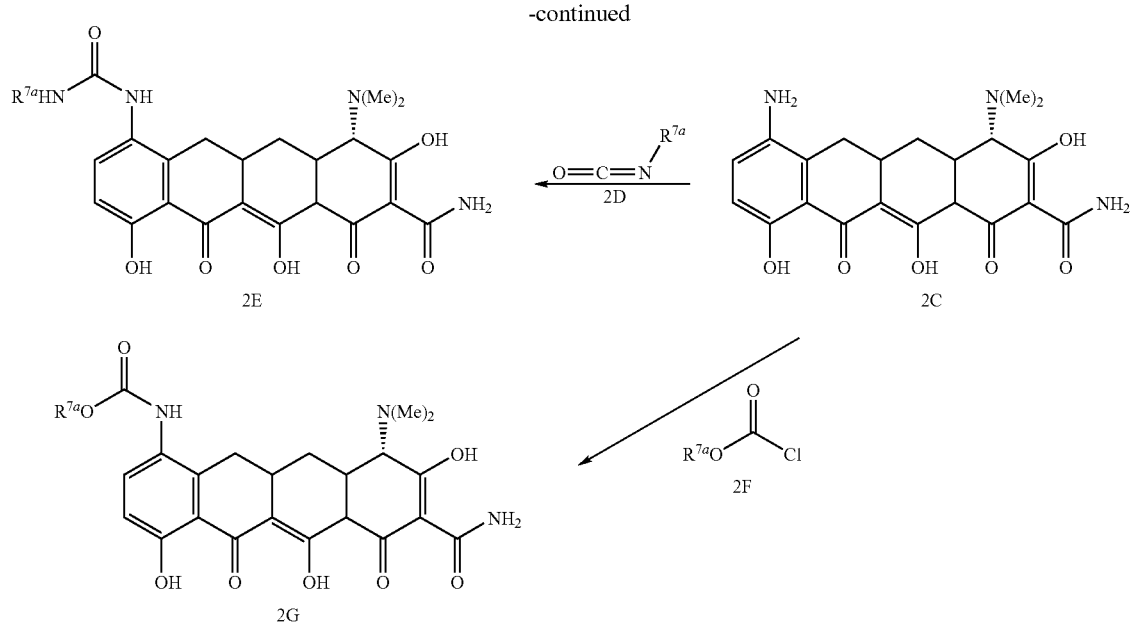

As shown in Scheme 2, tetracycline compounds of the invention wherein $R^7$ is a carbamate or a urea derivative can be synthesized using the following protocol. Sancycline (2A) is treated with $NaNO_2$ under acidic conditions forming 7-nitro sancycline (2B) in a mixture of positional isomers. 7-nitrosancycline (2B) is then treated with $H_2$ gas and a platinum catalyst to form the 7-amino sancycline derivative (2C). To form the urea derivative (2E), isocyanate (2D) is reacted with the 7-amino sancycline derivative (2C). To form the carbamate (2G), the appropriate acid chloride ester (2F) is reacted with 2C.

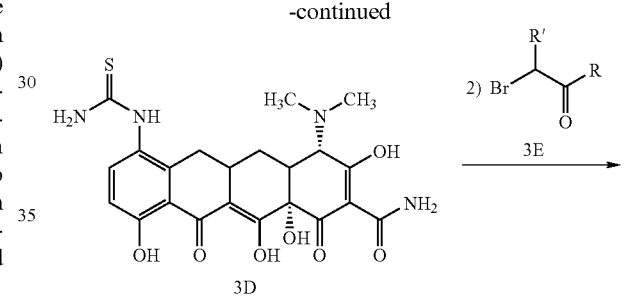

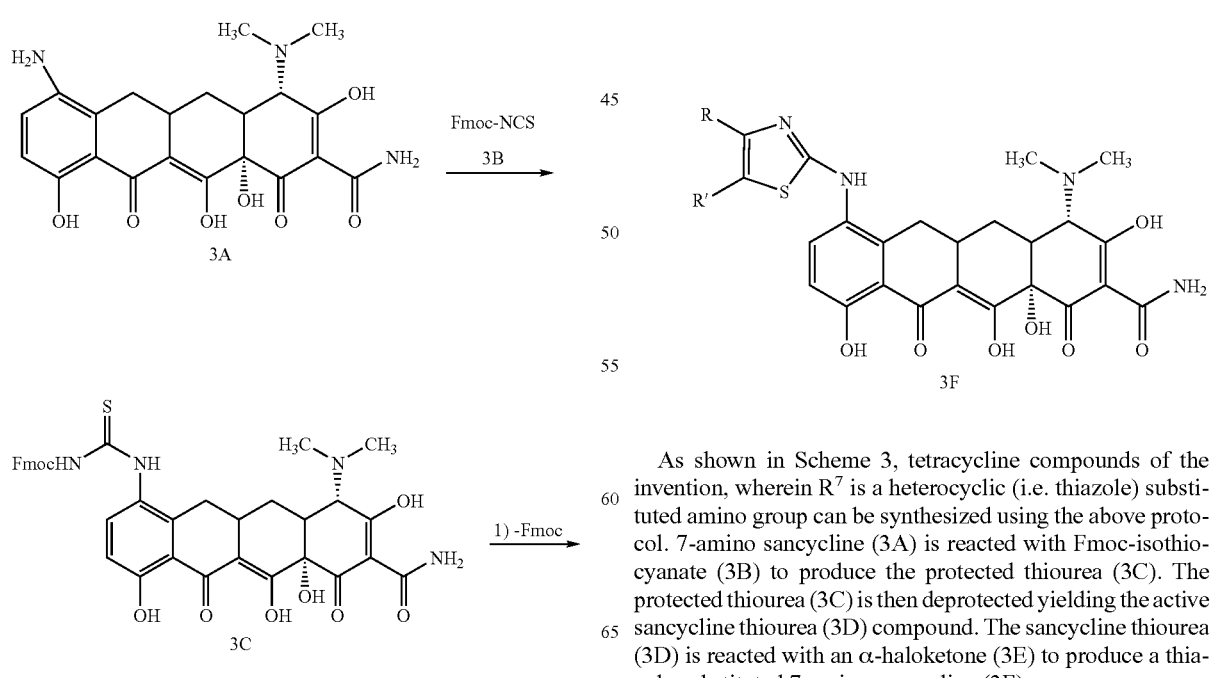

As shown in Scheme 3, tetracycline compounds of the invention, wherein $R^7$ is a heterocyclic (i.e. thiazole) substituted amino group can be synthesized using the above protocol. 7-amino sancycline (3A) is reacted with Fmoc-isothiocyanate (3B) to produce the protected thiourea (3C). The protected thiourea (3C) is then deprotected yielding the active sancycline thiourea (3D) compound. The sancycline thiourea (3D) is reacted with an α-haloketone (3E) to produce a thiazole substituted 7-amino sancycline (3F).

SCHEME 4

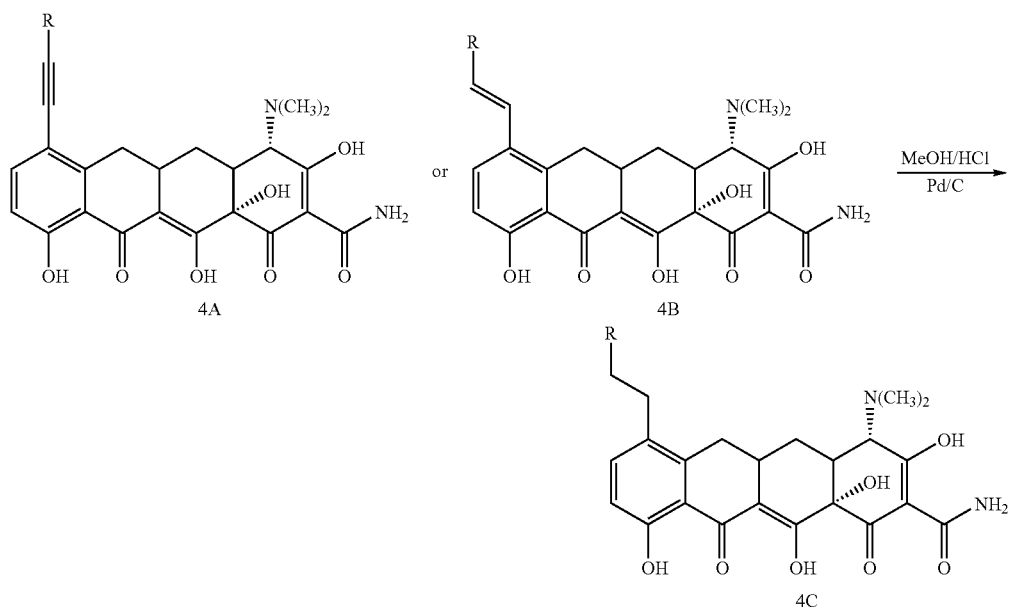

7-alkenyl tetracycline compounds, such as 7-alkynyl sancycline (4A) and 7-alkenyl sancycline (4B), can be hydrogenated to form alkyl 7-substituted tetracycline compounds (e.g., 7-alkyl sancycline, 4C). Scheme 4 depicts the selective hydrogenation of the 7-position double or triple bond, in saturated methanol and hydrochloric acid solution with a palladium/carbon catalyst under pressure, to yield the product.

SCHEME 5

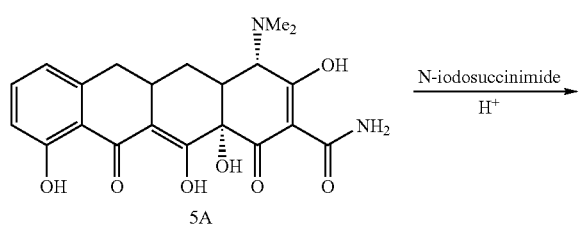

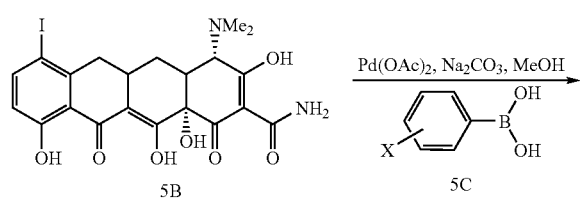

-continued

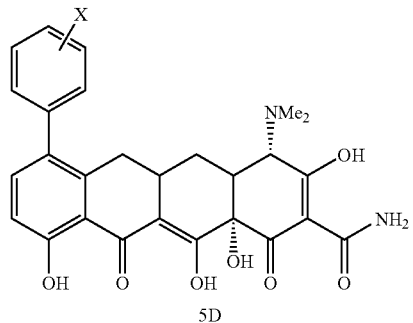

In Scheme 5, a general synthetic scheme for synthesizing 7-position aryl 5 derivatives is shown. A Suzuki coupling of an aryl boronic acid with an iodosancycline compound is shown. An iodo sancycline compound (5B) can be synthesized from sancycline by treating sancycline (5A) with at least one equivalent N-iodosuccinimide (NIS) under acidic conditions. The reaction is quenched, and the resulting 7-iodo sancycline (5B) can then be purified using standard techniques known in the art. To form the aryl derivative, 7-iodo sancycline (5B) is treated with an aqueous base (e.g., $Na_2CO_3$) and an appropriate boronic acid (5C) and under an inert atmosphere. The reaction is catalyzed with a palladium catalyst (e.g., $Pd(OAc)_2$). The product (5D) can be purified by methods known in the art (such as HPLC). Other 7-aryl and alkynyl tetracycline compounds can be synthesized using similar protocols.

The 7-substituted tetracycline compounds of the invention can also be synthesized using Stille cross couplings. Stille cross couplings can be performed using an appropriate tin reagent (e.g., R—SnBu$_3$) and a halogenated tetracycline compound, (e.g., 7-iodosancycline). The tin reagent and the iodosancycline compound can be treated with a palladium catalyst (e.g., Pd(PPh$_3$)$_2$Cl$_2$ or Pd(AsPh$_3$)$_2$Cl$_2$) and, optionally, with an additional copper salt, e.g., CuI. The resulting compound can then be purified using techniques known in the art.

SCHEME 6

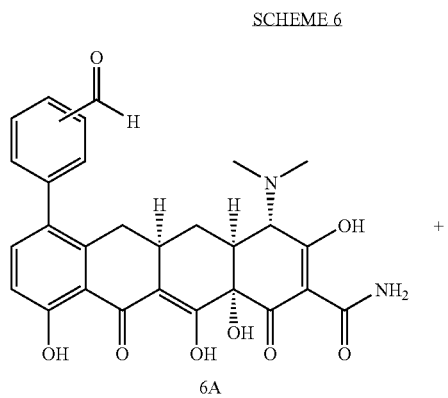

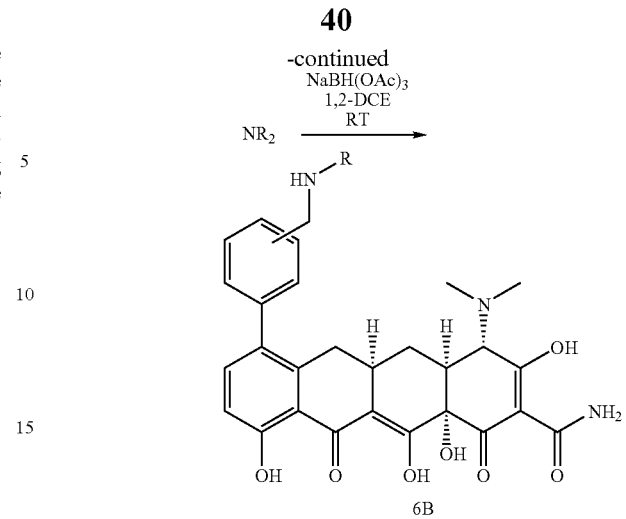

The aryl derivatives formed by Suzuki or Stille couplings, can be further derivitized. For example in Scheme 6, a formyl aryl sancycline (6A), an amine, and a solvent (e.g., 1,2 dichloroethane) are combined in a reaction flask. A reducing agent is then added (e.g., NaBH(OAc)$_3$. and the reaction is allowed to proceed proceed to completion to yield the product (6B). The product is purified and characterized using standard methods.

SCHEME 7

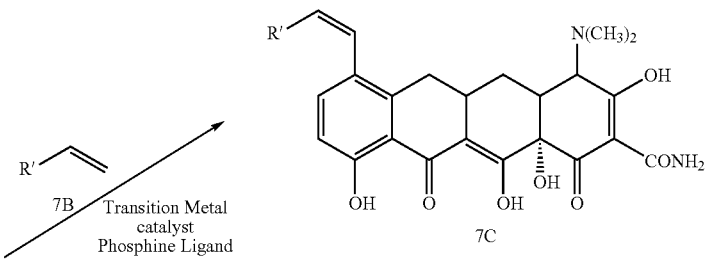

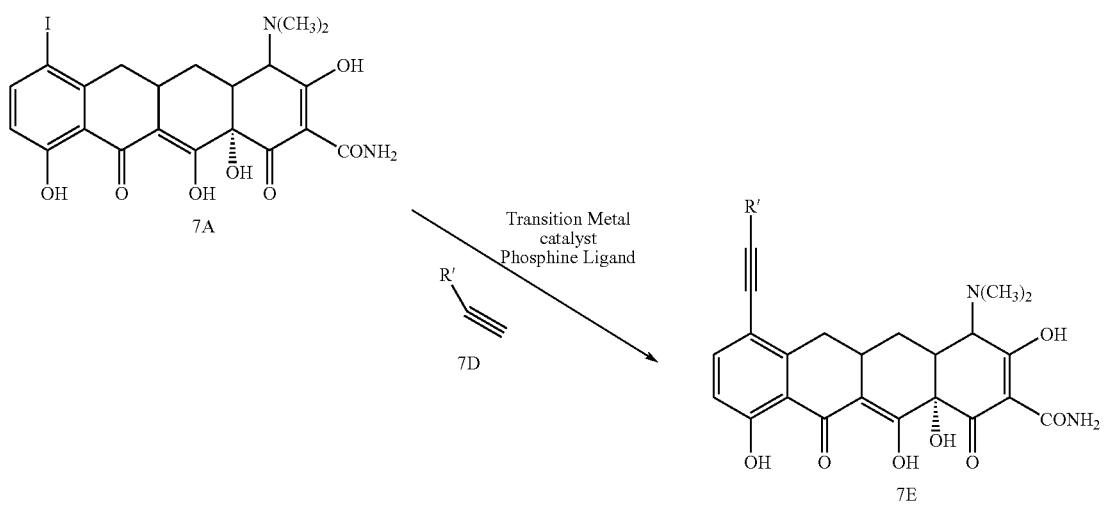

The compounds of the invention can also be synthesized using Heck-type cross coupling reactions. As shown in Scheme 7, Heck-type cross-couplings can be performed by suspending a halogenated tetracycline compound (e.g., 7-iodosancycline, 7A) and an appropriate palladium or other transition metal catalyst (e.g., Pd(OAc)$_2$ and CuI) in an appropriate solvent (e.g., degassed acetonitrile). The substrate, a reactive alkene (7B) or alkyne (7D), and triethylamine are then added and the mixture is heated for several hours, before being cooled to room temperature. The resulting 7-substituted alkenyl (7C) or 7-substituted alkynyl (7E) tetracycline compound can then be purified using techniques known in the art.

SCHEME 8

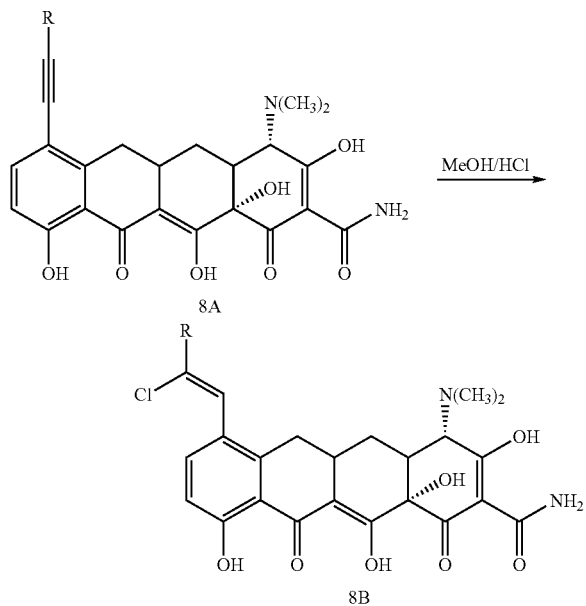

To prepare 7-(2'-Chloro-alkenyl)-tetracycline compounds, the following procedure can be used. 7-(alkynyl)-sancycline (8A) is dissolved in saturated methanol and hydrochloric acid and stirred. The solvent is then removed to yield the product (8B).

The term "alkyl" includes saturated aliphatic groups, including straight-chain alkyl groups (e.g., methyl, ethyl, propyl, butyl, pentyl, hexyl, heptyl, octyl, nonyl, decyl, etc.), branched-chain alkyl groups (isopropyl, tert-butyl, isobutyl, etc.), cycloalkyl (alicyclic) groups (cyclopropyl, cyclopentyl, cyclohexyl, cycloheptyl, cyclooctyl), alkyl substituted cycloalkyl groups, and cycloalkyl substituted alkyl groups. The term alkyl further includes alkyl groups, which can further include oxygen, nitrogen, sulfur or phosphorous atoms replacing one or more carbons of the hydrocarbon backbone. In certain embodiments, a straight chain or branched chain alkyl has 6 or fewer carbon atoms in its backbone (e.g., $C_1$-$C_6$ for straight chain, $C_3$-$C_6$ for branched chain), and more preferably 4 or fewer. Likewise, preferred cycloalkyls have from 3-8 carbon atoms in their ring structure, and more preferably have 5 or 6 carbons in the ring structure. The term $C_1$-$C_6$ includes alkyl groups containing 1 to 6 carbon atoms.

Moreover, the term alkyl includes both "unsubstituted alkyls" and "substituted alkyls", the latter of which refers to alkyl moieties having substituents replacing a hydrogen on one or more carbons of the hydrocarbon backbone. Such substituents can include, for example, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" or an "arylalkyl" moiety is an alkyl substituted with an aryl (e.g., phenylmethyl (benzyl)). The term "alkyl" also includes the side chains of natural and unnatural amino acids.

The term "aryl" includes groups, including 5- and 6-membered single-ring aromatic groups that may include from zero to four heteroatoms, for example, benzene, phenyl, pyrrole, furan, thiophene, thiazole, isothiaozole, imidazole, triazole, tetrazole, pyrazole, oxazole, isooxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, napthridine, indole, benzofuran, purine, benzofuran, deazapurine, or indolizine. Those aryl groups having heteroatoms in the ring structure may also be referred to as "aryl heterocycles", "heterocycles," "heteroaryls" or "heteroaromatics". The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkylaminoacarbonyl, arylalkyl aminocarbonyl, alkenylaminocarbonyl, alkylcarbonyl, arylcarbonyl, arylalkylcarbonyl, alkenylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulflhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings which are not aromatic so as to form a polycycle (e.g., tetralin).

The term "alkenyl" includes unsaturated aliphatic groups analogous in length and possible substitution to the alkyls described above, but that contain at least one double bond.

For example, the term "alkenyl" includes straight-chain alkenyl groups (e.g., ethylenyl, propenyl, butenyl, pentenyl, hexenyl, heptenyl, octenyl, nonenyl, decenyl, etc.), branched-chain alkenyl groups, cycloalkenyl (alicyclic) groups (cyclopropenyl, cyclopentenyl, cyclohexenyl, cycloheptenyl, cyclooctenyl), alkyl or alkenyl substituted cycloalkenyl groups, and cycloalkyl or cycloalkenyl substituted alkenyl groups. The term alkenyl further includes alkenyl groups which include oxygen, nitrogen, sulfur or phosphorous atoms replacing one or more carbons of the hydrocarbon backbone. In certain embodiments, a straight chain or branched chain alkenyl group has 6 or fewer carbon atoms in its backbone (e.g., $C_2$-$C_6$ for straight chain, $C_3$-$C_6$ for branched chain). Likewise, cycloalkenyl groups may have from 3-8 carbon atoms in their ring structure, and more preferably have 5 or 6 carbons in the ring structure. The term $C_2$-$C_6$ includes alkenyl groups containing 2 to 6 carbon atoms.

Moreover, the term alkenyl includes both "unsubstituted alkenyls" and "substituted alkenyls", the latter of which refers to alkenyl moieties having substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "alkynyl" includes unsaturated aliphatic groups analogous in length and possible substitution to the alkyls described above, but which contain at least one triple bond.

For example, the term "alkynyl" includes straight-chain alkynyl groups (e.g., ethynyl, propynyl, butynyl, pentynyl, hexynyl, heptynyl, octynyl, nonynyl, decynyl, etc.), branched-chain alkynyl groups, and cycloalkyl or cycloalkenyl substituted alkynyl groups. The term alkynyl further includes alkynyl groups which include oxygen, nitrogen, sulfur or phosphorous atoms replacing one or more carbons of the hydrocarbon backbone. In certain embodiments, a straight chain or branched chain alkynyl group has 6 or fewer carbon atoms in its backbone (e.g., $C_2$-$C_6$ for straight chain, $C_3$-$C_6$ for branched chain). The term $C_2$-$C_6$ includes alkynyl groups containing 2 to 6 carbon atoms.

Moreover, the term alkynyl includes both "unsubstituted alkynyls" and "substituted alkynyls", the latter of which refers to alkynyl moieties having substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Unless the number of carbons is otherwise specified, "lower alkyl" as used herein means an alkyl group, as defined above, but having from one to five carbon atoms in its backbone structure. "Lower alkenyl" and "lower alkynyl" have chain lengths of, for example, 2-5 carbon atoms.

The term "acyl" includes compounds and moieties which contain the acyl radical ($CH_3CO$—) or a carbonyl group. It includes substituted acyl moieties. The term "substituted acyl" includes acyl groups where one or more of the hydrogen atoms are replaced by for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "acylamino" includes moieties wherein an acyl moiety is bonded to an amino group. For example, the term includes alkylcarbonylamino, arylcarbonylamino, carbamoyl and ureido groups.

The term "aroyl" includes compounds and moieties with an aryl or heteroaromatic moiety bound to a carbonyl group. Examples of aroyl groups include phenylcarboxy, naphthyl carboxy, etc.

The terms "alkoxyalkyl", "alkylaminoalkyl" and "thioalkoxyalkyl" include alkyl groups, as described above, which further include oxygen, nitrogen or sulfur atoms replacing one or more carbons of the hydrocarbon backbone, e.g., oxygen, nitrogen or sulfur atoms.

The term "alkoxy" includes substituted and unsubstituted alkyl, alkenyl, and alkynyl groups covalently linked to an oxygen atom. Examples of alkoxy groups include methoxy, ethoxy, isopropyloxy, propoxy, butoxy, and pentoxy groups. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy, trichloromethoxy, etc.

The term "amine" or "amino" includes compounds where a nitrogen atom is covalently bonded to at least one carbon or heteroatom. The term includes "alkyl amino" which comprises groups and compounds wherein the nitrogen is bound to at least one additional alkyl group. The term "dialkyl amino" includes groups wherein the nitrogen atom is bound to at least two additional alkyl groups. The term "arylamino" and "diarylamino" include groups wherein the nitrogen is bound to at least one or two aryl groups, respectively. The term "alkylarylamino," "alkylaminoaryl" or "arylaminoalkyl" refers to an amino group which is bound to at least one alkyl group and at least one aryl group. The term "alkaminoalkyl" refers to an alkyl, alkenyl, or alkynyl group bound to a nitrogen atom which is also bound to an alkyl group.

The term "amide," "amido" or "aminocarbonyl" includes compounds or moieties which contain a nitrogen atom which is bound to the carbon of a carbonyl or a thiocarbonyl group. The term includes "alkaminocarbonyl" or "alkylaminocarbonyl" groups which include alkyl, alkenyl, aryl or alkynyl groups bound to an amino group bound to a carbonyl group. It includes arylaminocarbonyl and arylcarbonylamino groups which include aryl or heteroaryl moieties bound to an amino group which is bound to the carbon of a carbonyl or thiocarbonyl group. The terms "alkylaminocarbonyl," "alkenylaminocarbonyl," "alkynylaminocarbonyl," "arylaminocarbonyl," "alkylcarbonylamino," "alkenylcarbonylamino," "alkynylcarbonylamino," and "arylcarbonylamino" are included in term "amide." Amides also include urea groups (aminocarbonylamino) and carbamates (oxycarbonylamino).

The term "carbonyl" or "carboxy" includes compounds and moieties which contain a carbon connected with a double bond to an oxygen atom. The carbonyl can be further substituted with any moiety which allows the compounds of the invention to perform its intended function. For example, carbonyl moieties may be substituted with alkyls, alkenyls, alkynyls, aryls, alkoxy, aminos, etc. Examples of moieties which contain a carbonyl include aldehydes, ketones, carboxylic acids, amides, esters, anhydrides, etc.

The term "thiocarbonyl" or "thiocarboxy" includes compounds and moieties which contain a carbon connected with a double bond to a sulfur atom.

The term "ether" includes compounds or moieties which contain an oxygen bonded to two different carbon atoms or heteroatoms. For example, the term includes "alkoxyalkyl" which refers to an alkyl, alkenyl, or alkynyl group covalently bonded to an oxygen atom which is covalently bonded to another alkyl group.

The term "ester" includes compounds and moieties which contain a carbon or a heteroatom bound to an oxygen atom which is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc. The alkyl, alkenyl, or alkynyl groups are as defined above.

The term "thioether" includes compounds and moieties which contain a sulfur atom bonded to two different carbon or hetero atoms. Examples of thioethers include, but are not limited to alkthioalkyls, alkthioalkenyls, and alkthioalkynyls. The term "alkthioalkyls" include compounds with an alkyl, alkenyl, or alkynyl group bonded to a sulfur atom which is bonded to an alkyl group. Similarly, the term "alkthioalkenyls" and alkthioalkynyls" refer to compounds or moieties wherein an alkyl, alkenyl, or alkynyl group is bonded to a sulfur atom which is covalently bonded to an alkynyl group.

The term "hydroxy" or "hydroxyl" includes groups with an —OH or —O⁻.

The term "halogen" includes fluorine, bromine, chlorine, iodine, etc. The term "perhalogenated" generally refers to a moiety wherein all hydrogens are replaced by halogen atoms.

The terms "polycyclyl" or "polycyclic radical" refer to two or more cyclic rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, alkylaminoacarbonyl, arylalkylaminocarbonyl, alkenylaminocarbonyl, alkylcarbonyl, arylcarbonyl, arylalkyl carbonyl, alkenylcarbonyl, aminocarbonyl, alkylthiocarbonyl, alkoxyl, phosphate, phosphonato, phosphinato, cyano, amido, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkyl, alkylaryl, or an aromatic or heteroaromatic moiety.

The term "heteroatom" includes atoms of any element other than carbon or hydrogen. Preferred heteroatoms are nitrogen, oxygen, sulfur and phosphorus.

The term "prodrug moiety" includes moieties which can be metabolized in vivo to a hydroxyl group and moieties which may advantageously remain esterified in vivo. Preferably, the prodrugs moieties are metabolized in vivo by esterases or by other mechanisms to hydroxyl groups or other advantageous groups. Examples of prodrugs and their uses are well known in the art (See, e.g., Berge et al. (1977) "Pharmaceutical Salts", *J. Pharm. Sci.* 66:1-19). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branch or unbranched lower alkyl ester moieties, (e.g., propionoic acid esters), lower alkenyl esters, di-lower alkyl-amino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Preferred prodrug moieties are propionoic acid esters and acyl esters.

It will be noted that the structure of some of the tetracycline compounds of this invention includes asymmetric carbon atoms. It is to be understood accordingly that the isomers arising from such asymmetry (e.g., all enantiomers and diastereomers) are included within the scope of this invention, unless indicated otherwise. Such isomers can be obtained in substantially pure form by classical separation techniques and by stereochemically controlled synthesis. Furthermore, the structures and other compounds and moieties discussed in this application also include all tautomers thereof.

The invention also pertains to methods for treating a tetracycline responsive states in subjects, by administering to a subject an effective amount of a 7-substituted tetracycline compound of the invention (e.g., a compound of Formula (I) or shown in Table 1), such that the tetracycline responsive state is treated.

The language "tetracycline compound responsive state" includes states which can be treated, prevented, or otherwise ameliorated by the administration of a tetracycline compound of the invention. Tetracycline compound responsive states include bacterial infections (including those which are resistant to other tetracycline compounds), cancer, diabetes, and other states for which tetracycline compounds have been found to be active (see, for example, U.S. Pat. Nos. 5,789,395; 5,834,450; and 5,532,227). Compounds of the invention can be used to prevent or control important mammalian and veterinary diseases such as diarrhea, urinary tract infections, infections of skin and skin structure, ear, nose and throat infections, wound infection, mastitis and the like. In addition, methods for treating neoplasms using tetracycline compounds of the invention are also included (van der Bozert et al., *Cancer Res.*, 48:6686-6690 (1988)).

Bacterial infections may be caused by a wide variety of gram positive and gram negative bacteria. The compounds of the invention are useful as antibiotics against organisms which are resistant to other tetracycline compounds. The antibiotic activity of the tetracycline compounds of the invention may be determined using the method discussed in Example 2, or by using the in vitro standard broth dilution method described in Waitz, J. A., *National Commission for*

*Clinical Laboratory Standards, Document M7-A2,* vol. 10, no. 8, pp. 13-20, $2^{nd}$ edition, Villanova, Pa. (1990).

The tetracycline compounds may also be used to treat infections traditionally treated with tetracycline compounds such as, for example, rickettsiae; a number of gram-positive and gram-negative bacteria; and the agents responsible for lymphogranuloma venereum, inclusion conjunctivitis, psittacosis. The tetracycline compounds may be used to treat infections of, e.g., *K. pneumoniae, Salmonella, E. hirae, A. baumanii, B. catarrhalis, H. influenzae, P. aeruginosa, E. faecium, E. coli, S. aureus* or *E. faecalis*. In one embodiment, the tetracycline compound is used to treat a bacterial infection that is resistant to other tetracycline antibiotic compounds. The tetracycline compound of the invention may be administered with a pharmaceutically acceptable carrier.

The language "effective amount" of the compound is that amount necessary or sufficient to treat or prevent a tetracycline compound responsive state. The effective amount can vary depending on such factors as the size and weight of the subject, the type of illness, or the particular tetracycline compound. For example, the choice of the tetracycline compound can affect what constitutes an "effective amount". One of ordinary skill in the art would be able to study the aforementioned factors and make the determination regarding the effective amount of the tetracycline compound without undue experimentation.

The invention also pertains to methods of treatment against microorganism infections and associated diseases. The methods include administration of an effective amount of one or more tetracycline compounds to a subject. The subject can be either a plant or, advantageously, an animal, e.g., a mammal, e.g., a human.

In the therapeutic methods of the invention, one or more tetracycline compounds of the invention may be administered alone to a subject, or more typically a compound of the invention will be administered as part of a pharmaceutical composition in mixture with conventional excipient, i.e., pharmaceutically acceptable organic or inorganic carrier substances suitable for parenteral, oral or other desired administration and which do not deleteriously react with the active compounds and are not deleterious to the recipient thereof.

The invention also pertains to pharmaceutical compositions comprising a therapeutically effective amount of a tetracycline compound (e.g., a compound of Formula 1, Table 2, or other compound described herein) and, optionally, a pharmaceutically acceptable carrier.

The language "pharmaceutically acceptable carrier" includes substances capable of being coadministered with the tetracycline compound(s), and which allow both to perform their intended function, e.g., treat or prevent a tetracycline responsive state. Suitable pharmaceutically acceptable carriers include but are not limited to water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethyl-cellulose, polyvinylpyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously react with the active compounds of the invention.

The tetracycline compounds of the invention that are basic in nature are capable of forming a wide variety of salts with various inorganic and organic acids. The acids that may be used to prepare pharmaceutically acceptable acid addition salts of the tetracycline compounds of the invention that are basic in nature are those that form non-toxic acid addition salts, i.e., salts containing pharmaceutically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and palmoate [i.e., 1,1'-methylene-bis-(2-hydroxy-3-naphthoate)]salts. Although such salts must be pharmaceutically acceptable for administration to a subject, e.g., a mammal, it is often desirable in practice to initially isolate a tetracycline compound of the invention from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained.

The preparation of other tetracycline compounds of the invention not specifically described in the foregoing experimental section can be accomplished using combinations of the reactions described above that will be apparent to those skilled in the art.

The preparation of other tetracycline compounds of the invention not specifically described in the foregoing experimental section can be accomplished using combinations of the reactions described above that will be apparent to those skilled in the art.

The tetracycline compounds of the invention that are acidic in nature are capable of forming a wide variety of base salts. The chemical bases that may be used as reagents to prepare pharmaceutically acceptable base salts of those tetracycline compounds of the invention that are acidic in nature are those that form non-toxic base salts with such compounds. Such non-toxic base salts include, but are not limited to those derived from such pharmaceutically acceptable cations such as alkali metal cations (e.g., potassium and sodium) and alkaline earth metal cations (e.g., calcium and magnesium), ammonium or water-soluble amine addition salts such as N-methylglucamine-(meglumine), and the lower alkanolammonium and other base salts of pharmaceutically acceptable organic amines. The pharmaceutically acceptable base addition salts of tetracycline compounds of the invention that are acidic in nature may be formed with pharmaceutically acceptable cations by conventional methods. Thus, these salts may be readily prepared by treating the tetracycline compound of the invention with an aqueous solution of the desired pharmaceutically acceptable cation and evaporating the resulting solution to dryness, preferably under reduced pressure. Alternatively, a lower alkyl alcohol solution of the tetracycline compound of the invention may be mixed with an alkoxide of the desired metal and the solution subsequently evaporated to dryness.

The preparation of other tetracycline compounds of the invention not specifically described in the foregoing experimental section can be accomplished using combinations of the reactions described above that will be apparent to those skilled in the art.

The tetracycline compounds of the invention and pharmaceutically acceptable salts thereof can be administered via either the oral, parenteral or topical routes. In general, these compounds are most desirably administered in effective dosages, depending upon the weight and condition of the subject being treated and the particular route of administration chosen. Variations may occur depending upon the species of the subject being treated and its individual response to said medicament, as well as on the type of pharmaceutical formulation chosen and the time period and interval at which such administration is carried out.

The pharmaceutical compositions of the invention may be administered alone or in combination with other known compositions for treating tetracycline responsive states in a subject, e.g., a mammal. Preferred mammals include pets (e.g., cats, dogs, ferrets, etc.), farm animals (cows, sheep, pigs, horses, goats, etc.), lab animals (rats, mice, monkeys, etc.), and primates (chimpanzees, humans, gorillas). The language "in combination with" a known composition is intended to include simultaneous administration of the composition of the invention and the known composition, administration of the composition of the invention first, followed by the known composition and administration of the known composition first, followed by the composition of the invention. Any of the therapeutically composition known in the art for treating tetracycline responsive states can be used in the methods of the invention.

The tetracycline compounds of the invention may be administered alone or in combination with pharmaceutically acceptable carriers or diluents by any of the routes previously mentioned, and the administration may be carried out in single or multiple doses. For example, the novel therapeutic agents of this invention can be administered advantageously in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the therapeutically-effective compounds of this invention are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration (including intraperitoneal, subcutaneous, intravenous, intradermal or intramuscular injection), solutions of a therapeutic compound of the present invention in either sesame or peanut oil or in aqueous propylene glycol may be employed. The aqueous solutions should be suitably buffered (preferably pH greater than 8) if necessary and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art. For parenteral application, examples of suitable preparations include solutions, preferably oily or aqueous solutions as well as suspensions, emulsions, or implants, including suppositories. Therapeutic compounds may be formulated in sterile form in multiple or single dose formats such as being dispersed in a fluid carrier such as sterile physiological saline or 5% saline dextrose solutions commonly used with injectables.

Additionally, it is also possible to administer the compounds of the present invention topically when treating inflammatory conditions of the skin. Examples of methods of topical administration include transdermal, buccal or sublingual application. For topical applications, therapeutic compounds can be suitably admixed in a pharmacologically inert topical carrier such as a gel, an ointment, a lotion or a cream. Such topical carriers include water, glycerol, alcohol, propylene glycol, fatty alcohols, triglycerides, fatty acid esters, or mineral oils. Other possible topical carriers are liquid petrolatum, isopropylpalmitate, polyethylene glycol, ethanol 95%, polyoxyethylene monolauriate 5% in water, sodium lauryl sulfate 5% in water, and the like. In addition, materials such as anti-oxidants, humectants, viscosity stabilizers and the like also may be added if desired.

For enteral application, particularly suitable are tablets, dragees or capsules having talc and/or carbohydrate carrier binder or the like, the carrier preferably being lactose and/or corn starch and/or potato starch. A syrup, elixir or the like can be used wherein a sweetened vehicle is employed. Sustained release compositions can be formulated including those wherein the active component is protected with differentially degradable coatings, e.g., by microencapsulation, multiple coatings, etc.

In addition to treatment of human subjects, the therapeutic methods of the invention also will have significant veterinary applications, e.g. for treatment of livestock such as cattle, sheep, goats, cows, swine and the like; poultry such as chickens, ducks, geese, turkeys and the like; horses; and pets such as dogs and cats. Also, the compounds of the invention may be used to treat non-animal subjects, such as plants.

It will be appreciated that the actual preferred amounts of active compounds used in a given therapy will vary according to the specific compound being utilized, the particular compositions formulated, the mode of application, the particular site of administration, etc. Optimal administration rates for a given protocol of administration can be readily ascertained by those skilled in the art using conventional dosage determination tests conducted with regard to the foregoing guidelines.

In general, compounds of the invention for treatment can be administered to a subject in dosages used in prior tetracycline therapies. See, for example, the *Physicians' Desk Reference*. For example, a suitable effective dose of one or more compounds of the invention will be in the range of from 0.01 to 100 milligrams per kilogram of body weight of recipient per day, preferably in the range of from 0.1 to 50 milligrams per kilogram body weight of recipient per day, more preferably in the range of 1 to 20 milligrams per kilogram body weight of recipient per day. The desired dose is suitably administered once daily, or several sub-doses, e.g. 2 to 5 sub-doses, are administered at appropriate intervals through the day, or other appropriate schedule. It will also be understood that normal, conventionally known precautions will be taken regarding the administration of tetracyclines generally to ensure their efficacy under normal use circumstances. Especially when employed for therapeutic treatment of humans and animals in vivo, the practitioner should take all sensible precautions to avoid conventionally known contradictions and toxic effects. Thus, the conventionally recognized adverse reactions of gastrointestinal distress and inflammations, the renal toxicity, hypersensitivity reactions, changes in blood, and impairment of absorption through aluminum, calcium, and magnesium ions should be duly considered in the conventional manner.

Furthermore, the invention also pertains to the use of a tetracycline compound of formula I, for the preparation of a medicament. The medicament may include a pharmaceutically acceptable carrier and the tetracycline compound is an effective amount, e.g., an effective amount to treat a tetracycline responsive state.

EXEMPLIFICATION OF THE INVENTION

Compounds of the invention may be made as described below, with modifications to the procedure below within the skill of those of ordinary skill in the art.

Example 1

Synthesis of 7-Substituted Sancyclines

7 Iodo Sancycline

One gram of sancycline was dissolved in 25 mL of TFA (trifluoroacetic acid) that was cooled to 0 C (on ice). 1.2 equivalents of N-iodosuccinimide (NIS) was added to the reaction mixture and reacted for forty minutes. The reaction was removed from the ice bath and was allowed to react at room temperature for an additional five hours. The mixture was then analyzed by HPLC and TLC, was driven to completion by the stepwise addition of NIS. After completion of the reaction, the TFA was removed in vacuo and 3 mL of MeOH was added to dissolve the residue. The methanolic solution was the added slowly to a rapidly stirring solution of diethyl ether to form a greenish brown precipitate. The 7-iodo isomer of sancycline was purified by treating the 7-iodo product with activated charcoal., filtering through Celite, and subsequent removal of the solvent in vacuo to produce the 7-isomer compound as a pure yellow solid in 75% yield.

MS(M+H) (formic acid solvent) 541.3.
\Rt: Hypersil C18 BDS Column, 11.73
$^1$H NMR (Methanol $d_4$-300 MHz) δ 7.87-7.90 (d, 1H), 6.66-6.69 (d, 1H), 4.06 (s, 1H), 2.98 (s, 6H), 2.42 (m, 1H), 2.19 (m, 1H), 1.62 (m, 4H), 0.99 (m, 2H)

Compound B (7-Phenyl Sancycline)

7-iodosancycline, 150 mg (0.28 mM), Pd(OAc)$_2$ and 10 mL of MeOH are added to a flask with a stir bar and the system degassed 3x using argon. Na$_2$CO$_3$ (87 mg, 0.8 mM) dissolved in water and argon degassed is added via syringe is added along with phenylboronic acid (68 mg, 0.55 mM) in MeOH that was also degassed. The reaction was followed by HPLC for 2 hours and cooled to room temperature. The solution was filtered, and dried to produce a crude mixture. The solid was dissolved in dimethylformamide and injected onto a preparative HPLC system using C18 reverse-phase silica. The fraction at 36-38 minutes was isolated, and the solvent removed in vacuo to yield the product plus salts. The salts were removed by extraction into 50:25:25 water, butanol, ethyl acetate and dried in vacuo. This solid was dissolved in MeOH and the HCl salt made by bubbling in HCl gas. The solvent was removed to produce the product in 42% yield as a yellow solid.

Rt 21.6 min: MS (M+H, formic acid solvent): 491.3
$^1$H NMR (Methanol $d_4$-300 MHz) δ 7.87 (d, J=8.86 Hz, 1H), 7.38 (m, 5H), 6.64 (d, 8.87 Hz, 1H), 4.00 (s, 1H), 3.84 (s, 2H), 3.01 (s, 6H), 2.46 (m, 2H), 1.63 (m, 4H), 0.95 (m, 2H)

Compound E (7-(4'-Chlorophenyl) Sancycline)

7-iodosancycline, 500 mg (0.91 mM), Pd(OAc)$_2$ 21 mg, and 20 mL of MeOH are added to a flask with a stir bar and the system degassed 3x using argon. Na$_2$CO$_3$ (293 mg, 2.8 mM) dissolved in water and argon degassed is added via syringe is added along with 4-Cl-phenylboronic acid (289 mg, 1.85 mM) in MeOH that was also degassed. The reaction was followed by HPLC for 45 minutes and cooled to room temperature. The solution was filtered, and dried to produce a crude mixture. The solid was dissolved in dimethylformamide and injected onto a preparative HPLC system using C18 reverse-phase silica. The fraction at 39 minutes was isolated, and the solvent removed in vacuo to yield the product plus salts. The salts were removed by extraction into 50:25:25 water, butanol, ethyl acetate and dried in vacuo. This solid was dissolved in MeOH and the HCl salt made by bubbling in HCl gas. The solvent was removed to produce the product in 57% yield as a yellow solid.

Rt 20.3 min: MS (M+H, formic acid solvent): 525.7
$^1$H NMR (Methanol $d_4$-300 MHz) δ 7.49-7.52 (d, J=8.54 Hz, 1H), 6.99-7.01 (d, 8.61 Hz, 1H), 4.12 (s, 1H), 3.67 (m, 1H), 3.06 (s, 6H), 2.58 (m, 2H), 1.62(m, 4H), 1.01 (m, 2H)

Compound A (7-(4'-Fluorophenyl) Sancycline)

7-iodosancycline, 200 mg (0.3 mM), Pd(OAc)$_2$ 8.3 mg, and 10 mL of MeOH are added to a flask with a stir bar and the system degassed 3× using argon. Na$_2$CO$_3$ (104 mg, 1.1 mM) dissolved in water and argon degassed is added via syringe is added along with 4-F-phenylboronic acid (104 mg, 0.7 mM) in MeOH that was also degassed. The reaction was followed by HPLC for 20 minutes and cooled to room temperature. The solution was filtered, and dried to produce a crude mixture. The solid was dissolved in dimethylformamide and injected onto a preparative HPLC system using C18 reverse-phase silica. The fraction at 19-20 minutes was isolated, and the solvent removed in vacuo to yield the product plus salts. The salts were removed by extraction into 50:25:25 water, butanol, ethyl acetate and dried in vacuo. This solid was dissolved in MeOH and the HCl salt made by bubbling in HCl gas. The solvent was removed to produce the product in 47% yield as a yellow solid.

Rt 19.5 min: MS (M+H, formic acid solvent): 509.4
$^1$H NMR (Methanol $d_4$-300 MHz) δ 6.92-6.95 (d, 1H), 7.45-7.48 (d, 1H), 7.15-7.35 (m, 4H), 4.05 (s, 1H), 3.62 (m, 1H), 3.08 (s, 6H), 2.55 (m, 2H), 1.65(m, 4H), 1.00 (m, 2H)

Compound AT (7-(4'-Iodo-1',3'-carboethoxy-1',3'-butadiene) Sancycline)

7-I-Sancycline (1 gm, 1.86 mmol), was dissolved in 25 mL of acetonitrile and was degassed and purged with nitrogen (three times). To this suspension Pd(OAc)$_2$ (20 mg, 0.089 mmol), CuI (10 mg, 0.053 mmol), (o-tolyl)$_3$P (56 mg, 0.183 mmol) were added and purged with nitrogen. Ethyl propiolate (1 mL) and triethylamine (1 mL) were added to the suspension. It turned to a brown solution upon addition of Et₃N. The reaction mixture was then heated to 70 degrees C. for two hours. Progress of the reaction was monitored by HPLC. It was then cooled down to room temperature and was filtered through celite. Evaporation of the solvent gave a brown solid, which was then purified on preparative HPLC to give a yellow solid.

Compound AI (7-(2'-Chloroethenyl)-Sancycline)

To a solution/suspension of 0.65 g (1 mmol) of 7-iodo sancycline, 0.05 g tetrakis triphenyl phosphinato palladate, 0.012 g palladium acetate, 0.05 g copper (I) iodide in 10 mL acetonitrile, 2 mL triethylamine and 0.5 g trimethylsilyl acetylene was added at room temperature. The reaction proceeded for two hours before being filtered through a celite bed and concentrated. The crude product was purified by preparative HPLC. The collected fractions were concentrated and the residue was taken up in about 1 mL of methanol and 2 mL of HCl saturated methanol. The product was precipitated with ether. The solids were filtered off and dried under reduced pressure. NMR spectroscopy and LC-MS showed that the compound was 7-(2-chloroethenyl) sancycline.

Compound D (7-(4'-aminophenyl) Sancycline)

To a solution of 200 mg of 7-(4-nitrophenyl)sancycline in 50 mL methanol, 10 mg of 10% palladium on charcoal catalyst was added. The reaction mixture was shaken under 40 psi hydrogen pressure for 2 hours and was then filtered followed by concentration. The residue was further purified by preparative HPLC. 35 mg was isolated as the HCl salt and the structure was proved by MNR and LC-MS to be 7-(4-aminophenyl)sancycline.

Compound EF (1,8-Di-7-Sancyclinyl-1,8-Heptyne)

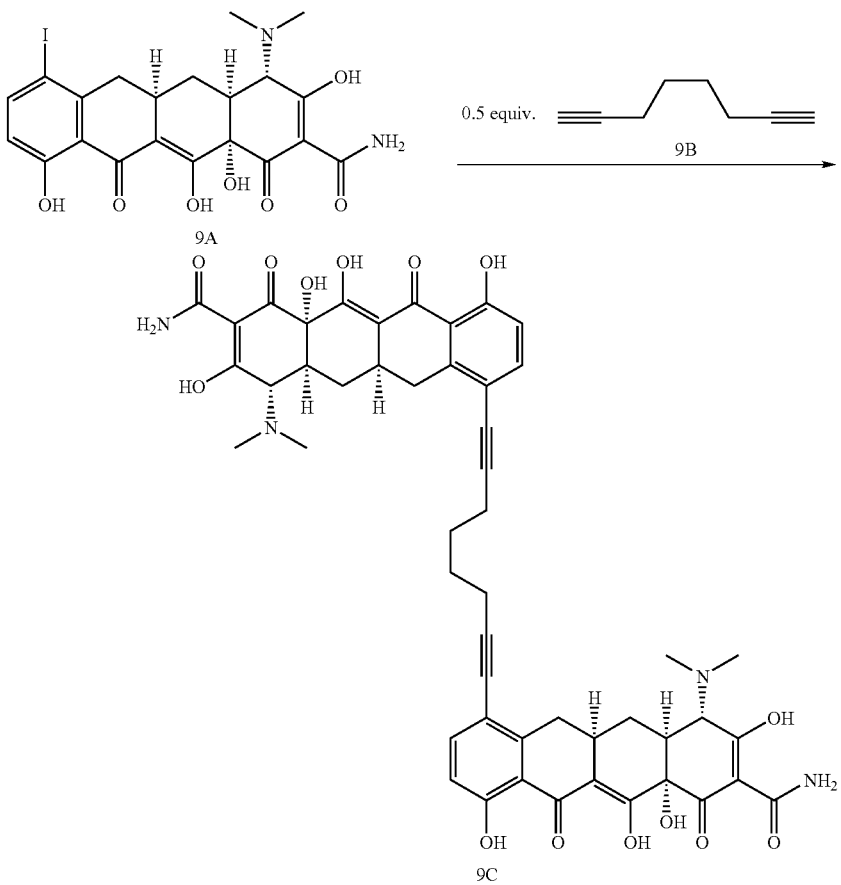

SCHEME 9

A flask was charged with 7-iodosancycline (3.0 g, 4.57 mmol, 9A), Pd(OAc)₂ (0.102 g, 0.46 mmol), CuI (0.044 g, 0.23 mmol), and P(o-Tol)₃ (0.278 g, 0.91 mmol) and the contents were suspended in anhydrous acetonitrile. After purging this mixture with dinitrogen at 60° C. (bath temperature), 1,7-octadiyne (0.305 mL, 2.29 mmol, 9B) was added to it, followed by the addition of triethylamine. The dark colored solution was stirred at 60° C. for 3 h, filtered through a bed of celite, dried. A methanol: DMF:TFA (90:8:2) solution of the product (9C) was purified on preparative HPLC column. The final product (9C) was characterized by HPLC, MS, and ¹H NMR spectroscopy.

Compound U
(7-(NN-Dimethylpropynyl)-Sancycline)

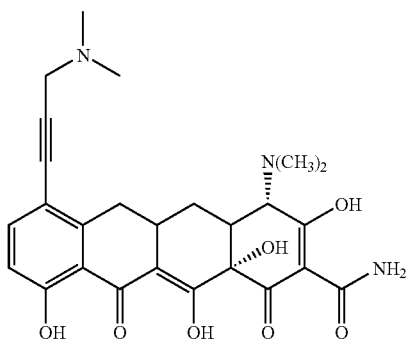

7-I-Sancycline (1 gm, 1.86 mmol), taken in 25 mL of acetonitrile was degassed and purged with nitrogen (three times). To this suspension Pd(OAc)$_2$ (20 mg, 0.089 mmol), CuI (10 mg, 0.053 mmol), (o-tolyl)3P (56 mg, 0.183 mmol) were added and purged with nitrogen for few minutes. NN-Dimethylpropyne (308 mg, 3.72 mmol) and triethylamine (1 mL) were added to the suspension. It was turned into a brown solution upon addition of Et$_3$N. The reaction mixture was then heated to 70° C. for 3 hours. Progress of the reaction was monitored by HPLC. It was then cooled down to rt and was filtered through celite. Evaporation of the solvent gave a brown solid, which was then purified on preparative HPLC to give a yellow solid. The structure of this compound has been characterized using 1H NMR, HPLC, and MS.

Compound BA
(7-(2'-Chloro-3-Hydroxypropenyl)-Sancycline)

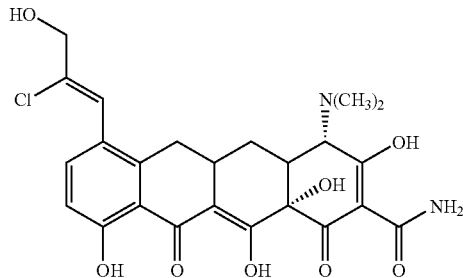

7-(alkynyl)-sancycline (100 mg) was taken in 20 ml of saturated MeOH/HCl and stirred for 20 min. The solvent was then evaporated to give a yellow powder. The structure of this compound has been characterized using 1H NMR, HPLC, and MS.

Compound CC
(7-(3'-Methoxyphenylethyl)-Sancycline)

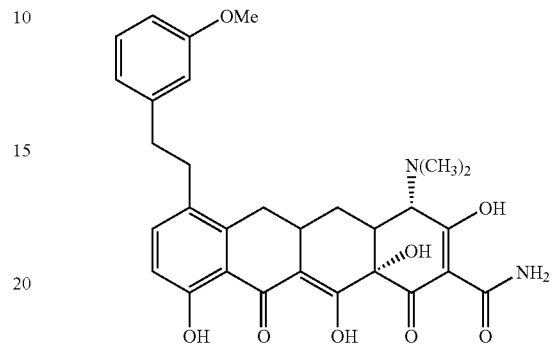

7-(3'-Methoxyphenylethynyl)-sancycline (1 mmol)/was taken in saturated solution of MeOH/HCl. To this solution 10% Pd/C was added and was subjected to hydrogenation at 50 psi for 12 hrs. It was then filtered through celite. The solvent was evaporated to give a yellow powder. Finally, it was precipitated from MeOH/diethylether. The structure of this compound has been characterized using 1H NMR, HPLC, and MS.

Compound CW
((2-Dimethylamino-Acetylamino)-Sancycline)

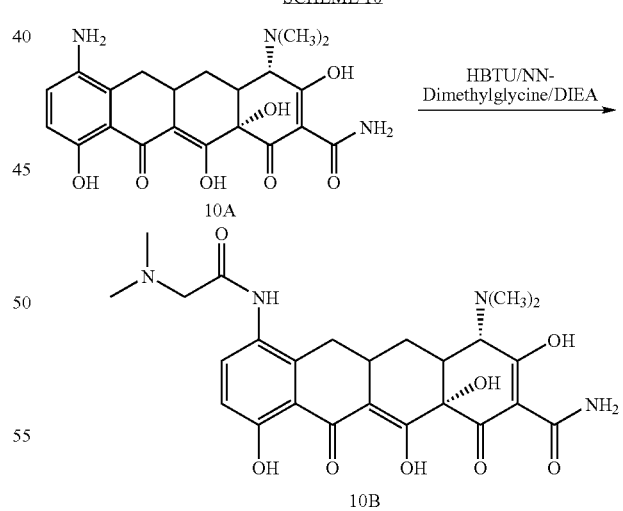

NN-Dimethylglycine (1.2 mmol) was dissolved in DMF (5 mL) and O-Benzotriazol-1-yl-N,N,N', N',-tetramethyluronium hexafluorophosphate (HBTU, 1.2 mmol) was added. The solution was then stirred for 5 minutes at room temperature. To this solution, 7-aminosancycline (1 mmol, 10A) was added, followed by the addition of diisopropylethyl amine (DIEA, 1.2 mmol). The reaction was then stirred at room temperature for 2 hours. The solvent, DMF, was removed on vaccum. The crude material was dissolved in 5 mL of MeOH and filtered using autovials and purified using preparative HPLC. The structure of the product (10B) has been characterized using 1H NMR, HPLC, and MS.

Compound DJ
(7-(N-Methylsulphonamidopropargylamine) Sancycline)

SCHEME 11

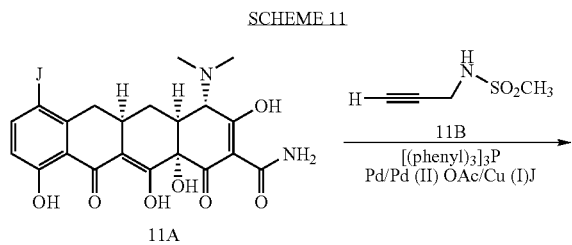

To a mixture of 7-iodosancycline mono trifluoroacetic acid salt (1 g; 1.53 mmoles, 11A), palladium II acetate(17.2 mg; 0.076 mmoles), tetrakis triphenylphosphine palladium (176.8 mg; 0.153 mmoles), and copper (I) iodide(49 mg; 0,228 mmoles) was added 15 ml of reagent grade acetonitrile in a clean dry 2 necked round bottom flask. The reaction was purged with a slow steam of argon gas, with stirring, for 5 minutes before the addition (in one portion as a solid) of N-methylsulphonamidopropargyl amine (11B). The sulphonamide was prepared by a method known in the art (J. Med. Chem 31(3) 1988; 577-82). This was followed by one milliliter of triethylamine (1 ml; 0.726 mg; 7.175 mmoles) and the reaction was stirred, under an argon atmosphere, for approximately 1.0 hour at ambient temperature. The reaction mixture was suctioned filtered through a pad of diatomaceous earth and washed with acetonitrile. The filtrates were reduced to dryness under vacuo and the residue was treated with a dilute solution of trifluroroacetic acid in acetonitrile to adjust the pH to approximately 2. The residue was treated with more dilute trifluoroacetic acid in acetonitrile, resulting in the formation of a precipitate, which was removed via suction filtration. The crude filtrates were purified utilizing reverse phase HPLC with DVB as the solid phase; and a gradient of 1:1 methanol/ acetonitrile 1% trifluoroacetic acid and 1% trifluoroacetic acid in water. The appropriate fractions were reduced to dryness under reduced pressure and solid collected. The product (11C) was characterized via $^1$H NMR, mass spectrogram and LC reverse phase.

Compound BK (7-(2'-methoxy-5'-formylphenyl) sancycline)

SCHEME 12

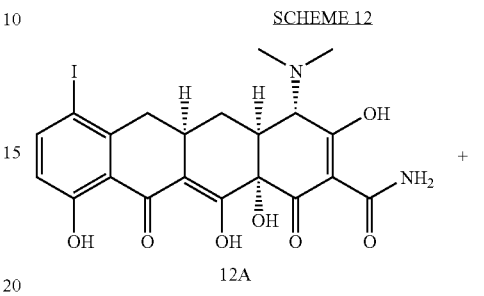

7-iodo-sancycline (12A, 1 g, 1.53 mmol), Pd(OAc)$_2$ (34 mg, 0.153 mmol), and MeOH (50 mL) were combined in a 250 mL 2 neck round bottom flask equipped with a condenser and argon line. The solution was then purged with argon (15 min) while heated in an oil bath to approximately 70° C. Sodium carbonate (482 mg, 4.58 mmol) was dissolved in water (3-5 mL) and added to reaction flask. The flask was then purged with argon for another 5 minutes. 2-Methoxy-5-formylphenyl boronic acid (12B, 333 mg, 1.83 mmol) was dissolved in MeOH (5 mL) and added to reaction flask. The flask was then purged again with argon for 10 minutes. The reaction was monitored to completion within 3 hours. The contents of the flask were filtered through filter paper and the remaining solvent was evacuated. To make the hydrochloric acid salt, the residue was dissolved in MeOH (sat. HCl) to make the HCl salt. The solution was then filtered and the solvent was evacuated. The product (12C) was then characterized by ¹H NMR, LC-MS.

Compound FD (7-(2'-Methoxy-5'-N,N'-Dimethylaminomethylphenyl)Sancycline)

SCHEME 13

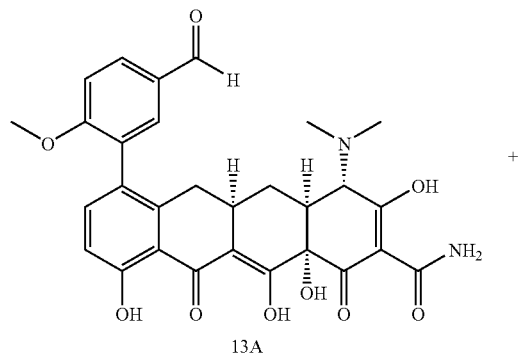

13A

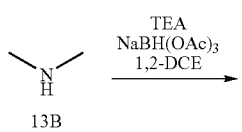

13B

TEA
NaBH(OAc)₃
1,2-DCE

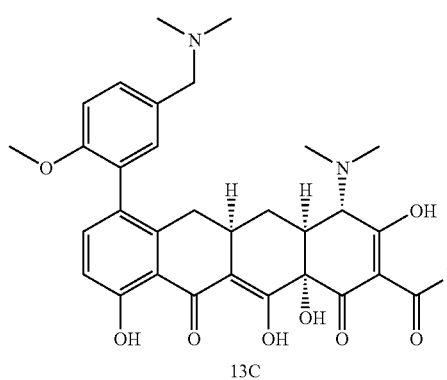

13C

The aldehyde (12A, 1 g, 1.82 mmol), dimethylamine HCl (13B, 297 mg, 3.64 mmol), triethylamine (506 µL, 3.64 mmol), and 1,2-DCE (7 mL) were combined in a 40 mL vial. The contents were dissolved within several minutes of shaking or stirring. Sodium triacetoxyborohydride (772 mg, 3.64 mmol) was then added as a solid. The reaction was monitored by HPLC and LC-MS and was complete within 3 hours. The reaction was quenched with MeOH (20 mL) and the solvent was subsequently evacuated. The residue was redissolved in 3 mL DMF and separated on a C-18 column. Fractions from the prep column dried down in-vacuo and the HCl salt was made by dissolving contents in methanol (sat. HCl). The solvent was reduced and a yellow powder formed (13C). Characterized by ¹H NMR, LC-MS, HPLC.

Example 2

In vitro Minimum Inhibitory Concentration (MIC) Assay

The following assay is used to determine the efficacy of the tetracycline compounds against common bacteria. 2 mg of each compound is dissolved in 100 µl of DMSO. The solution is then added to cation-adjusted Mueller Hinton broth (CAMHB), which results in a final compound concentration of 200 µg per ml. The tetracycline compound solutions are diluted to 50 µL volumes, with a test compound concentration of 0.098 µg/ml. Optical density (OD) determinations are made from fresh log-phase broth cultures of the test strains. Dilutions are made to achieve a final cell density of 1×10⁶ CFU/ml. At OD=1, cell densities for different genera should be approximately:

| | | |
|---|---|---|
| E. coli | 1 × 10⁹ CFU/ml |
| S. aureus | 5 × 10⁸ CFU/ml |
| Enterococcus sp. | 2.5 × 10⁹ CFU/ml |

50 µl of the cell suspensions are added to each well of microtiter plates. The final cell density should be approximately 5×10⁵ CFU/ml. These plates are incubated at 35° C. in an ambient air incubator for approximately 18 hr. The plates are read with a microplate reader and are visually inspected when necessary. The MIC is defined as the lowest concentration of the tetracycline compound that inhibits growth. Compounds of the invention indicate good inhibition of growth.

In Table 2, compounds which were good inhibitors of growth of a particular bacteria are indicated with *, compounds which were very good inhibitors of a particular bacteria are indicated with , and compounds with were particularly good inhibitors of a particular bacteria are indicated with *.

Equivalents

Those skilled in the art will recognize, or be able to ascertain using no more than routine experimentation, numerous equivalents to the specific procedures described herein. Such equivalents are considered to be within the scope of the present invention and are covered by the following claims. The contents of all references, patents, and patent applications cited throughout this application are hereby incorporated by reference. The appropriate components, processes, and methods of those patents, applications and other documents may be selected for the present invention and embodiments thereof.

| ID | STRUCTURE | S. aureus | E. hirae | E. coli |
|---|---|---|---|---|
| A | 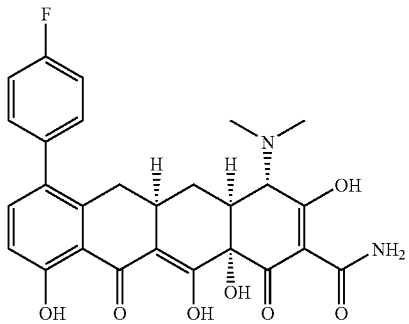 [SMILES: CN(C)[C@@H]1C(O)=C(C(N)=O)C(=O)[C@@]2(O)C(O)=C3C(=O)c4c(O)ccc(-c5ccc(F)cc5)c4C[C@H]3C[C@@H]12] | * | * | NT |
| B | 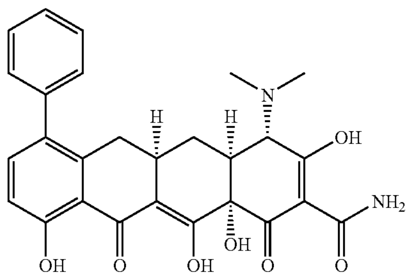 [SMILES: CN(C)[C@@H]1C(O)=C(C(N)=O)C(=O)[C@@]2(O)C(O)=C3C(=O)c4c(O)ccc(-c5ccccc5)c4C[C@H]3C[C@@H]12] |  |  | NT |
| C | 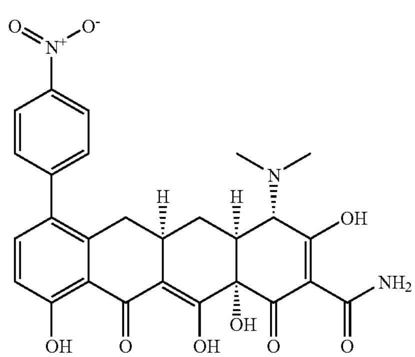 [SMILES: CN(C)[C@@H]1C(O)=C(C(N)=O)C(=O)[C@@]2(O)C(O)=C3C(=O)c4c(O)ccc(-c5ccc([N+](=O)[O-])cc5)c4C[C@H]3C[C@@H]12] |  |  | NT |
| D | 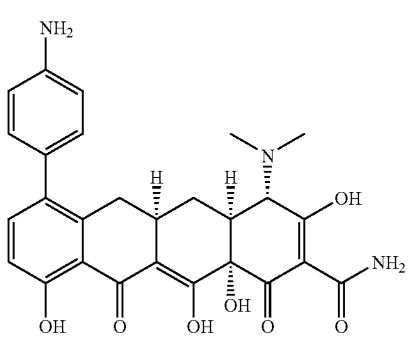 [SMILES: CN(C)[C@@H]1C(O)=C(C(N)=O)C(=O)[C@@]2(O)C(O)=C3C(=O)c4c(O)ccc(-c5ccc(N)cc5)c4C[C@H]3C[C@@H]12] | * | * | NT |

-continued

| ID | STRUCTURE | S. aureus | E. hirae | E. coli |
|---|---|---|---|---|
| E | [structure: 7-(4-chlorophenyl) tetracycline analog] | ** | ** | NT |
| F | [structure: 7-(3-nitrophenyl) tetracycline analog] | *** | *** | ** |
| G | [structure: 7-(4-(3-nitrophenyl)thiazol-2-ylamino) tetracycline analog] | NT | NT | NT |
| H | [structure: 7-(4-(methoxycarbonyl)phenyl) tetracycline analog] | *** | *** | * |

-continued

| ID | STRUCTURE | S. aureus | E. hirae | E. coli |
|---|---|---|---|---|
| I | 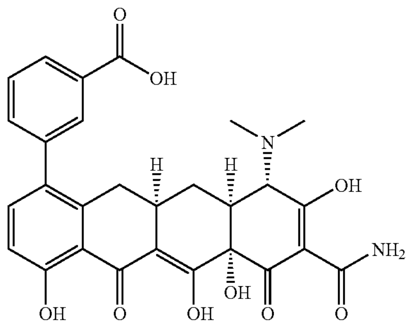 [SMILES: CN(C)[C@@H]1C(O)=C(C(N)=O)C(=O)[C@@]2(O)C(O)=C3C(=O)c4c(O)ccc(-c5cccc(C(=O)O)c5)c4C[C@H]3C[C@@H]12] | * | * | NT |
| J | 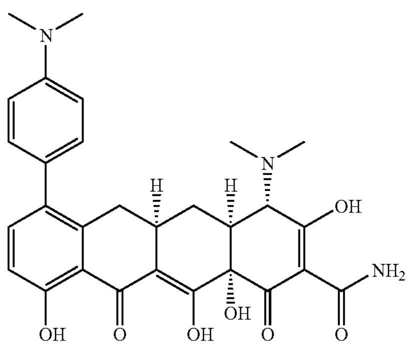 [SMILES: CN(C)c1ccc(-c2ccc(O)c3c2C[C@H]2C[C@H]4[C@H](N(C)C)C(O)=C(C(N)=O)C(=O)[C@@]4(O)C(O)=C2C3=O)cc1] | * | * | * |
| K | 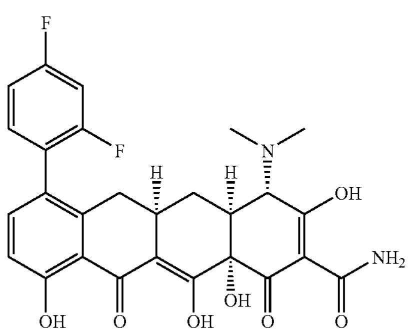 [SMILES: CN(C)[C@@H]1C(O)=C(C(N)=O)C(=O)[C@@]2(O)C(O)=C3C(=O)c4c(O)ccc(-c5ccc(F)cc5F)c4C[C@H]3C[C@@H]12] | * | * | ** |
| L | 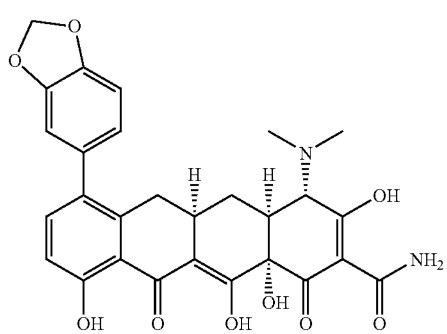 [SMILES: CN(C)[C@@H]1C(O)=C(C(N)=O)C(=O)[C@@]2(O)C(O)=C3C(=O)c4c(O)ccc(-c5ccc6c(c5)OCO6)c4C[C@H]3C[C@@H]12] | * |  | ** |

| ID | STRUCTURE | S. aureus | E. hirae | E. coli |
|---|---|---|---|---|
| M | 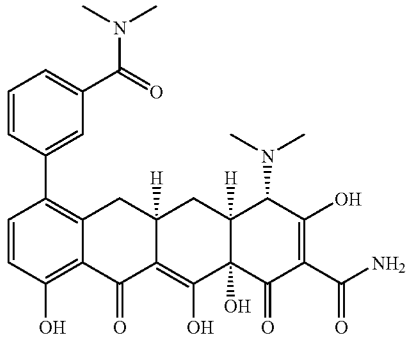 [SMILES: CN(C)C(=O)c1cccc(-c2ccc(O)c3c2C[C@H]2C[C@H]4[C@H](N(C)C)C(O)=C(C(N)=O)C(=O)[C@@]4(O)C(O)=C2C3=O)c1] |  | * | * |
| N | 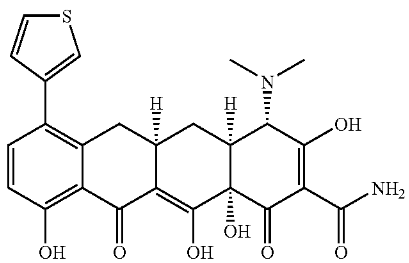 [SMILES: CN(C)[C@@H]1C(O)=C(C(N)=O)C(=O)[C@@]2(O)C(O)=C3C(=O)c4c(O)ccc(-c5ccsc5)c4C[C@H]3C[C@@H]12] | NT | NT | NT |
| O | 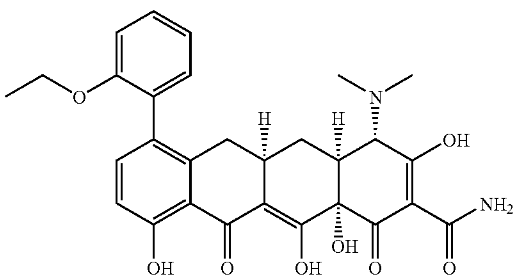 [SMILES: CCOc1ccccc1-c1ccc(O)c2c1C[C@H]1C[C@H]3[C@H](N(C)C)C(O)=C(C(N)=O)C(=O)[C@@]3(O)C(O)=C1C2=O] |  |  | ** |
| P | 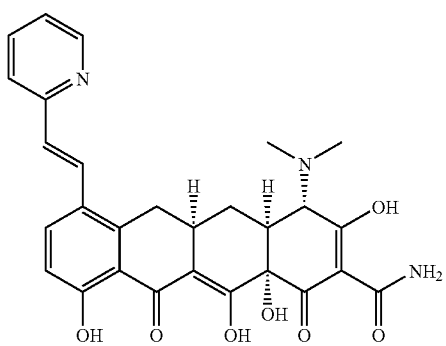 [SMILES: CN(C)[C@@H]1C(O)=C(C(N)=O)C(=O)[C@@]2(O)C(O)=C3C(=O)c4c(O)ccc(/C=C/c5ccccn5)c4C[C@H]3C[C@@H]12] |  |  | ** |
| Q | 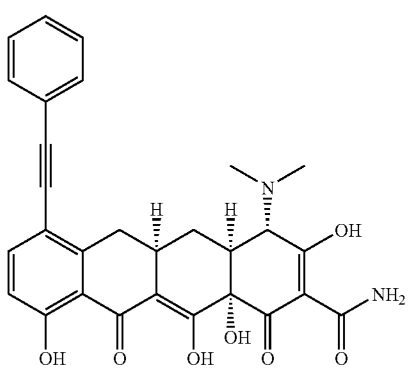 [SMILES: CN(C)[C@@H]1C(O)=C(C(N)=O)C(=O)[C@@]2(O)C(O)=C3C(=O)c4c(O)ccc(C#Cc5ccccc5)c4C[C@H]3C[C@@H]12] | * | * | * |

| ID | STRUCTURE | S. aureus | E. hirae | E. coli |
|---|---|---|---|---|
| R | 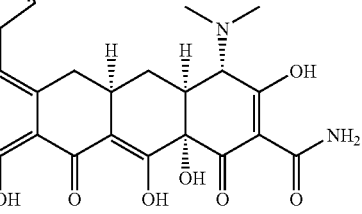 | * | * | ** |
| S | 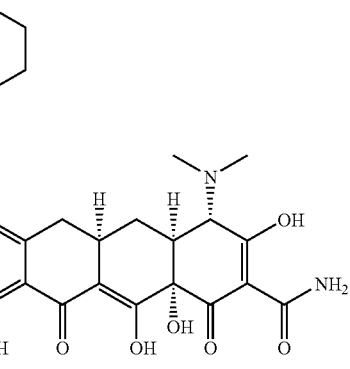 | * | ** | * |
| T | 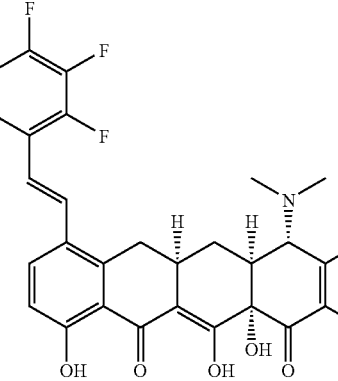 | * | ** | * |
| U | 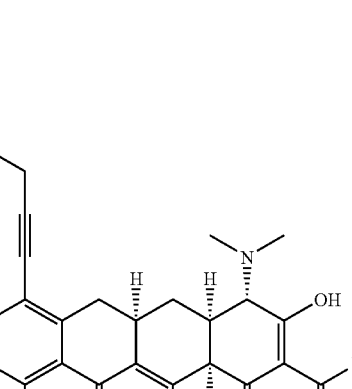 |  |  | *** |

-continued
| ID | STRUCTURE | S. aureus | E. hirae | E. coli |
|---|---|---|---|---|
| V | 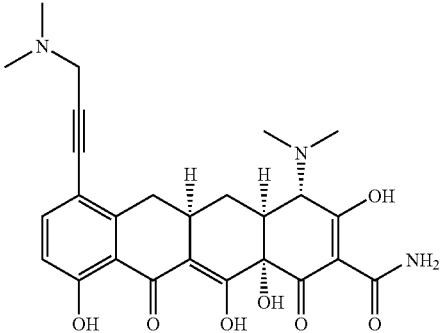 [SMILES: CN(C)CC#Cc1ccc(O)c2c1C[C@H]1C[C@H]3[C@H](N(C)C)C(O)=C(C(N)=O)C(=O)[C@@]3(O)C(O)=C1C2=O] |  | NT | * |
| W | 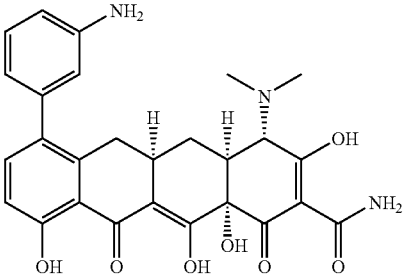 [SMILES: CN(C)[C@@H]1C(O)=C(C(N)=O)C(=O)[C@@]2(O)C(O)=C3C(=O)c4c(O)ccc(-c5cccc(N)c5)c4C[C@H]3C[C@@H]12] |  | * | ** |
| X | 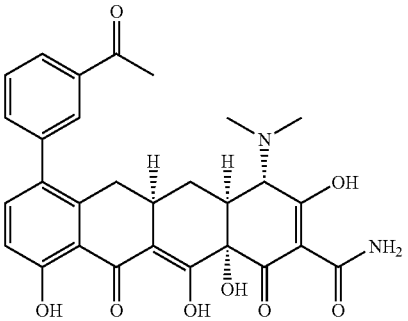 [SMILES: CC(=O)c1cccc(-c2ccc(O)c3c2C[C@H]2C[C@H]4[C@H](N(C)C)C(O)=C(C(N)=O)C(=O)[C@@]4(O)C(O)=C2C3=O)c1] | * | * | ** |
| Y | 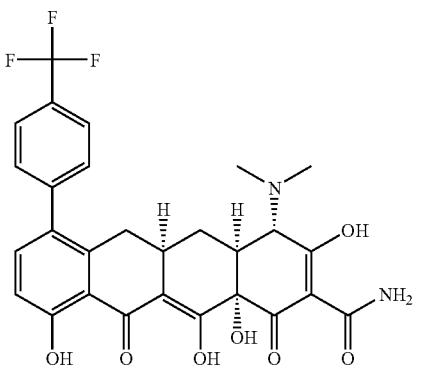 [SMILES: CN(C)[C@@H]1C(O)=C(C(N)=O)C(=O)[C@@]2(O)C(O)=C3C(=O)c4c(O)ccc(-c5ccc(C(F)(F)F)cc5)c4C[C@H]3C[C@@H]12] | * | * | ** |

-continued

| ID | STRUCTURE | S. aureus | E. hirae | E. coli |
|---|---|---|---|---|
| Z | 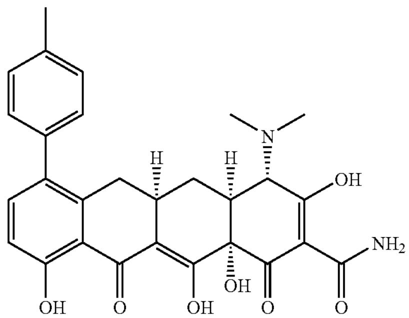 [SMILES: Cc1ccc(-c2ccc(O)c3c2C[C@H]2C[C@H]4[C@H](N(C)C)C(O)=C(C(N)=O)C(=O)[C@@]4(O)C(O)=C2C3=O)cc1] | * | * | * |
| AA | 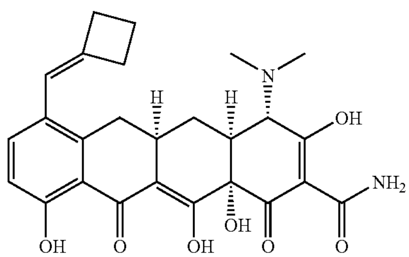 [SMILES: CN(C)[C@@H]1C(O)=C(C(N)=O)C(=O)[C@@]2(O)C(O)=C3C(=O)c4c(O)ccc(C=C5CCC5)c4C[C@H]3C[C@@H]12] | * | * | * |
| AB | 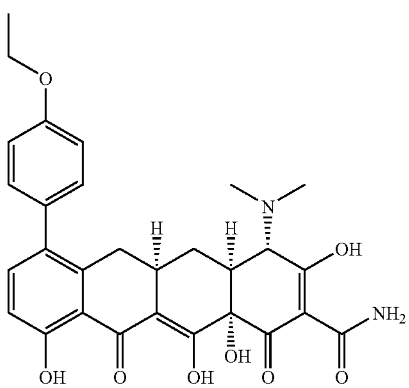 [SMILES: CCOc1ccc(-c2ccc(O)c3c2C[C@H]2C[C@H]4[C@H](N(C)C)C(O)=C(C(N)=O)C(=O)[C@@]4(O)C(O)=C2C3=O)cc1] | * | * | * |
| AC | 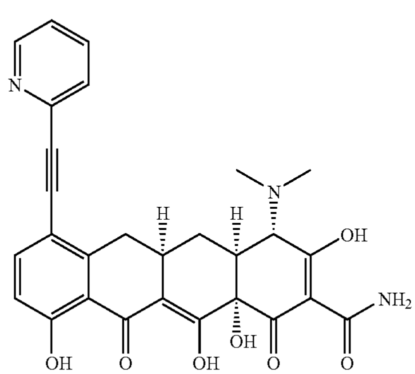 [SMILES: CN(C)[C@@H]1C(O)=C(C(N)=O)C(=O)[C@@]2(O)C(O)=C3C(=O)c4c(O)ccc(C#Cc5ccccn5)c4C[C@H]3C[C@@H]12] |  | * | ** |

| ID | STRUCTURE | S. aureus | E. hirae | E. coli |
|---|---|---|---|---|
| AD | 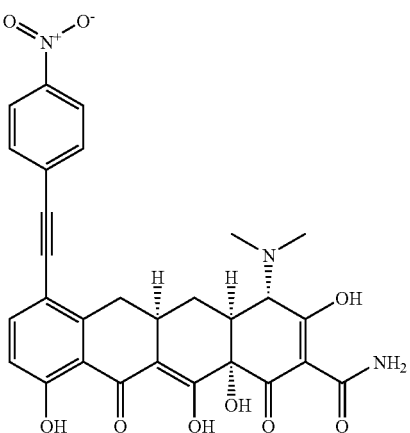 [SMILES: CN(C)[C@@H]1C(O)=C(C(N)=O)C(=O)[C@@]2(O)C(O)=C3C(=O)c4c(O)ccc(C#Cc5ccc([N+](=O)[O-])cc5)c4C[C@H]3C[C@@H]12] |  | * | * |
| AE | 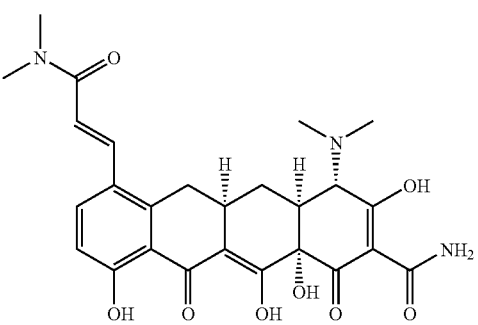 [SMILES: CN(C)C(=O)/C=C/c1ccc(O)c2c1C[C@H]1C[C@H]3[C@H](N(C)C)C(O)=C(C(N)=O)C(=O)[C@@]3(O)C(O)=C1C2=O] |  |  | ** |
| AF | 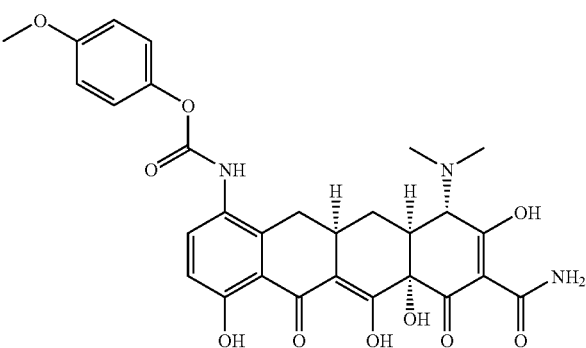 [SMILES: COc1ccc(OC(=O)Nc2ccc(O)c3c2C[C@H]2C[C@H]4[C@H](N(C)C)C(O)=C(C(N)=O)C(=O)[C@@]4(O)C(O)=C2C3=O)cc1] | NT | NT | NT |
| AG | 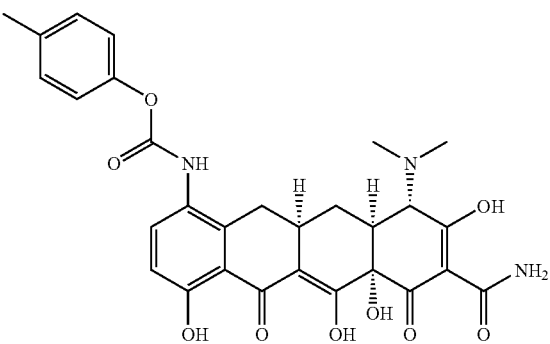 [SMILES: Cc1ccc(OC(=O)Nc2ccc(O)c3c2C[C@H]2C[C@H]4[C@H](N(C)C)C(O)=C(C(N)=O)C(=O)[C@@]4(O)C(O)=C2C3=O)cc1] | NT | NT | NT |

-continued

| ID | STRUCTURE | S. aureus | E. hirae | E. coli |
|---|---|---|---|---|
| AH | 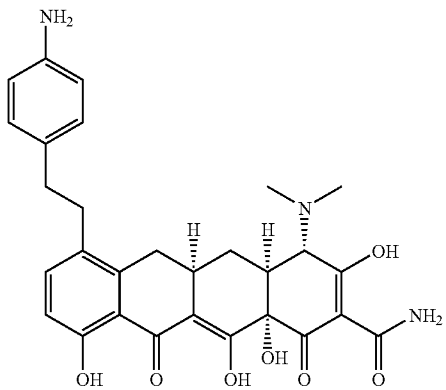 [SMILES: CN(C)[C@@H]1C(O)=C(C(N)=O)C(=O)[C@@]2(O)C(O)=C3C(=O)c4c(O)ccc(CCc5ccc(N)cc5)c4C[C@H]3C[C@@H]12] |  |  | * |
| AI | 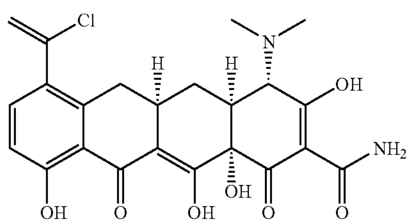 [SMILES: C=C(Cl)c1ccc(O)c2c1C[C@H]1C[C@H]3[C@H](N(C)C)C(O)=C(C(N)=O)C(=O)[C@@]3(O)C(O)=C1C2=O] |  |  | ** |
| AJ | 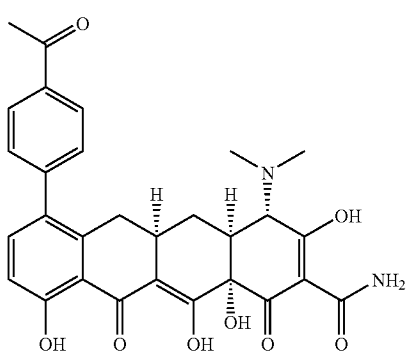 [SMILES: CC(=O)c1ccc(-c2ccc(O)c3c2C[C@H]2C[C@H]4[C@H](N(C)C)C(O)=C(C(N)=O)C(=O)[C@@]4(O)C(O)=C2C3=O)cc1] | * | * | *** |
| AK | 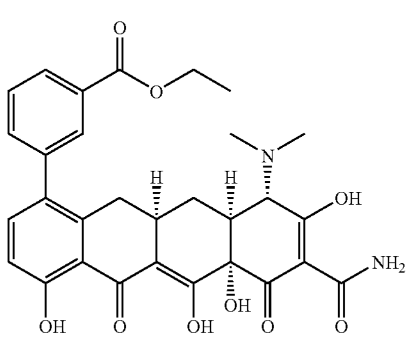 [SMILES: CCOC(=O)c1cccc(-c2ccc(O)c3c2C[C@H]2C[C@H]4[C@H](N(C)C)C(O)=C(C(N)=O)C(=O)[C@@]4(O)C(O)=C2C3=O)c1] | * | * | * |

| ID | STRUCTURE | S. aureus | E. hirae | E. coli |
|---|---|---|---|---|
| AL | 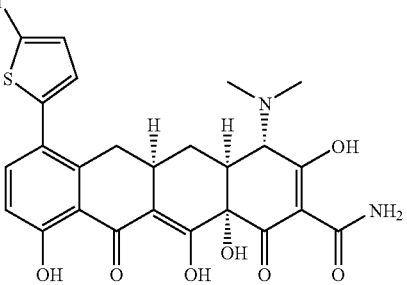 | NT | NT | NT |
| AM | 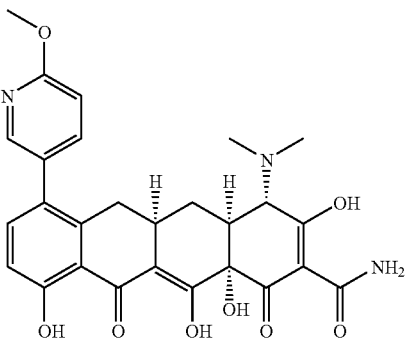 [SMILES: COc1ccc(-c2ccc(O)c3c2C[C@H]2C[C@H]4[C@H](N(C)C)C(O)=C(C(N)=O)C(=O)[C@@]4(O)C(O)=C2C3=O)cn1] | NT | NT | NT |
| AN | 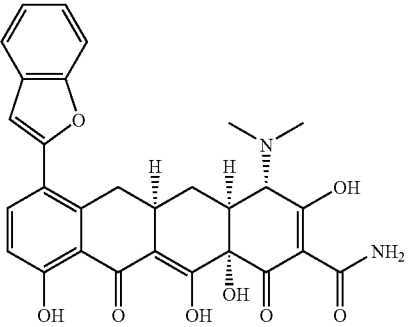 [SMILES: CN(C)[C@@H]1C(O)=C(C(N)=O)C(=O)[C@@]2(O)C(O)=C3C(=O)c4c(O)ccc(-c5cc6ccccc6o5)c4C[C@H]3C[C@@H]12] | NT | NT | NT |
| AO | 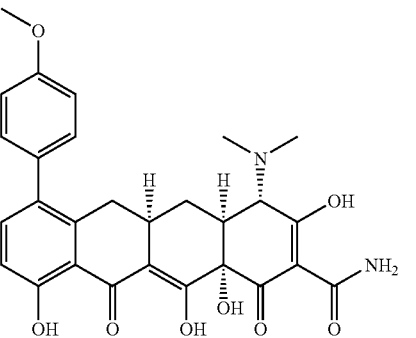 [SMILES: COc1ccc(-c2ccc(O)c3c2C[C@H]2C[C@H]4[C@H](N(C)C)C(O)=C(C(N)=O)C(=O)[C@@]4(O)C(O)=C2C3=O)cc1] | * | * | * |

-continued

| ID | STRUCTURE | S. aureus | E. hirae | E. coli |
|---|---|---|---|---|
| AP | 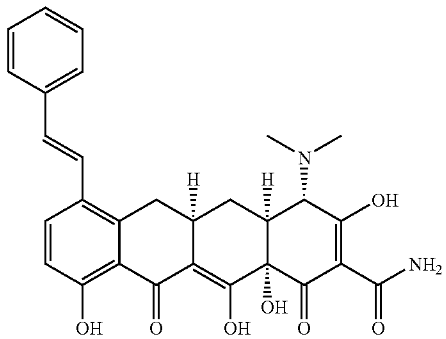 [SMILES: CN(C)[C@@H]1C(O)=C(C(N)=O)C(=O)[C@@]2(O)C(O)=C3C(=O)c4c(O)ccc(/C=C/c5ccccc5)c4C[C@H]3C[C@@H]12] | * | * | * |
| AQ | 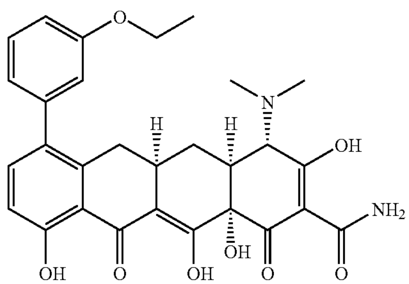 [SMILES: CCOc1cccc(-c2ccc(O)c3c2C[C@H]2C[C@H]4[C@H](N(C)C)C(O)=C(C(N)=O)C(=O)[C@@]4(O)C(O)=C2C3=O)c1] | * | * | * |
| AR | 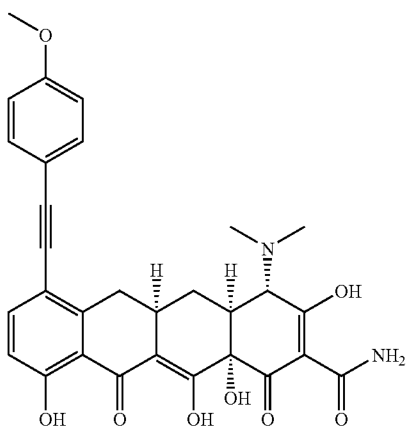 [SMILES: COc1ccc(C#Cc2ccc(O)c3c2C[C@H]2C[C@H]4[C@H](N(C)C)C(O)=C(C(N)=O)C(=O)[C@@]4(O)C(O)=C2C3=O)cc1] | * | * | * |
| AS | 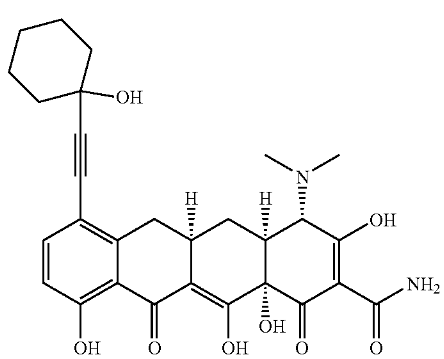 [SMILES: CN(C)[C@@H]1C(O)=C(C(N)=O)C(=O)[C@@]2(O)C(O)=C3C(=O)c4c(O)ccc(C#CC5(O)CCCCC5)c4C[C@H]3C[C@@H]12] | * | * | ** |

| ID | STRUCTURE | S. aureus | E. hirae | E. coli |
|---|---|---|---|---|
| AT | 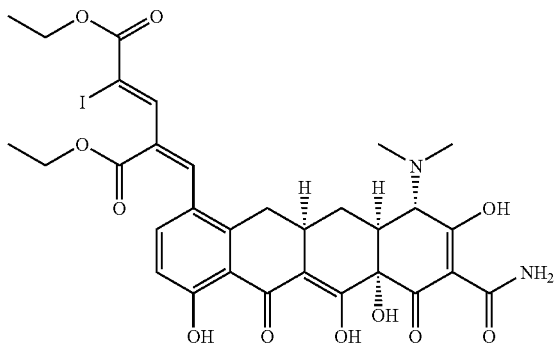 [SMILES: CCOC(=O)/C(I)=C/C(=C/c1ccc(O)c2c1C[C@H]1C[C@H]3[C@H](N(C)C)C(O)=C(C(N)=O)C(=O)[C@@]3(O)C(O)=C1C2=O)C(=O)OCC] | * | * | * |
| AU | 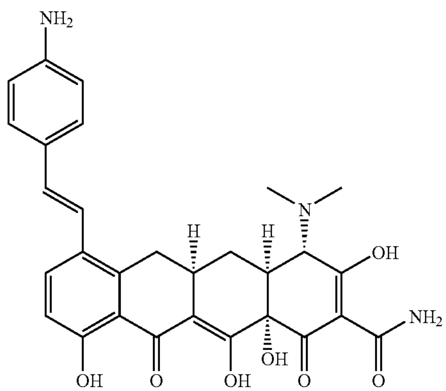 [SMILES: CN(C)[C@@H]1C(O)=C(C(N)=O)C(=O)[C@@]2(O)C(O)=C3C(=O)c4c(O)ccc(/C=C/c5ccc(N)cc5)c4C[C@H]3C[C@@H]12] |  |  | * |
| AV | 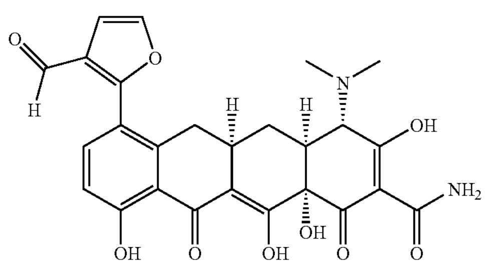 [SMILES: CN(C)[C@@H]1C(O)=C(C(N)=O)C(=O)[C@@]2(O)C(O)=C3C(=O)c4c(O)ccc(-c5occc5C=O)c4C[C@H]3C[C@@H]12] | NT | NT | NT |
| AW | 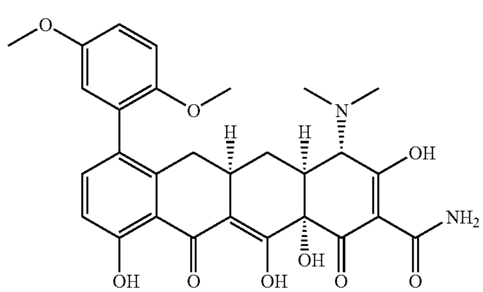 [SMILES: COc1ccc(OC)c(-c2ccc(O)c3c2C[C@H]2C[C@H]4[C@H](N(C)C)C(O)=C(C(N)=O)C(=O)[C@@]4(O)C(O)=C2C3=O)c1] | * |  | * |
| AX | 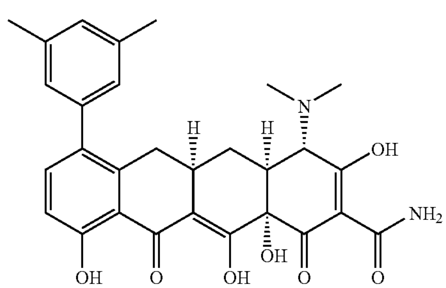 [SMILES: Cc1cc(C)cc(-c2ccc(O)c3c2C[C@H]2C[C@H]4[C@H](N(C)C)C(O)=C(C(N)=O)C(=O)[C@@]4(O)C(O)=C2C3=O)c1] | * |  | * |

-continued

| ID | STRUCTURE | S. aureus | E. hirae | E. coli |
|---|---|---|---|---|
| AY | 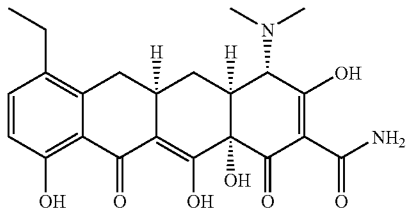 [SMILES: CCc1ccc(O)c2c1C[C@H]1C[C@H]3[C@H](N(C)C)C(O)=C(C(N)=O)C(=O)[C@@]3(O)C(O)=C1C2=O] |  |  | *** |
| AZ | 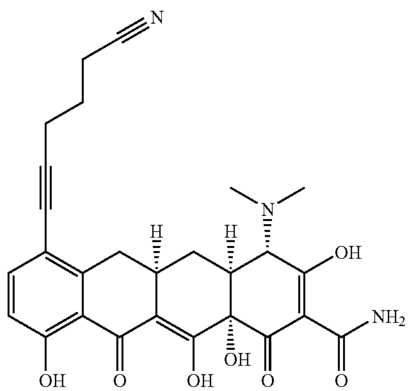 [SMILES: CN(C)[C@@H]1C(O)=C(C(N)=O)C(=O)[C@@]2(O)C(O)=C3C(=O)c4c(O)ccc(C#CCCCC#N)c4C[C@H]3C[C@@H]12] | * |  | ** |
| BA | 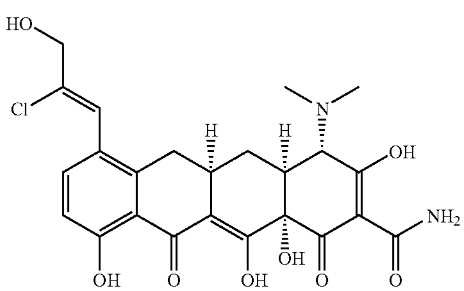 [SMILES: CN(C)[C@@H]1C(O)=C(C(N)=O)C(=O)[C@@]2(O)C(O)=C3C(=O)c4c(O)ccc(/C=C(\Cl)CO)c4C[C@H]3C[C@@H]12] | * |  |  |
| BB | 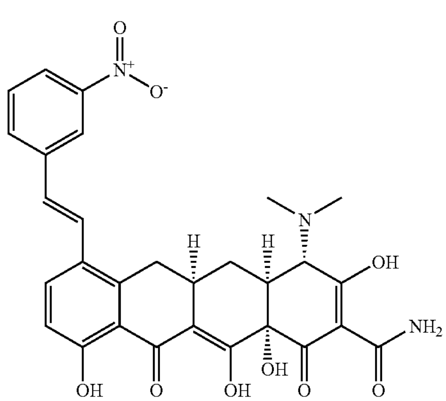 [SMILES: CN(C)[C@@H]1C(O)=C(C(N)=O)C(=O)[C@@]2(O)C(O)=C3C(=O)c4c(O)ccc(/C=C/c5cccc([N+](=O)[O-])c5)c4C[C@H]3C[C@@H]12] |  |  | ** |

-continued
| ID | STRUCTURE | S. aureus | E. hirae | E. coli |
|---|---|---|---|---|
| BC | 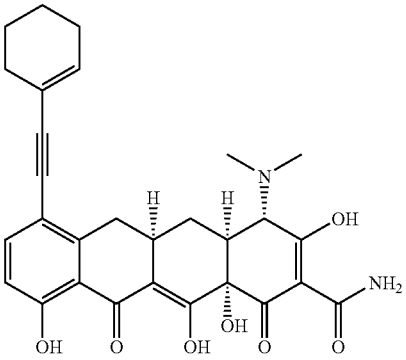 | * | * | * |
| BD | 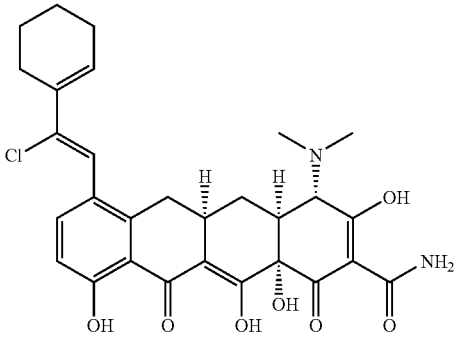 [SMILES: CN(C)[C@@H]1C(O)=C(C(N)=O)C(=O)[C@@]2(O)C(O)=C3C(=O)c4c(O)ccc(/C=C(\Cl)C5=CCCCC5)c4C[C@H]3C[C@@H]12] |  |  | ** |
| BE | 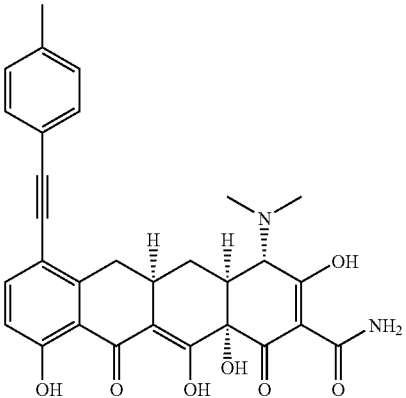 [SMILES: Cc1ccc(C#Cc2ccc(O)c3c2C[C@H]2C[C@H]4[C@H](N(C)C)C(O)=C(C(N)=O)C(=O)[C@@]4(O)C(O)=C2C3=O)cc1] |  | * | * |
| BF | 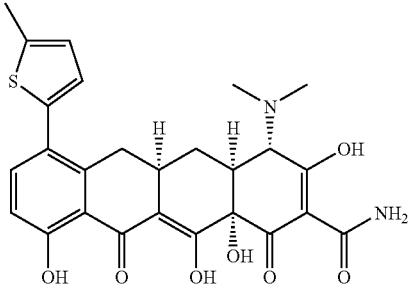 [SMILES: Cc1ccc(-c2ccc(O)c3c2C[C@H]2C[C@H]4[C@H](N(C)C)C(O)=C(C(N)=O)C(=O)[C@@]4(O)C(O)=C2C3=O)s1] | NT | NT | NT |

| ID | STRUCTURE | S. aureus | E. hirae | E. coli |
|---|---|---|---|---|
| BG | 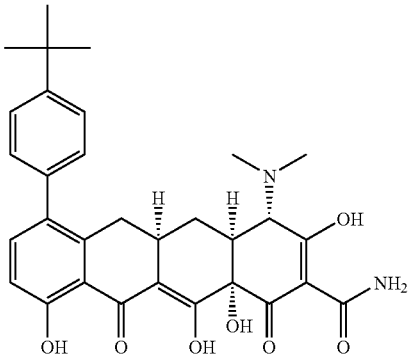 [SMILES: CN(C)[C@@H]1C(O)=C(C(N)=O)C(=O)[C@@]2(O)C(O)=C3C(=O)c4c(O)ccc(-c5ccc(C(C)(C)C)cc5)c4C[C@H]3C[C@@H]12] |  |  | * |
| BH | 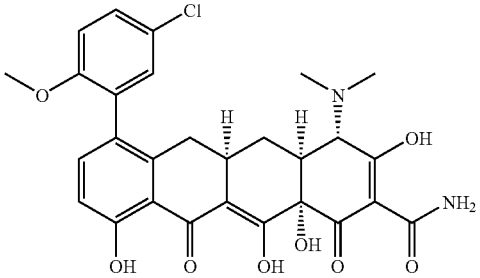 [SMILES: COc1ccc(Cl)cc1-c1ccc(O)c2c1C[C@H]1C[C@H]3[C@H](N(C)C)C(O)=C(C(N)=O)C(=O)[C@@]3(O)C(O)=C1C2=O] | * | * | * |
| BI | 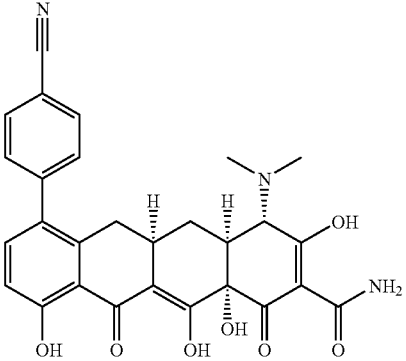 [SMILES: CN(C)[C@@H]1C(O)=C(C(N)=O)C(=O)[C@@]2(O)C(O)=C3C(=O)c4c(O)ccc(-c5ccc(C#N)cc5)c4C[C@H]3C[C@@H]12] | * | * | *** |
| BJ | 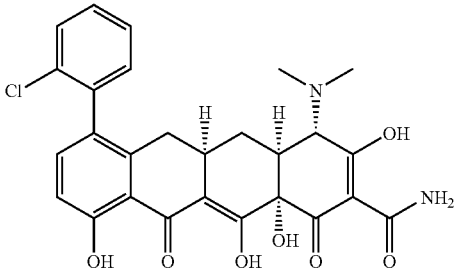 [SMILES: CN(C)[C@@H]1C(O)=C(C(N)=O)C(=O)[C@@]2(O)C(O)=C3C(=O)c4c(O)ccc(-c5ccccc5Cl)c4C[C@H]3C[C@@H]12] | * | * | * |

| ID | STRUCTURE | S. aureus | E. hirae | E. coli |
|---|---|---|---|---|
| BK | 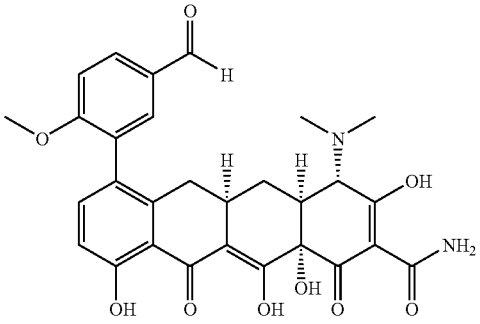 [SMILES: COc1ccc(C=O)cc1-c1ccc(O)c2c1C[C@H]1C[C@H]3[C@H](N(C)C)C(O)=C(C(N)=O)C(=O)[C@@]3(O)C(O)=C1C2=O] | * | * | *** |
| BL | 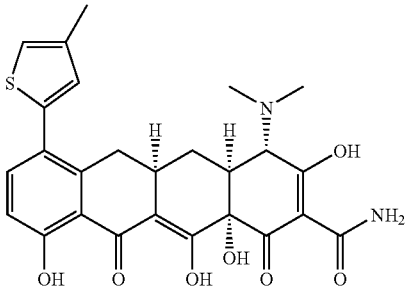 [SMILES: Cc1csc(-c2ccc(O)c3c2C[C@H]2C[C@H]4[C@H](N(C)C)C(O)=C(C(N)=O)C(=O)[C@@]4(O)C(O)=C2C3=O)c1] | NT | NT | NT |
| BM | 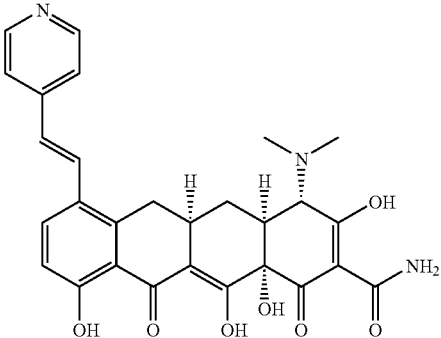 [SMILES: CN(C)[C@@H]1C(O)=C(C(N)=O)C(=O)[C@@]2(O)C(O)=C3C(=O)c4c(O)ccc(/C=C/c5ccncc5)c4C[C@H]3C[C@@H]12] |  |  | ** |
| BN | 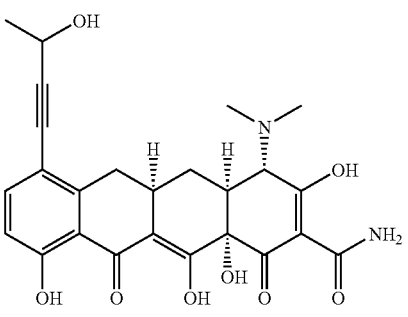 [SMILES: CC(O)C#Cc1ccc(O)c2c1C[C@H]1C[C@H]3[C@H](N(C)C)C(O)=C(C(N)=O)C(=O)[C@@]3(O)C(O)=C1C2=O] | ** | * | * |
| BO | 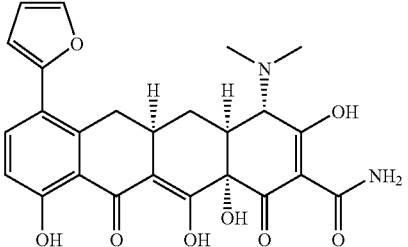 [SMILES: CN(C)[C@@H]1C(O)=C(C(N)=O)C(=O)[C@@]2(O)C(O)=C3C(=O)c4c(O)ccc(-c5ccco5)c4C[C@H]3C[C@@H]12] | NT | NT | NT |

| ID | STRUCTURE | S. aureus | E. hirae | E. coli |
|---|---|---|---|---|
| BP | 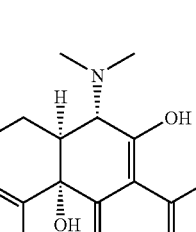 | NT | NT | NT |
| BQ | 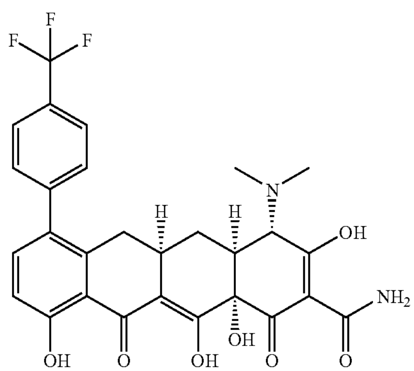 [SMILES: CN(C)[C@@H]1C(O)=C(C(N)=O)C(=O)[C@@]2(O)C(O)=C3C(=O)c4c(O)ccc(-c5ccc(C(F)(F)F)cc5)c4C[C@H]3C[C@@H]12] | NT | NT | NT |
| BR | 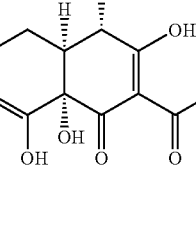 | NT | NT | NT |
| BS | 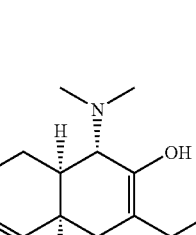 |  | * | * |

| ID | STRUCTURE | S. aureus | E. hirae | E. coli |
|---|---|---|---|---|
| BT | 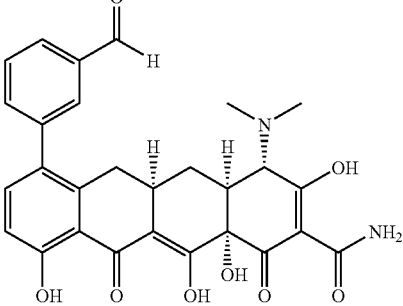 | * | * | *** |
| BU | 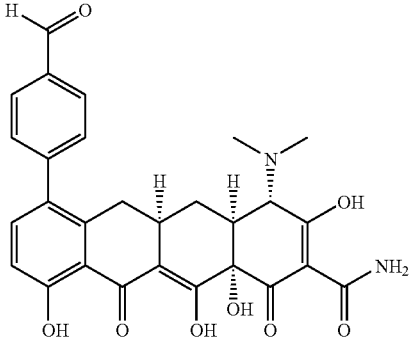 [SMILES: CN(C)[C@@H]1C(O)=C(C(N)=O)C(=O)[C@@]2(O)C(O)=C3C(=O)c4c(O)ccc(-c5ccc(C=O)cc5)c4C[C@H]3C[C@@H]12] | * |  | *** |
| BV | 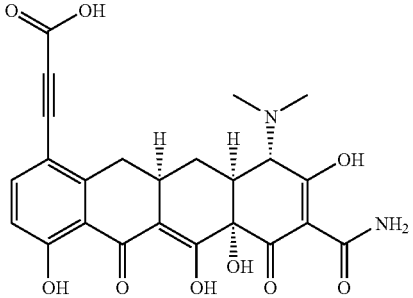 [SMILES: CN(C)[C@@H]1C(O)=C(C(N)=O)C(=O)[C@@]2(O)C(O)=C3C(=O)c4c(O)ccc(C#CC(=O)O)c4C[C@H]3C[C@@H]12] | * | * | * |
| BW | 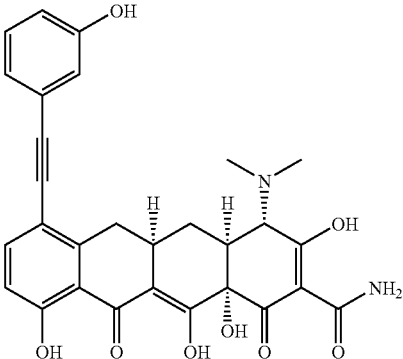 [SMILES: CN(C)[C@@H]1C(O)=C(C(N)=O)C(=O)[C@@]2(O)C(O)=C3C(=O)c4c(O)ccc(C#Cc5cccc(O)c5)c4C[C@H]3C[C@@H]12] |  | * | * |
| BX | 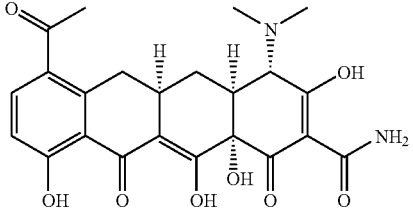 [SMILES: CC(=O)c1ccc(O)c2c1C[C@H]1C[C@H]3[C@H](N(C)C)C(O)=C(C(N)=O)C(=O)[C@@]3(O)C(O)=C1C2=O] |  |  | * |

| ID | STRUCTURE | S. aureus | E. hirae | E. coli |
|---|---|---|---|---|
| BY | 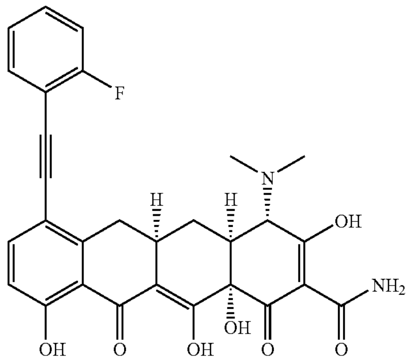 [SMILES: CN(C)[C@@H]1C(O)=C(C(N)=O)C(=O)[C@@]2(O)C(O)=C3C(=O)c4c(O)ccc(C#Cc5ccccc5F)c4C[C@H]3C[C@@H]12] | * | * | * |
| BZ | 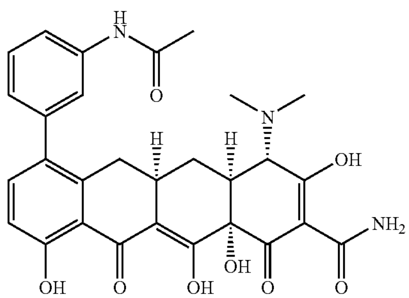 [SMILES: CC(=O)Nc1cccc(-c2ccc(O)c3c2C[C@H]2C[C@H]4[C@H](N(C)C)C(O)=C(C(N)=O)C(=O)[C@@]4(O)C(O)=C2C3=O)c1] |  |  | * |
| CA | 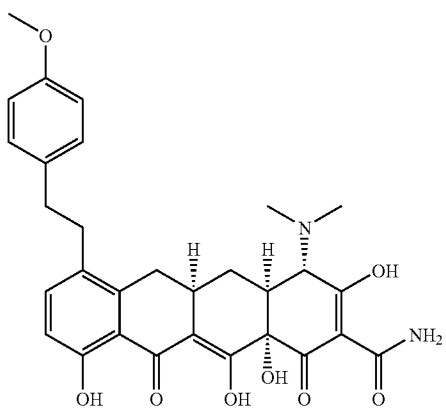 [SMILES: COc1ccc(CCc2ccc(O)c3c2C[C@H]2C[C@H]4[C@H](N(C)C)C(O)=C(C(N)=O)C(=O)[C@@]4(O)C(O)=C2C3=O)cc1] |  | * | * |
| CB | 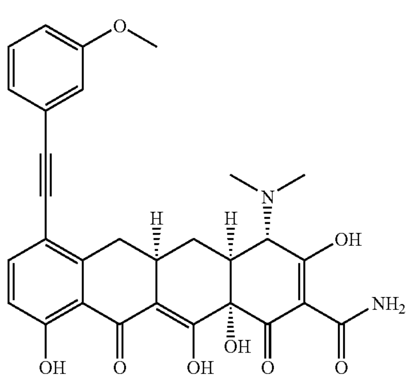 [SMILES: COc1cccc(C#Cc2ccc(O)c3c2C[C@H]2C[C@H]4[C@H](N(C)C)C(O)=C(C(N)=O)C(=O)[C@@]4(O)C(O)=C2C3=O)c1] |  | * | * |

| ID | STRUCTURE | S. aureus | E. hirae | E. coli |
|---|---|---|---|---|
| CC | 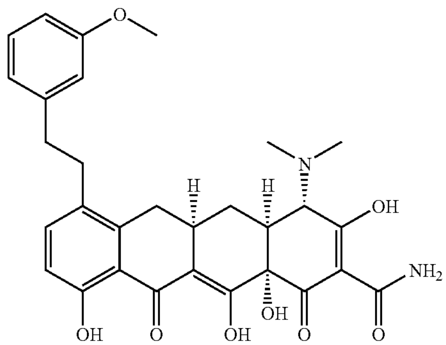 [SMILES: COc1cccc(CCc2ccc(O)c3c2C[C@H]2C[C@H]4[C@H](N(C)C)C(O)=C(C(N)=O)C(=O)[C@@]4(O)C(O)=C2C3=O)c1] |  |  | * |
| CD | 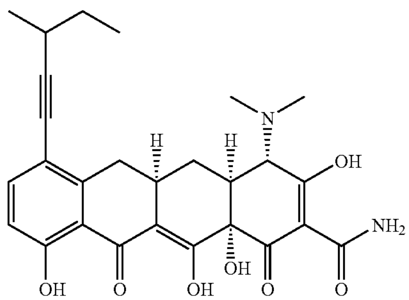 [SMILES: CCC(C)C#Cc1ccc(O)c2c1C[C@H]1C[C@H]3[C@H](N(C)C)C(O)=C(C(N)=O)C(=O)[C@@]3(O)C(O)=C1C2=O] |  | * | * |
| CE | 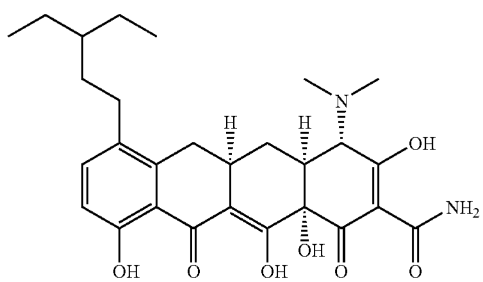 [SMILES: CCC(CC)CCc1ccc(O)c2c1C[C@H]1C[C@H]3[C@H](N(C)C)C(O)=C(C(N)=O)C(=O)[C@@]3(O)C(O)=C1C2=O] |  |  | * |
| CF | 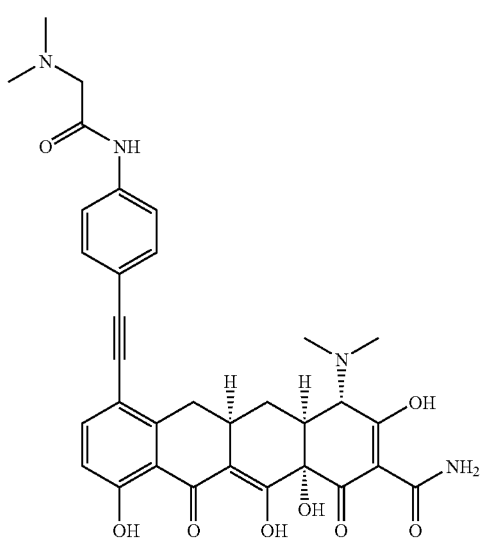 [SMILES: CN(C)CC(=O)Nc1ccc(C#Cc2ccc(O)c3c2C[C@H]2C[C@H]4[C@H](N(C)C)C(O)=C(C(N)=O)C(=O)[C@@]4(O)C(O)=C2C3=O)cc1] | * | * | *** |

-continued

| ID | STRUCTURE | S. aureus | E. hirae | E. coli |
|---|---|---|---|---|
| CG | 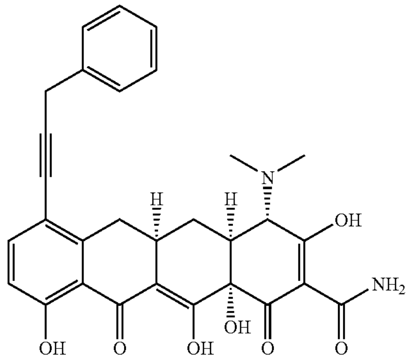 [SMILES: CN(C)[C@@H]1C(O)=C(C(N)=O)C(=O)[C@@]2(O)C(O)=C3C(=O)c4c(O)ccc(C#CCc5ccccc5)c4C[C@H]3C[C@@H]12] |  | * | * |
| CH | 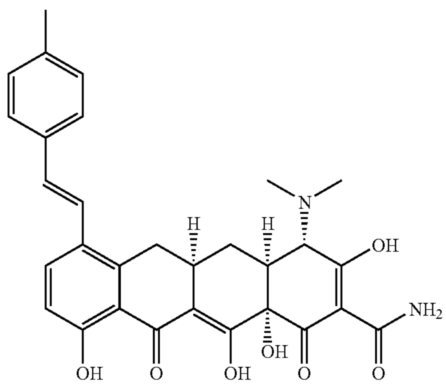 [SMILES: Cc1ccc(/C=C/c2ccc(O)c3c2C[C@H]2C[C@H]4[C@H](N(C)C)C(O)=C(C(N)=O)C(=O)[C@@]4(O)C(O)=C2C3=O)cc1] |  | * | ** |
| CI | 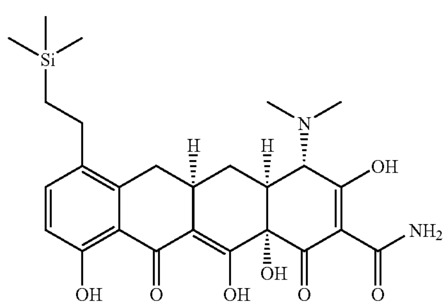 [SMILES: CN(C)[C@@H]1C(O)=C(C(N)=O)C(=O)[C@@]2(O)C(O)=C3C(=O)c4c(O)ccc(CC[Si](C)(C)C)c4C[C@H]3C[C@@H]12] |  |  | * |
| CJ | 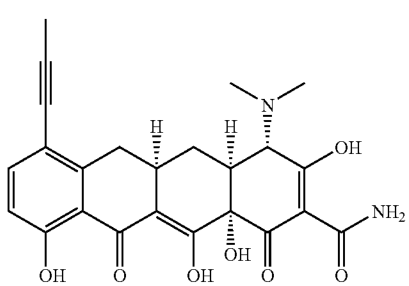 [SMILES: CC#Cc1ccc(O)c2c1C[C@H]1C[C@H]3[C@H](N(C)C)C(O)=C(C(N)=O)C(=O)[C@@]3(O)C(O)=C1C2=O] |  | * | ** |

-continued

| ID | STRUCTURE | S. aureus | E. hirae | E. coli |
|---|---|---|---|---|
| CK | 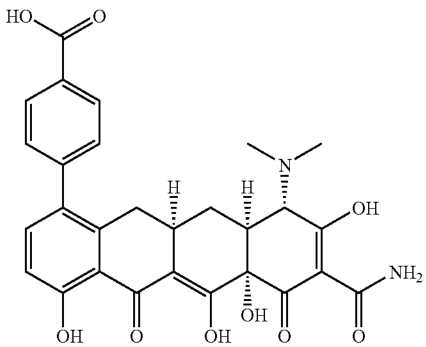 [SMILES: CN(C)[C@@H]1C(O)=C(C(N)=O)C(=O)[C@@]2(O)C(O)=C3C(=O)c4c(O)ccc(-c5ccc(C(=O)O)cc5)c4C[C@H]3C[C@@H]12] |  |  | * |
| CL | 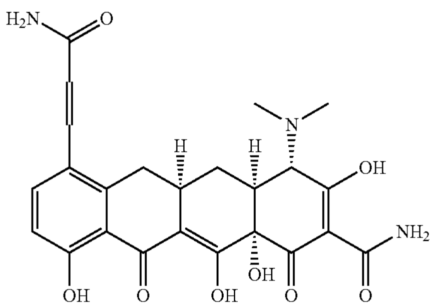 [SMILES: CN(C)[C@@H]1C(O)=C(C(N)=O)C(=O)[C@@]2(O)C(O)=C3C(=O)c4c(O)ccc(C=CC(N)=O)c4C[C@H]3C[C@@H]12] | * | * | * |
| CM | 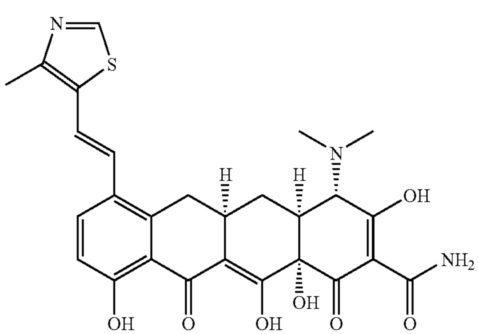 [SMILES: Cc1ncsc1/C=C/c1ccc(O)c2c1C[C@H]1C[C@H]3[C@H](N(C)C)C(O)=C(C(N)=O)C(=O)[C@@]3(O)C(O)=C1C2=O] |  |  | * |
| CN | 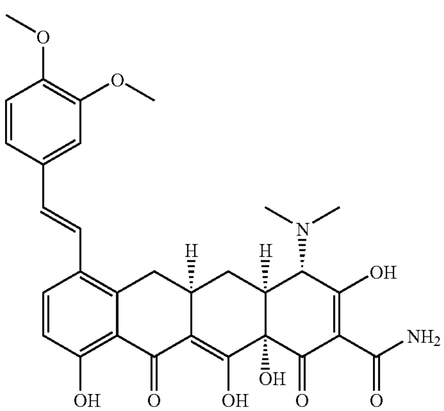 [SMILES: COc1ccc(/C=C/c2ccc(O)c3c2C[C@H]2C[C@H]4[C@H](N(C)C)C(O)=C(C(N)=O)C(=O)[C@@]4(O)C(O)=C2C3=O)cc1OC] | * | * | * |

-continued

| ID | STRUCTURE | S. aureus | E. hirae | E. coli |
|---|---|---|---|---|
| CO | 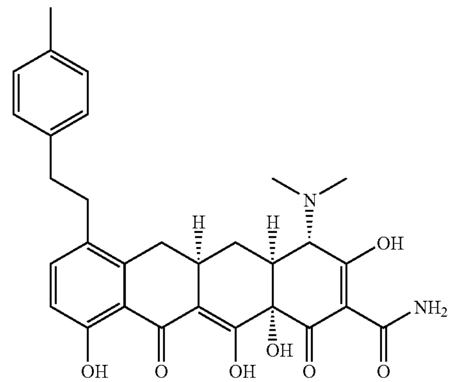 [SMILES: Cc1ccc(CCc2ccc(O)c3c2C[C@H]2C[C@H]4[C@H](N(C)C)C(O)=C(C(N)=O)C(=O)[C@@]4(O)C(O)=C2C3=O)cc1] |  |  | * |
| CP | 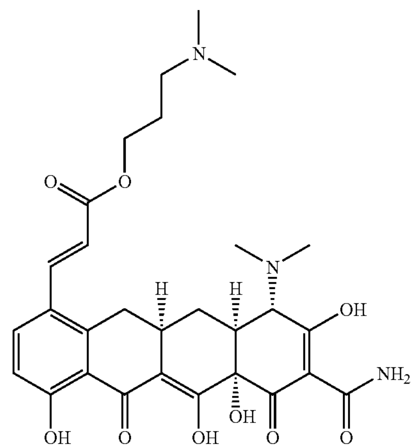 [SMILES: CN(C)CCCOC(=O)/C=C/c1ccc(O)c2c1C[C@H]1C[C@H]3[C@H](N(C)C)C(O)=C(C(N)=O)C(=O)[C@@]3(O)C(O)=C1C2=O] | * | * | * |
| CQ | 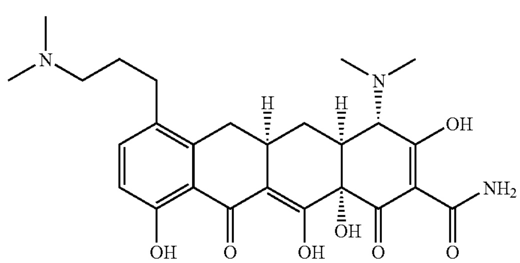 [SMILES: CN(C)CCCc1ccc(O)c2c1C[C@H]1C[C@H]3[C@H](N(C)C)C(O)=C(C(N)=O)C(=O)[C@@]3(O)C(O)=C1C2=O] | * | ** | * |
| CR | 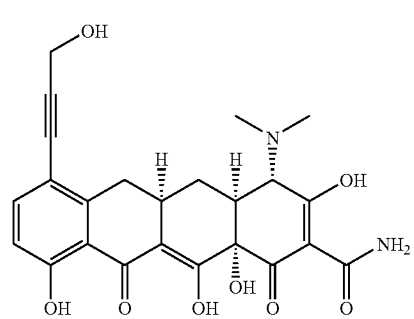 [SMILES: CN(C)[C@@H]1C(O)=C(C(N)=O)C(=O)[C@@]2(O)C(O)=C3C(=O)c4c(O)ccc(C#CCO)c4C[C@H]3C[C@@H]12] | ** | * | * |

| ID | STRUCTURE | S. aureus | E. hirae | E. coli |
|---|---|---|---|---|
| CS | 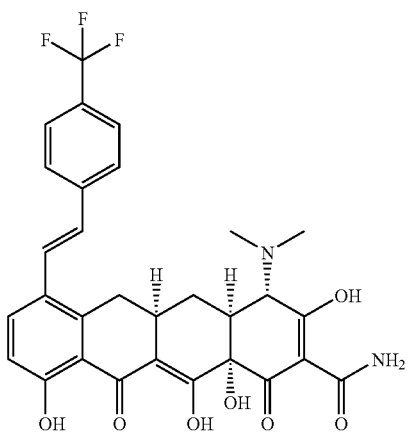 [SMILES: CN(C)[C@@H]1C(O)=C(C(N)=O)C(=O)[C@@]2(O)C(O)=C3C(=O)c4c(O)ccc(/C=C/c5ccc(C(F)(F)F)cc5)c4C[C@H]3C[C@@H]12] |  |  | * |
| CT | 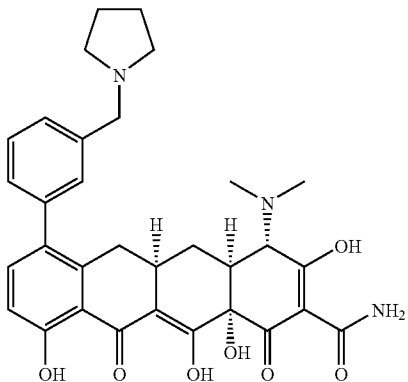 [SMILES: CN(C)[C@@H]1C(O)=C(C(N)=O)C(=O)[C@@]2(O)C(O)=C3C(=O)c4c(O)ccc(-c5cccc(CN6CCCC6)c5)c4C[C@H]3C[C@@H]12] |  |  | * |
| CU | 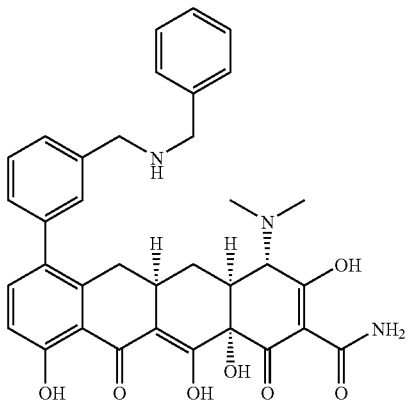 [SMILES: CN(C)[C@@H]1C(O)=C(C(N)=O)C(=O)[C@@]2(O)C(O)=C3C(=O)c4c(O)ccc(-c5cccc(CNCc6ccccc6)c5)c4C[C@H]3C[C@@H]12] |  |  | *** |

| ID | STRUCTURE | S. aureus | E. hirae | E. coli |
|---|---|---|---|---|
| CV | 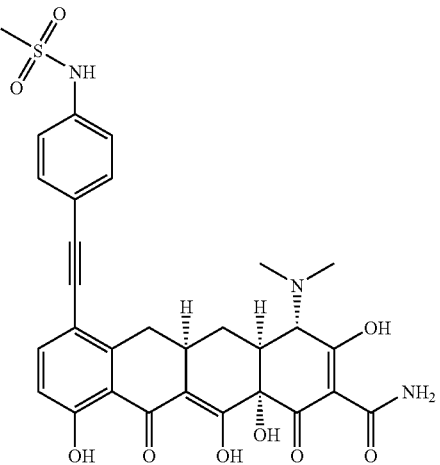 [SMILES: CN(C)[C@@H]1C(O)=C(C(N)=O)C(=O)[C@@]2(O)C(O)=C3C(=O)c4c(O)ccc(C#Cc5ccc(NS(C)(=O)=O)cc5)c4C[C@H]3C[C@@H]12] |  | * | * |
| CW | 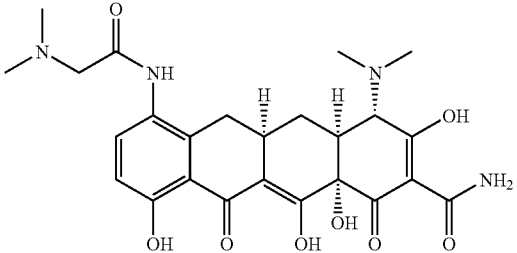 [SMILES: CN(C)CC(=O)Nc1ccc(O)c2c1C[C@H]1C[C@H]3[C@H](N(C)C)C(O)=C(C(N)=O)C(=O)[C@@]3(O)C(O)=C1C2=O] | NT | NT | NT |
| CX | 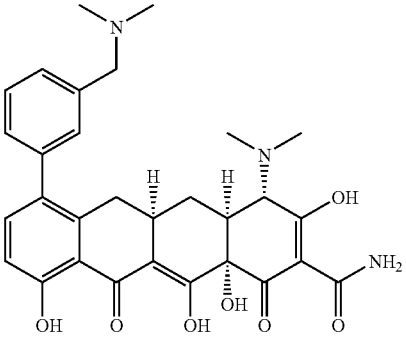 [SMILES: CN(C)Cc1cccc(-c2ccc(O)c3c2C[C@H]2C[C@H]4[C@H](N(C)C)C(O)=C(C(N)=O)C(=O)[C@@]4(O)C(O)=C2C3=O)c1] | * |  | ** |
| CY | 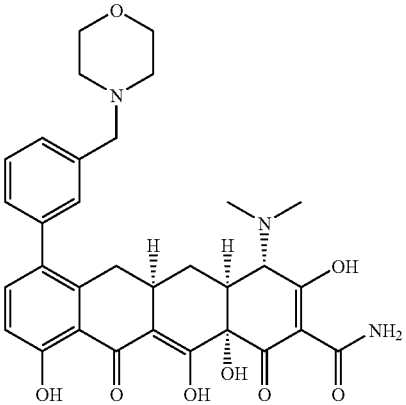 [SMILES: CN(C)[C@@H]1C(O)=C(C(N)=O)C(=O)[C@@]2(O)C(O)=C3C(=O)c4c(O)ccc(-c5cccc(CN6CCOCC6)c5)c4C[C@H]3C[C@@H]12] |  |  | ** |

| ID | STRUCTURE | S. aureus | E. hirae | E. coli |
|---|---|---|---|---|
| CZ | 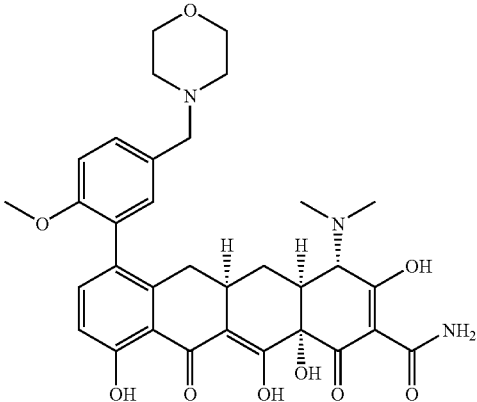 [SMILES: COc1ccc(CN2CCOCC2)cc1-c1ccc(O)c2c1C[C@H]1C[C@H]3[C@H](N(C)C)C(O)=C(C(N)=O)C(=O)[C@@]3(O)C(O)=C1C2=O] |  |  | ** |
| DA | 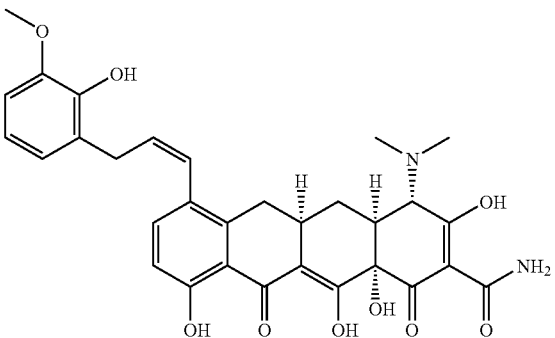 [SMILES: COc1cccc(C/C=C\c2ccc(O)c3c2C[C@H]2C[C@H]4[C@H](N(C)C)C(O)=C(C(N)=O)C(=O)[C@@]4(O)C(O)=C2C3=O)c1O] |  |  | * |
| DB | 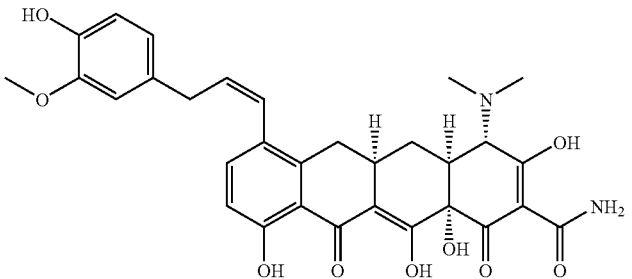 [SMILES: COc1cc(C/C=C\c2ccc(O)c3c2C[C@H]2C[C@H]4[C@H](N(C)C)C(O)=C(C(N)=O)C(=O)[C@@]4(O)C(O)=C2C3=O)ccc1O] |  |  | * |
| DC | 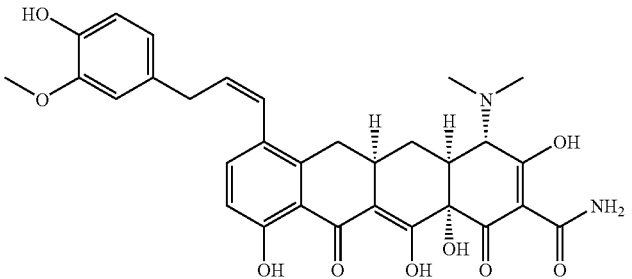 [SMILES: COc1cc(C/C=C\c2ccc(O)c3c2C[C@H]2C[C@H]4[C@H](N(C)C)C(O)=C(C(N)=O)C(=O)[C@@]4(O)C(O)=C2C3=O)ccc1O] |  |  | * |

| ID | STRUCTURE | S. aureus | E. hirae | E. coli |
|---|---|---|---|---|
| DD | 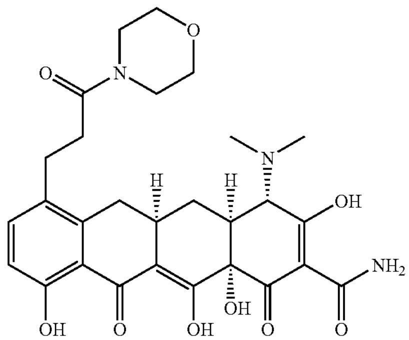 [SMILES: CN(C)[C@@H]1C(O)=C(C(N)=O)C(=O)[C@@]2(O)C(O)=C3C(=O)c4c(O)ccc(CCC(=O)N5CCOCC5)c4C[C@H]3C[C@@H]12] | * | ** | * |
| DE | 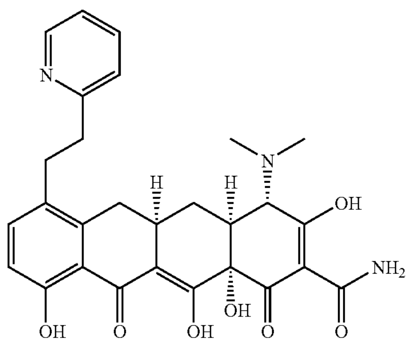 [SMILES: CN(C)[C@@H]1C(O)=C(C(N)=O)C(=O)[C@@]2(O)C(O)=C3C(=O)c4c(O)ccc(CCc5ccccn5)c4C[C@H]3C[C@@H]12] |  |  | * |
| DF | 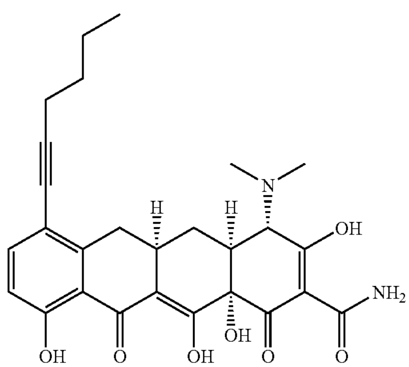 [SMILES: CCCCC#Cc1ccc(O)c2c1C[C@H]1C[C@H]3[C@H](N(C)C)C(O)=C(C(N)=O)C(=O)[C@@]3(O)C(O)=C1C2=O] | * | * | * |
| DG | 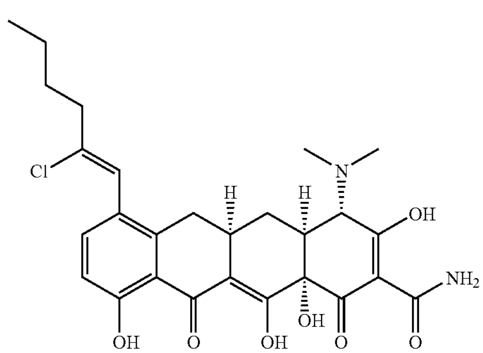 [SMILES: CCCC/C(Cl)=C/c1ccc(O)c2c1C[C@H]1C[C@H]3[C@H](N(C)C)C(O)=C(C(N)=O)C(=O)[C@@]3(O)C(O)=C1C2=O] | * | * | * |

-continued
| ID | STRUCTURE | S. aureus | E. hirae | E. coli |
|----|-----------|-----------|----------|---------|
| DH | 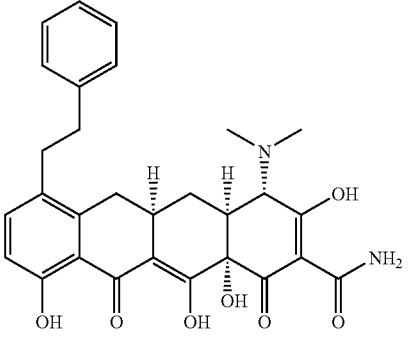 [SMILES: CN(C)[C@@H]1C(O)=C(C(N)=O)C(=O)[C@@]2(O)C(O)=C3C(=O)c4c(O)ccc(CCc5ccccc5)c4C[C@H]3C[C@@H]12] | * | * | * |
| DI | 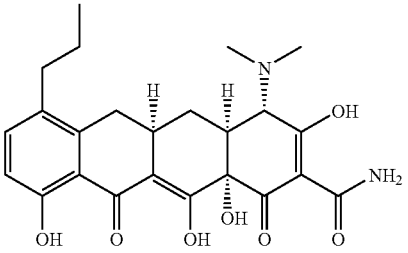 [SMILES: CCCc1ccc(O)c2c1C[C@H]1C[C@H]3[C@H](N(C)C)C(O)=C(C(N)=O)C(=O)[C@@]3(O)C(O)=C1C2=O] |  | * | |
| DJ | 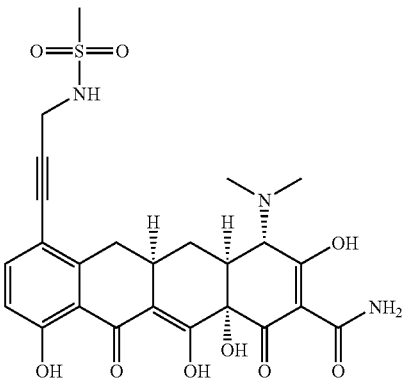 [SMILES: CN(C)[C@@H]1C(O)=C(C(N)=O)C(=O)[C@@]2(O)C(O)=C3C(=O)c4c(O)ccc(C#CCNS(C)(=O)=O)c4C[C@H]3C[C@@H]12] | * | * | * |
| DK | 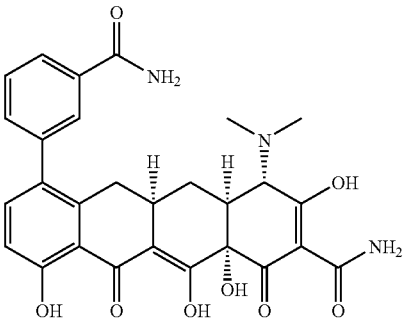 [SMILES: CN(C)[C@@H]1C(O)=C(C(N)=O)C(=O)[C@@]2(O)C(O)=C3C(=O)c4c(O)ccc(-c5cccc(C(N)=O)c5)c4C[C@H]3C[C@@H]12] | * |  | ** |

| ID | STRUCTURE | S. aureus | E. hirae | E. coli |
|---|---|---|---|---|
| DL | 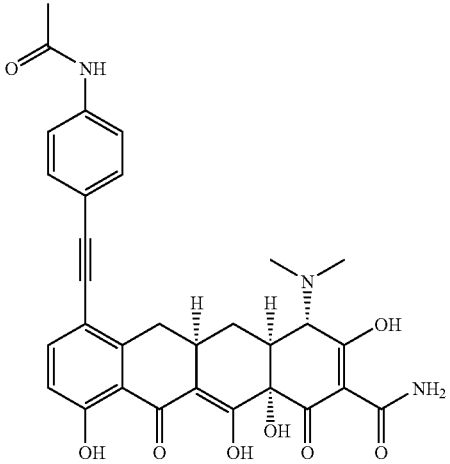 [SMILES: CC(=O)Nc1ccc(C#Cc2ccc(O)c3c2C[C@H]2C[C@H]4[C@H](N(C)C)C(O)=C(C(N)=O)C(=O)[C@@]4(O)C(O)=C2C3=O)cc1] |  |  | * |
| DM | 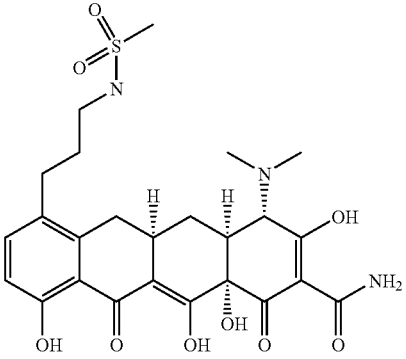 [SMILES: CN(C)[C@@H]1C(O)=C(C(N)=O)C(=O)[C@@]2(O)C(O)=C3C(=O)c4c(O)ccc(CCCNS(C)(=O)=O)c4C[C@H]3C[C@@H]12] | * | ** | * |
| DN | 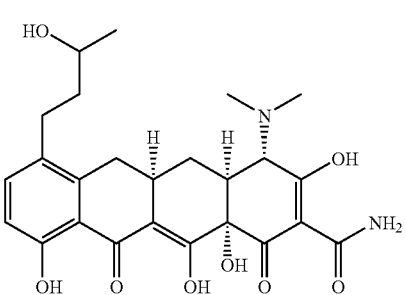 [SMILES: CC(O)CCc1ccc(O)c2c1C[C@H]1C[C@H]3[C@H](N(C)C)C(O)=C(C(N)=O)C(=O)[C@@]3(O)C(O)=C1C2=O] | * | ** | * |
| DO | 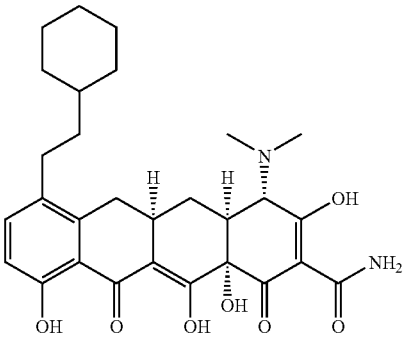 [SMILES: CN(C)[C@@H]1C(O)=C(C(N)=O)C(=O)[C@@]2(O)C(O)=C3C(=O)c4c(O)ccc(CCC5CCCCC5)c4C[C@H]3C[C@@H]12] |  |  | * |

-continued

| ID | STRUCTURE | S. aureus | E. hirae | E. coli |
|---|---|---|---|---|
| DP | 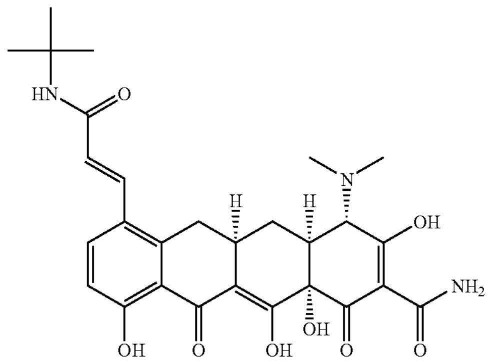 [SMILES: CN(C)[C@@H]1C(O)=C(C(N)=O)C(=O)[C@@]2(O)C(O)=C3C(=O)c4c(O)ccc(/C=C/C(=O)NC(C)(C)C)c4C[C@H]3C[C@@H]12] | * | * | * |
| DQ | 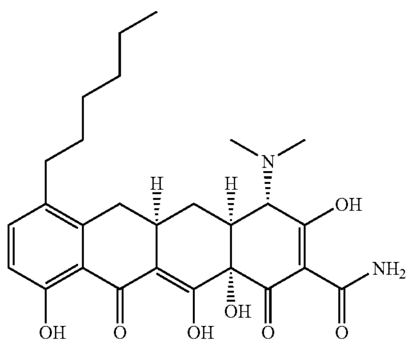 [SMILES: CCCCCCc1ccc(O)c2c1C[C@H]1C[C@H]3[C@H](N(C)C)C(O)=C(C(N)=O)C(=O)[C@@]3(O)C(O)=C1C2=O] |  |  | * |
| DR | 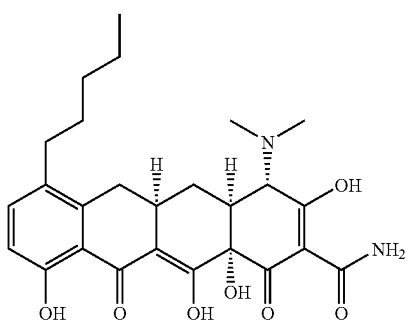 [SMILES: CCCCCc1ccc(O)c2c1C[C@H]1C[C@H]3[C@H](N(C)C)C(O)=C(C(N)=O)C(=O)[C@@]3(O)C(O)=C1C2=O] |  |  | * |
| DS | 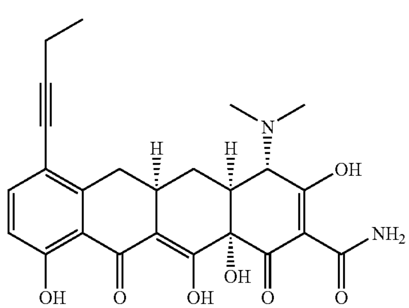 [SMILES: CCC#Cc1ccc(O)c2c1C[C@H]1C[C@H]3[C@H](N(C)C)C(O)=C(C(N)=O)C(=O)[C@@]3(O)C(O)=C1C2=O] | * |  | ** |

-continued
| ID | STRUCTURE | S. aureus | E. hirae | E. coli |
|---|---|---|---|---|
| DT | 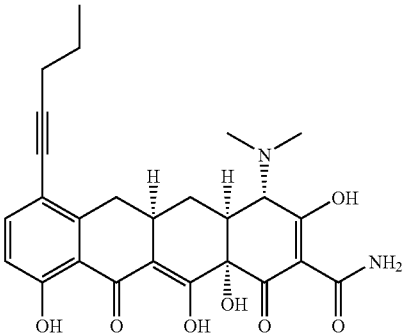 [SMILES: CCCC#Cc1ccc(O)c2c1C[C@H]1C[C@H]3[C@H](N(C)C)C(O)=C(C(N)=O)C(=O)[C@@]3(O)C(O)=C1C2=O] | * | * | * |
| DU | 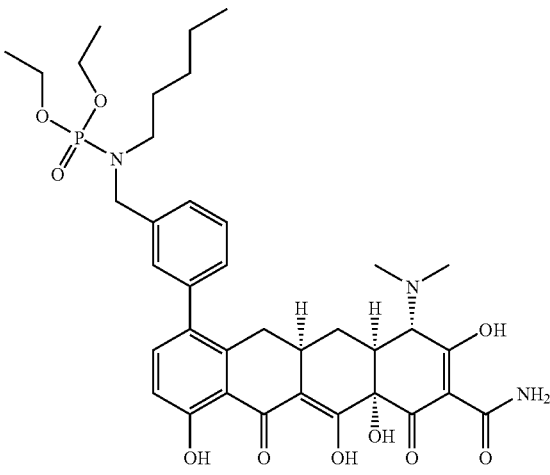 [SMILES: CCCCCN(Cc1cccc(-c2ccc(O)c3c2C[C@H]2C[C@H]4[C@H](N(C)C)C(O)=C(C(N)=O)C(=O)[C@@]4(O)C(O)=C2C3=O)c1)P(=O)(OCC)OCC] | NT | NT | NT |
| DV | 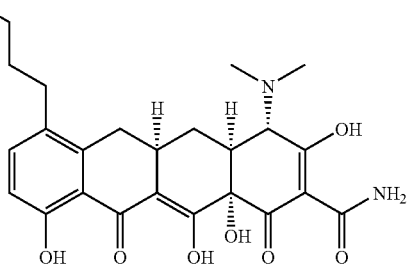 | * | * | * |
| DW | 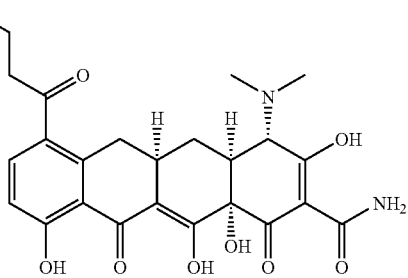 | * | * | ** |

| ID | STRUCTURE | S. aureus | E. hirae | E. coli |
|---|---|---|---|---|
| DX | 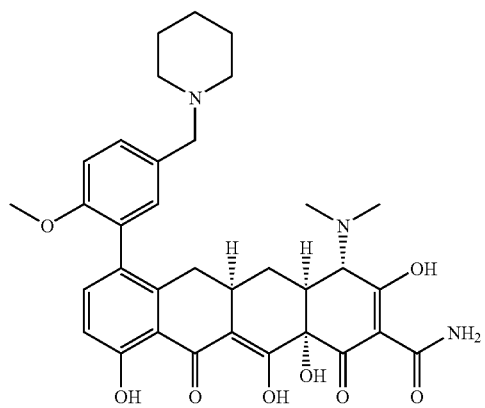 [SMILES: COc1ccc(CN2CCCCC2)cc1-c1ccc(O)c2c1C[C@H]1C[C@H]3[C@H](N(C)C)C(O)=C(C(N)=O)C(=O)[C@@]3(O)C(O)=C1C2=O] | * |  | *** |
| DY | 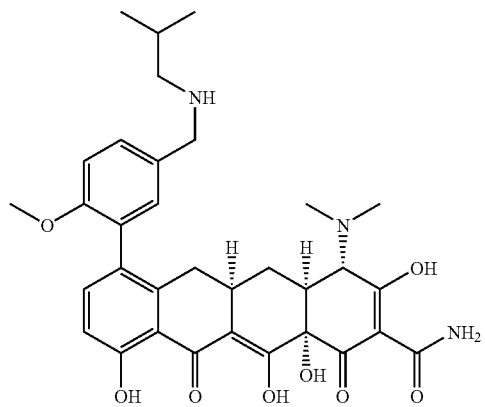 [SMILES: COc1ccc(CNCC(C)C)cc1-c1ccc(O)c2c1C[C@H]1C[C@H]3[C@H](N(C)C)C(O)=C(C(N)=O)C(=O)[C@@]3(O)C(O)=C1C2=O] | * |  | *** |
| DZ | 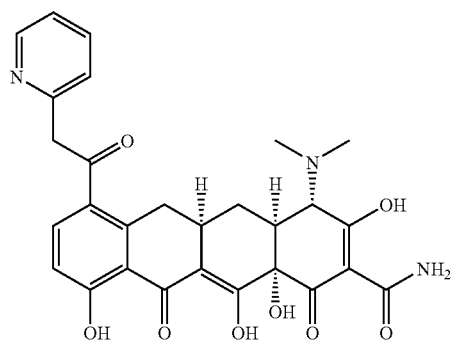 [SMILES: CN(C)[C@@H]1C(O)=C(C(N)=O)C(=O)[C@@]2(O)C(O)=C3C(=O)c4c(O)ccc(C(=O)Cc5ccccn5)c4C[C@H]3C[C@@H]12] | *** | NT | * |
| EA | 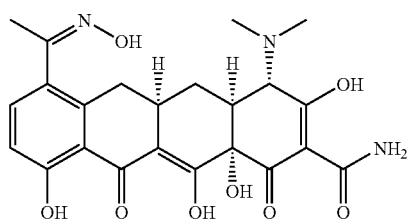 [SMILES: C/C(=N/O)c1ccc(O)c2c1C[C@H]1C[C@H]3[C@H](N(C)C)C(O)=C(C(N)=O)C(=O)[C@@]3(O)C(O)=C1C2=O] | * | NT | * |

-continued
| ID | STRUCTURE | S. aureus | E. hirae | E. coli |
|---|---|---|---|---|
| EB | 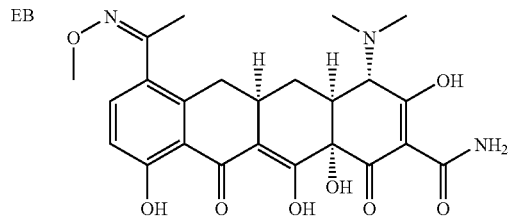 |  | NT |  |
| EC | 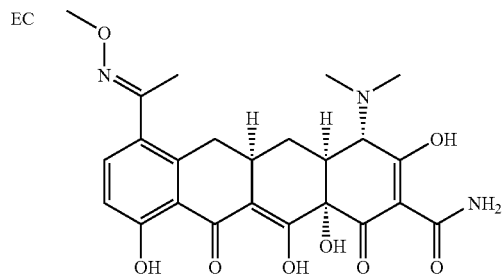 |  | NT |  |
| ED | 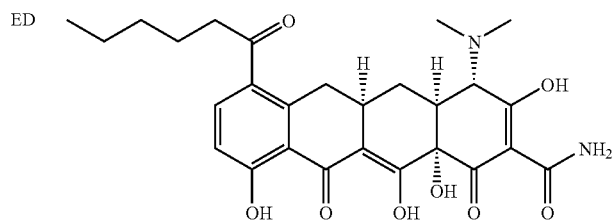 | *** | NT | * |
| EF | 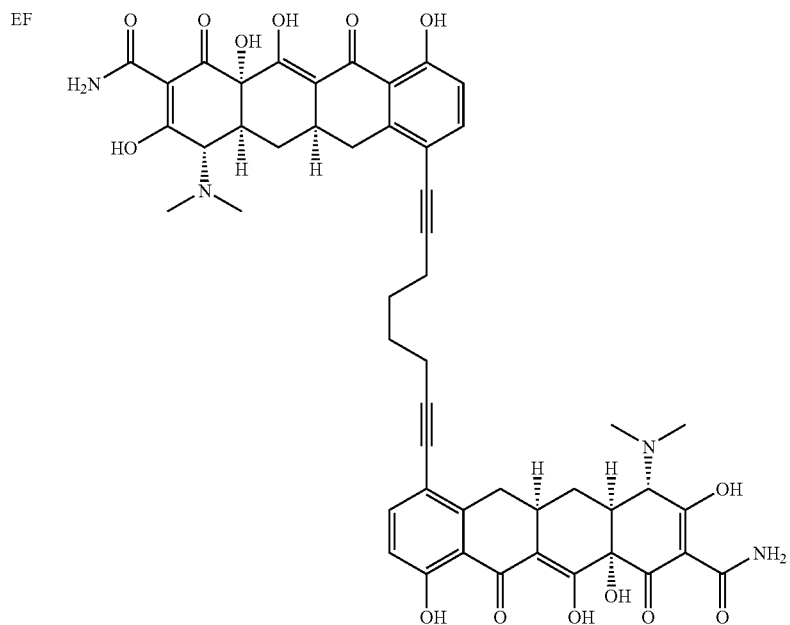 | * | * | * |

| ID | STRUCTURE | S. aureus | E. hirae | E. coli |
|---|---|---|---|---|
| EG | 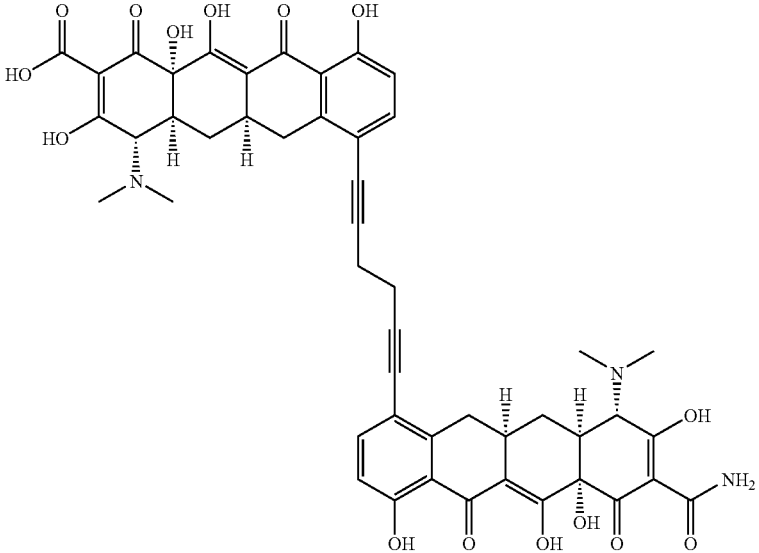 [SMILES: CN(C)[C@@H]1C(O)=C(C(N)=O)C(=O)[C@@]2(O)C(O)=C3C(=O)c4c(O)ccc(C#CCCC#Cc5ccc(O)c6c5C[C@H]5C[C@H]7[C@H](N(C)C)C(O)=C(C(=O)O)C(=O)[C@@]7(O)C(O)=C5C6=O)c4C[C@H]3C[C@@H]12] | * | * | * |
| EH | 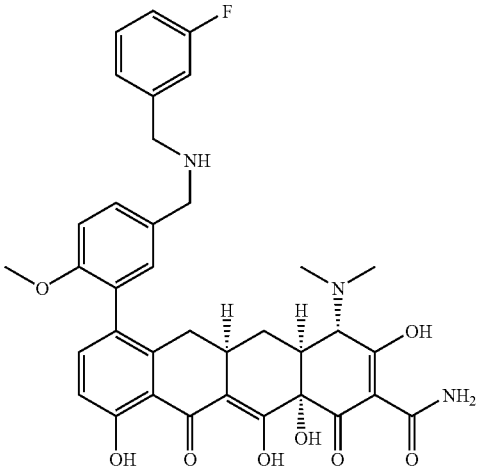 [SMILES: COc1ccc(CNCc2cccc(F)c2)cc1-c1ccc(O)c2c1C[C@H]1C[C@H]3[C@H](N(C)C)C(O)=C(C(N)=O)C(=O)[C@@]3(O)C(O)=C1C2=O] |  |  | *** |
| EI | 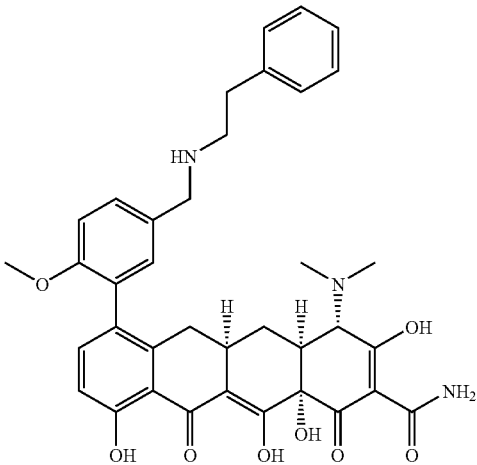 [SMILES: COc1ccc(CNCCc2ccccc2)cc1-c1ccc(O)c2c1C[C@H]1C[C@H]3[C@H](N(C)C)C(O)=C(C(N)=O)C(=O)[C@@]3(O)C(O)=C1C2=O] |  |  | *** |

| ID | STRUCTURE | S. aureus | E. hirae | E. coli |
|---|---|---|---|---|
| EJ | 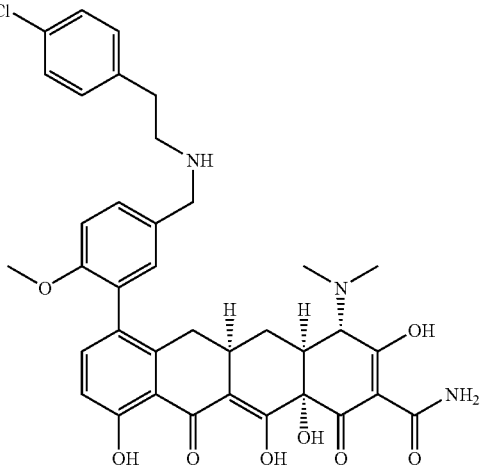 |  |  | *** |
| EK | 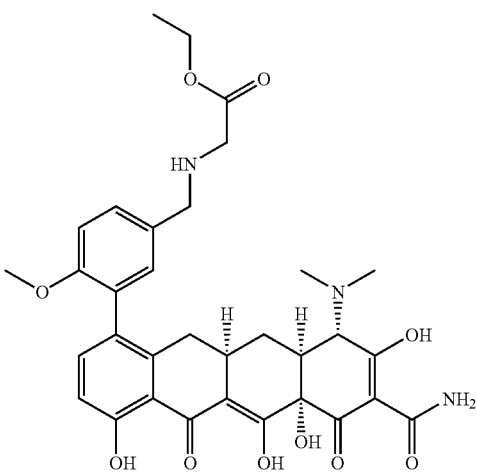 [SMILES: CCOC(=O)CNCc1ccc(OC)c(-c2ccc(O)c3c2C[C@H]2C[C@H]4[C@H](N(C)C)C(O)=C(C(N)=O)C(=O)[C@@]4(O)C(O)=C2C3=O)c1] |  |  | ** |
| EL | 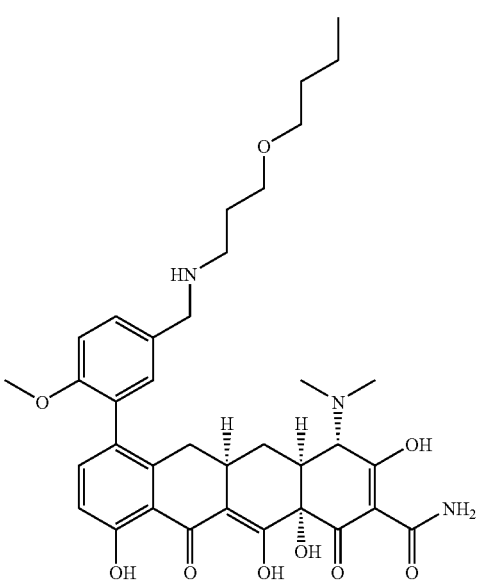 [SMILES: CCCCOCCCNCc1ccc(OC)c(-c2ccc(O)c3c2C[C@H]2C[C@H]4[C@H](N(C)C)C(O)=C(C(N)=O)C(=O)[C@@]4(O)C(O)=C2C3=O)c1] | ** | * | ** |

-continued
| ID | STRUCTURE | S. aureus | E. hirae | E. coli |
|---|---|---|---|---|
| EM | 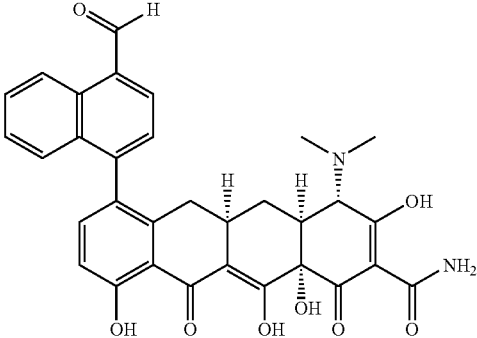 [SMILES: CN(C)[C@@H]1C(O)=C(C(N)=O)C(=O)[C@@]2(O)C(O)=C3C(=O)c4c(O)ccc(-c5ccc(C=O)c6ccccc56)c4C[C@H]3C[C@@H]12] | NT | NT | NT |
| EN | 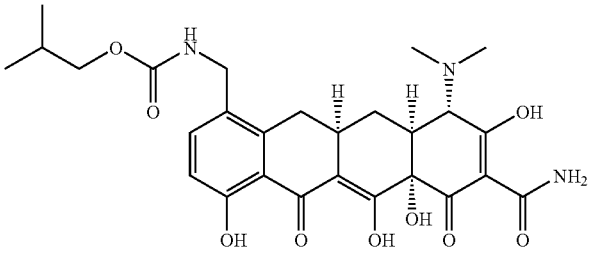 [SMILES: CC(C)COC(=O)NCc1ccc(O)c2c1C[C@H]1C[C@H]3[C@H](N(C)C)C(O)=C(C(N)=O)C(=O)[C@@]3(O)C(O)=C1C2=O] | NT | NT | NT |
| EO | 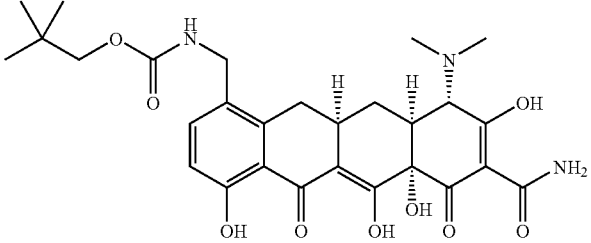 [SMILES: CN(C)[C@@H]1C(O)=C(C(N)=O)C(=O)[C@@]2(O)C(O)=C3C(=O)c4c(O)ccc(CNC(=O)OCC(C)(C)C)c4C[C@H]3C[C@@H]12] | NT | NT | NT |
| EP | 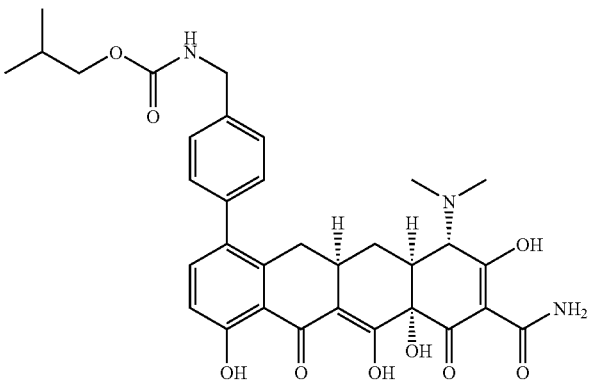 [SMILES: CC(C)COC(=O)NCc1ccc(-c2ccc(O)c3c2C[C@H]2C[C@H]4[C@H](N(C)C)C(O)=C(C(N)=O)C(=O)[C@@]4(O)C(O)=C2C3=O)cc1] | NT | NT | NT |

-continued
| ID | STRUCTURE | S. aureus | E. hirae | E. coli |
|---|---|---|---|---|
| EQ | 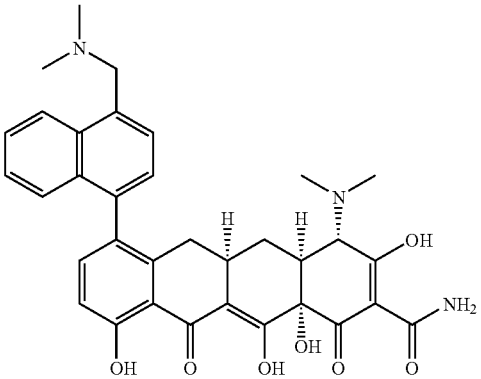 [SMILES: CN(C)Cc1ccc(-c2ccc(O)c3c2C[C@H]2C[C@H]4[C@H](N(C)C)C(O)=C(C(N)=O)C(=O)[C@@]4(O)C(O)=C2C3=O)c2ccccc12] | NT | NT | NT |
| ER | 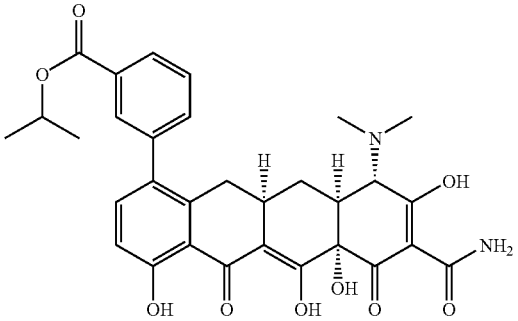 [SMILES: CC(C)OC(=O)c1cccc(-c2ccc(O)c3c2C[C@H]2C[C@H]4[C@H](N(C)C)C(O)=C(C(N)=O)C(=O)[C@@]4(O)C(O)=C2C3=O)c1] | NT | NT | NT |
| ES | 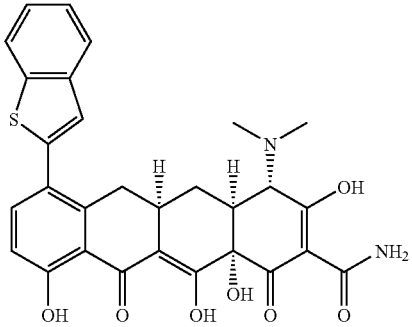 [SMILES: CN(C)[C@@H]1C(O)=C(C(N)=O)C(=O)[C@@]2(O)C(O)=C3C(=O)c4c(O)ccc(-c5cc6ccccc6s5)c4C[C@H]3C[C@@H]12] | NT | NT | NT |
| ET | 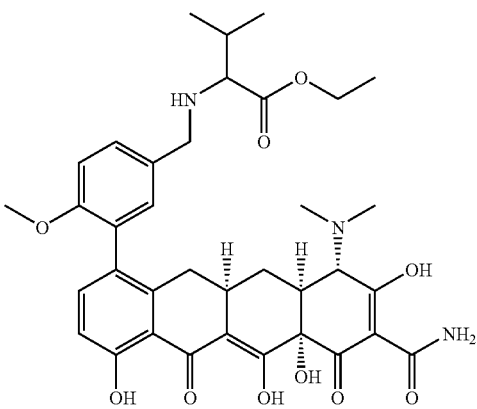 [SMILES: CCOC(=O)C(NCc1ccc(OC)c(-c2ccc(O)c3c2C[C@H]2C[C@H]4[C@H](N(C)C)C(O)=C(C(N)=O)C(=O)[C@@]4(O)C(O)=C2C3=O)c1)C(C)C] | NT | NT | NT |

| ID | STRUCTURE | S. aureus | E. hirae | E. coli |
|---|---|---|---|---|
| EU | 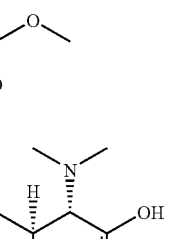 | NT | NT | NT |
| EV | 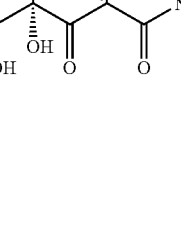 | NT | NT | NT |
| EW | 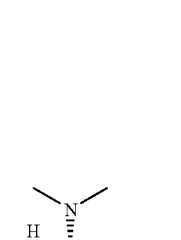 | NT | NT | NT |

| ID | STRUCTURE | S. aureus | E. hirae | E. coli |
|---|---|---|---|---|
| EX | 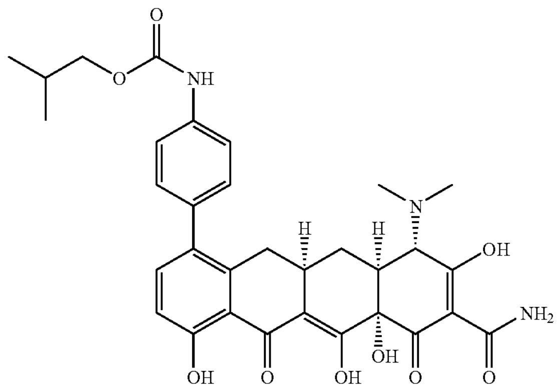 [SMILES: CC(C)COC(=O)Nc1ccc(-c2ccc(O)c3c2C[C@H]2C[C@H]4[C@H](N(C)C)C(O)=C(C(N)=O)C(=O)[C@@]4(O)C(O)=C2C3=O)cc1] | NT | NT | NT |
| EY | 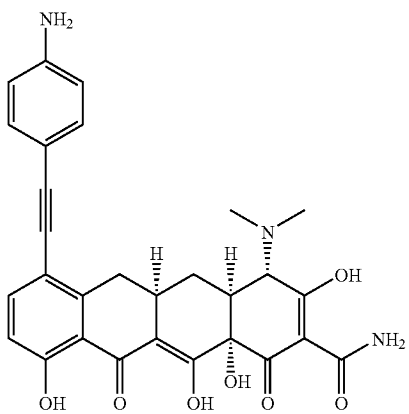 [SMILES: CN(C)[C@@H]1C(O)=C(C(N)=O)C(=O)[C@@]2(O)C(O)=C3C(=O)c4c(O)ccc(C#Cc5ccc(N)cc5)c4C[C@H]3C[C@@H]12] |  | * | * |
| EZ | 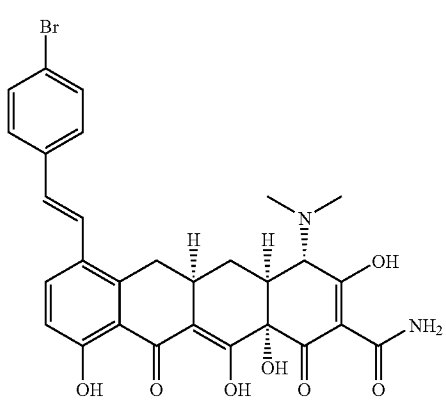 [SMILES: CN(C)[C@@H]1C(O)=C(C(N)=O)C(=O)[C@@]2(O)C(O)=C3C(=O)c4c(O)ccc(/C=C/c5ccc(Br)cc5)c4C[C@H]3C[C@@H]12] | * | ** | * |

-continued
| ID | STRUCTURE | S. aureus | E. hirae | E. coli |
|---|---|---|---|---|
| FA | 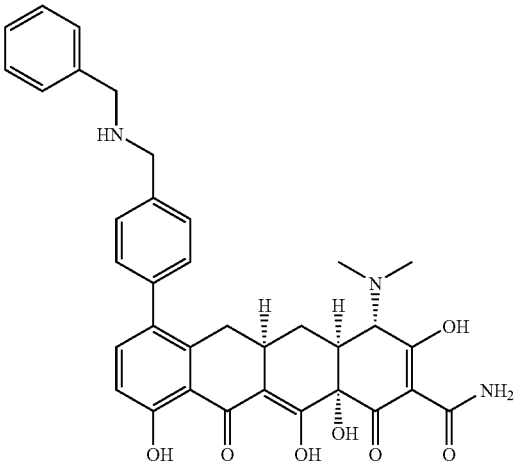 [SMILES: CN(C)[C@@H]1C(O)=C(C(N)=O)C(=O)[C@@]2(O)C(O)=C3C(=O)c4c(O)ccc(-c5ccc(CNCc6ccccc6)cc5)c4C[C@H]3C[C@@H]12] |  |  | *** |
| FB | 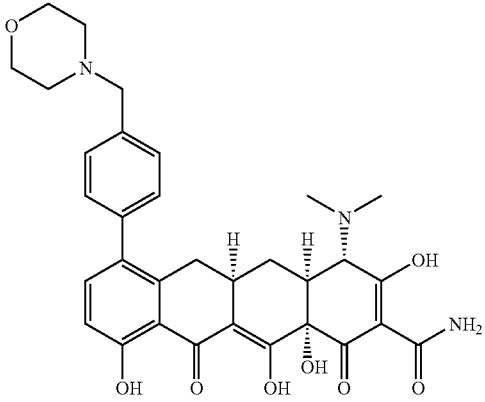 [SMILES: CN(C)[C@@H]1C(O)=C(C(N)=O)C(=O)[C@@]2(O)C(O)=C3C(=O)c4c(O)ccc(-c5ccc(CN6CCOCC6)cc5)c4C[C@H]3C[C@@H]12] |  |  | ** |
| FC | 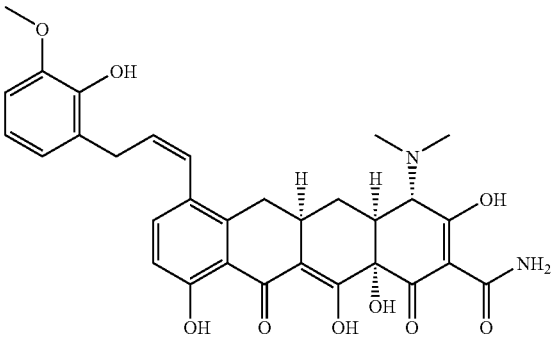 [SMILES: COc1cccc(C/C=C\c2ccc(O)c3c2C[C@H]2C[C@H]4[C@H](N(C)C)C(O)=C(C(N)=O)C(=O)[C@@]4(O)C(O)=C2C3=O)c1O] | NT | NT | NT |
| FD | 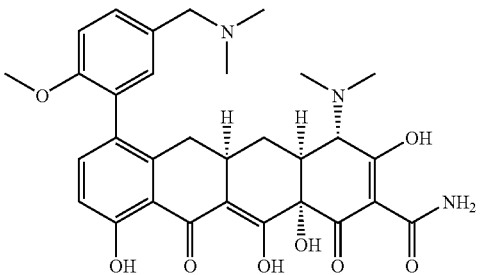 [SMILES: COc1ccc(CN(C)C)cc1-c1ccc(O)c2c1C[C@H]1C[C@H]3[C@H](N(C)C)C(O)=C(C(N)=O)C(=O)[C@@]3(O)C(O)=C1C2=O] | * |  | *** |

-continued
| ID | STRUCTURE | S. aureus | E. hirae | E. coli |
|---|---|---|---|---|
| FE | 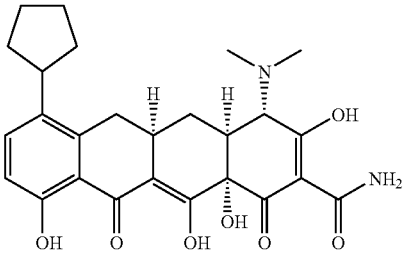 [SMILES: CN(C)[C@@H]1C(O)=C(C(N)=O)C(=O)[C@@]2(O)C(O)=C3C(=O)c4c(O)ccc(C5CCCC5)c4C[C@H]3C[C@@H]12] | NT | NT | NT |
| FF | 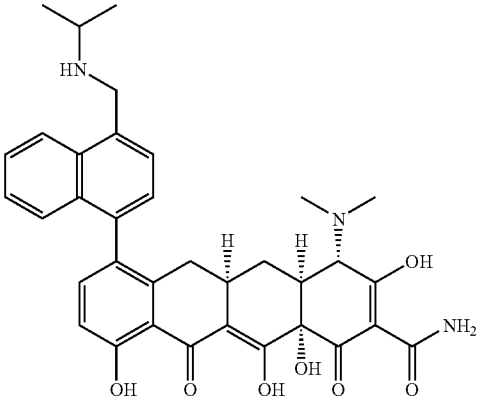 [SMILES: CC(C)NCc1ccc(-c2ccc(O)c3c2C[C@H]2C[C@H]4[C@H](N(C)C)C(O)=C(C(N)=O)C(=O)[C@@]4(O)C(O)=C2C3=O)c2ccccc12] | NT | NT | NT |
| FG | 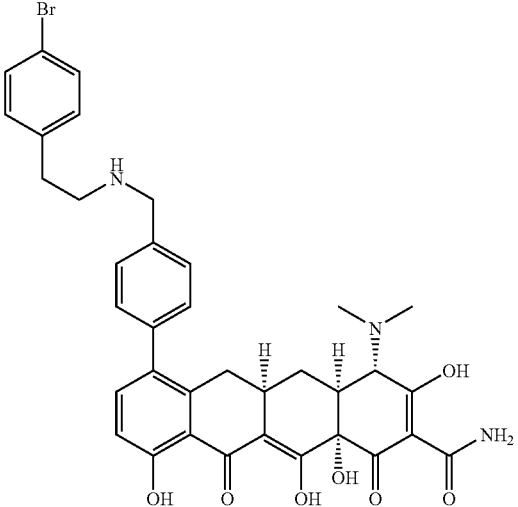 [SMILES: CN(C)[C@@H]1C(O)=C(C(N)=O)C(=O)[C@@]2(O)C(O)=C3C(=O)c4c(O)ccc(-c5ccc(CNCCc6ccc(Br)cc6)cc5)c4C[C@H]3C[C@@H]12] | NT | NT | NT |

-continued

| ID | STRUCTURE | S. aureus | E. hirae | E. coli |
|---|---|---|---|---|
| FH | 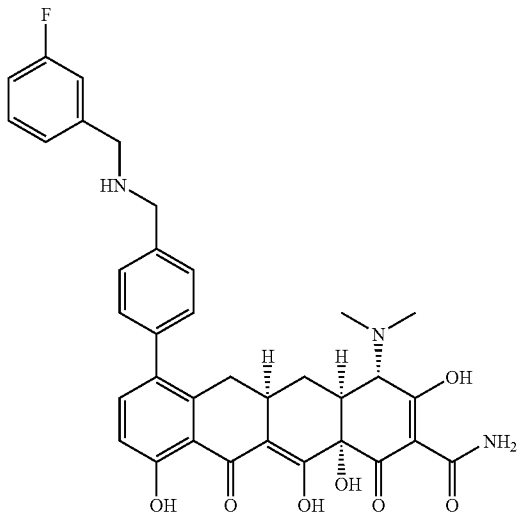 [SMILES: CN(C)[C@@H]1C(O)=C(C(N)=O)C(=O)[C@@]2(O)C(O)=C3C(=O)c4c(O)ccc(-c5ccc(CNCc6cccc(F)c6)cc5)c4C[C@H]3C[C@@H]12] | NT | NT | NT |
| FI | 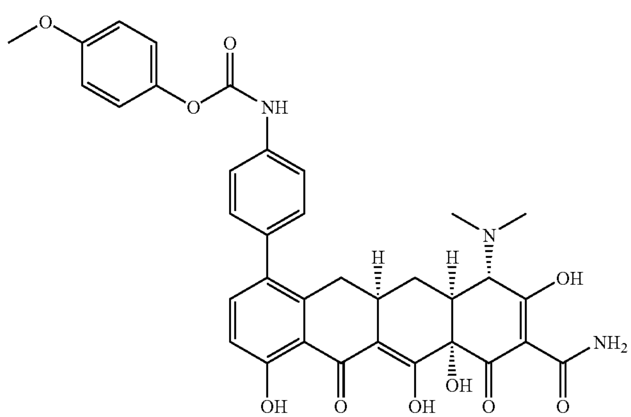 [SMILES: COc1ccc(OC(=O)Nc2ccc(-c3ccc(O)c4c3C[C@H]3C[C@H]5[C@H](N(C)C)C(O)=C(C(N)=O)C(=O)[C@@]5(O)C(O)=C3C4=O)cc2)cc1] | NT | NT | NT |
| FJ | 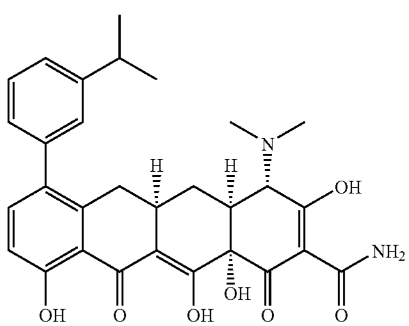 [SMILES: CC(C)c1cccc(-c2ccc(O)c3c2C[C@H]2C[C@H]4[C@H](N(C)C)C(O)=C(C(N)=O)C(=O)[C@@]4(O)C(O)=C2C3=O)c1] | NT | NT | NT |
| FK | 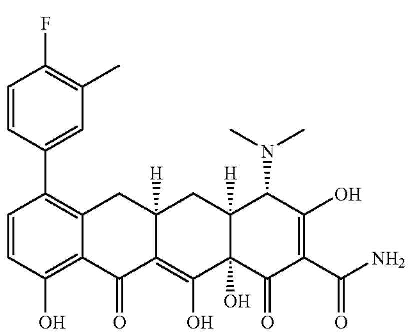 [SMILES: Cc1cc(-c2ccc(O)c3c2C[C@H]2C[C@H]4[C@H](N(C)C)C(O)=C(C(N)=O)C(=O)[C@@]4(O)C(O)=C2C3=O)ccc1F] | NT | NT | NT |

| ID | STRUCTURE | S. aureus | E. hirae | E. coli |
|---|---|---|---|---|
| FL | 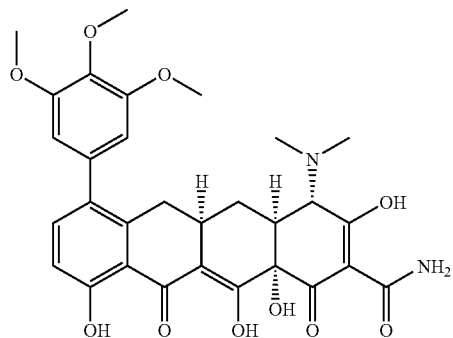 [SMILES: COc1cc(-c2ccc(O)c3c2C[C@H]2C[C@H]4[C@H](N(C)C)C(O)=C(C(N)=O)C(=O)[C@@]4(O)C(O)=C2C3=O)cc(OC)c1OC] | NT | NT | NT |
| FM | 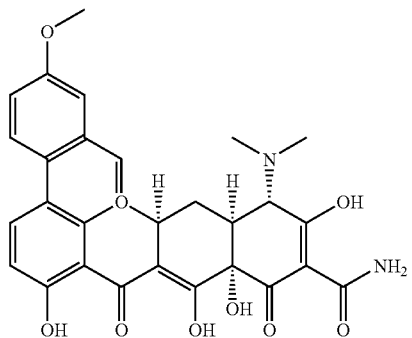 | NT | NT | NT |
| FN | 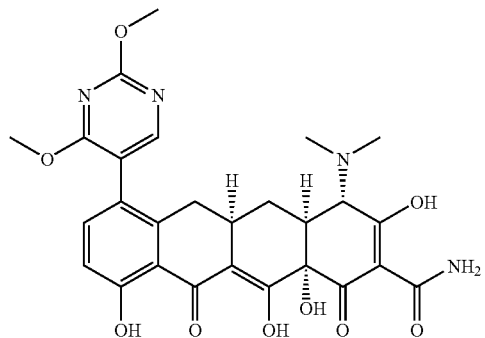 [SMILES: COc1ncc(-c2ccc(O)c3c2C[C@H]2C[C@H]4[C@H](N(C)C)C(O)=C(C(N)=O)C(=O)[C@@]4(O)C(O)=C2C3=O)c(OC)n1] | NT | NT | NT |
| FO | 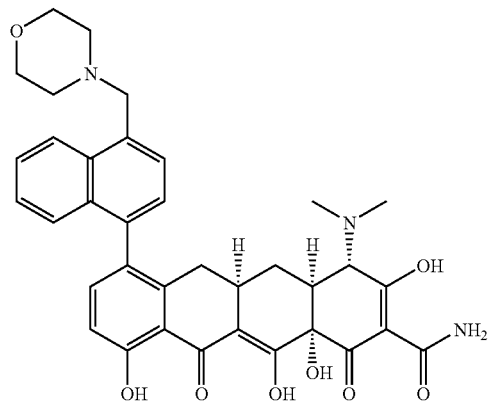 [SMILES: CN(C)[C@@H]1C(O)=C(C(N)=O)C(=O)[C@@]2(O)C(O)=C3C(=O)c4c(O)ccc(-c5ccc(CN6CCOCC6)c6ccccc56)c4C[C@H]3C[C@@H]12] | NT | NT | NT |

| ID | STRUCTURE | S. aureus | E. hirae | E. coli |
|---|---|---|---|---|
| FP | 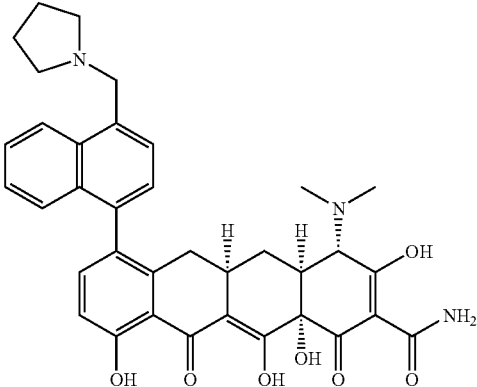 [SMILES: CN(C)[C@@H]1C(O)=C(C(N)=O)C(=O)[C@@]2(O)C(O)=C3C(=O)c4c(O)ccc(-c5ccc(CN6CCCC6)c6ccccc56)c4C[C@H]3C[C@@H]12] | NT | NT | NT |
| FQ | 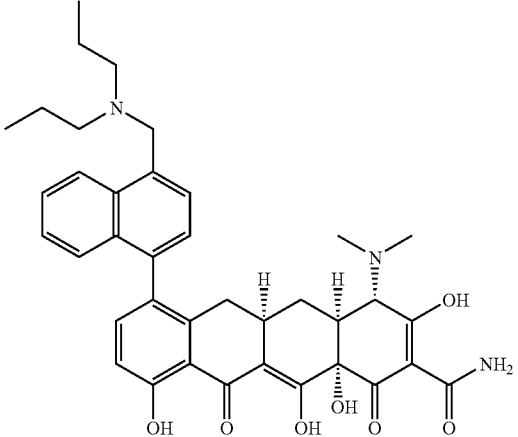 [SMILES: CCCN(CCC)Cc1ccc(-c2ccc(O)c3c2C[C@H]2C[C@H]4[C@H](N(C)C)C(O)=C(C(N)=O)C(=O)[C@@]4(O)C(O)=C2C3=O)c2ccccc12] | NT | NT | NT |
| FR | 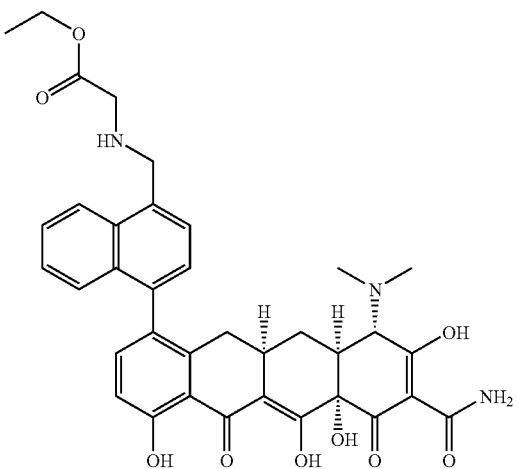 [SMILES: CCOC(=O)CNCc1ccc(-c2ccc(O)c3c2C[C@H]2C[C@H]4[C@H](N(C)C)C(O)=C(C(N)=O)C(=O)[C@@]4(O)C(O)=C2C3=O)c2ccccc12] | NT | NT | NT |

| ID | STRUCTURE | S. aureus | E. hirae | E. coli |
|---|---|---|---|---|
| FS | 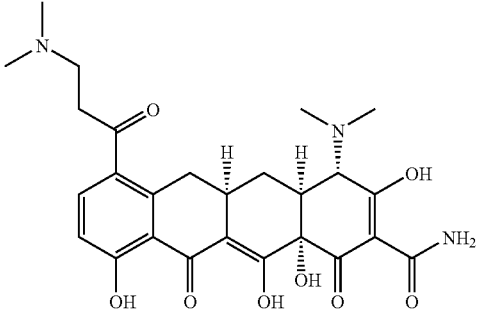 [SMILES: CN(C)CCC(=O)c1ccc(O)c2c1C[C@H]1C[C@H]3[C@H](N(C)C)C(O)=C(C(N)=O)C(=O)[C@@]3(O)C(O)=C1C2=O] | NT | NT | NT |
| FT | 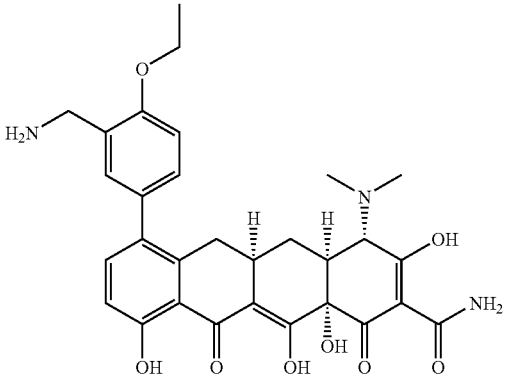 [SMILES: CCOc1ccc(-c2ccc(O)c3c2C[C@H]2C[C@H]4[C@H](N(C)C)C(O)=C(C(N)=O)C(=O)[C@@]4(O)C(O)=C2C3=O)cc1CN] | NT | NT | NT |
| FU | 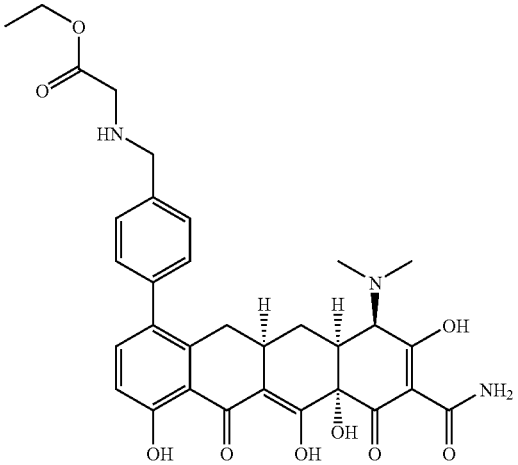 [SMILES: CCOC(=O)CNCc1ccc(-c2ccc(O)c3c2C[C@H]2C[C@H]4[C@@H](N(C)C)C(O)=C(C(N)=O)C(=O)[C@@]4(O)C(O)=C2C3=O)cc1] | NT | NT | NT |
| FV | 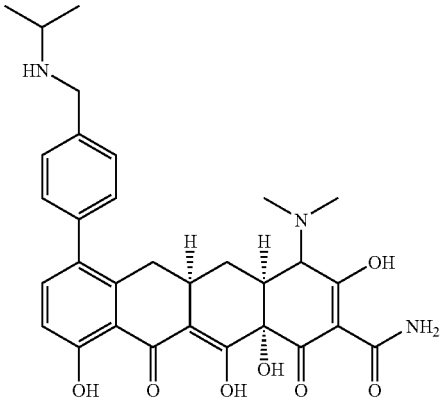 [SMILES: CC(C)NCc1ccc(-c2ccc(O)c3c2C[C@H]2C[C@H]4C(N(C)C)C(O)=C(C(N)=O)C(=O)[C@@]4(O)C(O)=C2C3=O)cc1] | NT | NT | NT |

-continued

| ID | STRUCTURE | S. aureus | E. hirae | E. coli |
|---|---|---|---|---|
| FW | 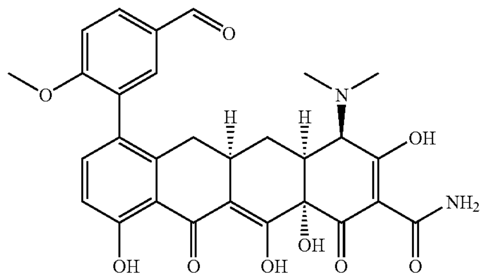 [SMILES: COc1ccc(C=O)cc1-c1ccc(O)c2c1C[C@H]1C[C@H]3[C@@H](N(C)C)C(O)=C(C(N)=O)C(=O)[C@@]3(O)C(O)=C1C2=O] | NT | NT | NT |
| FX | 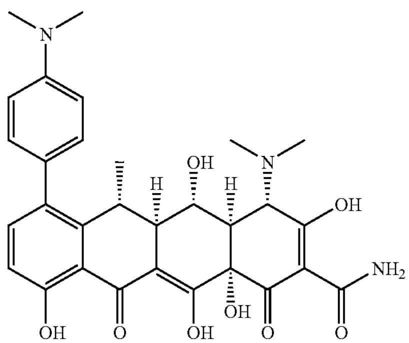 | NT | NT | NT |
| FY | 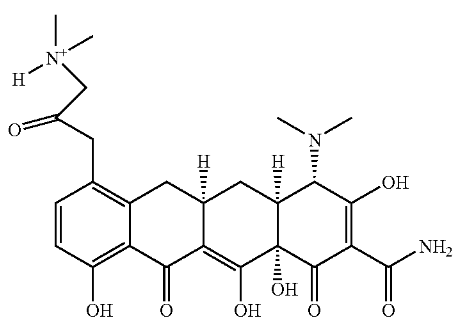 [SMILES: CN(C)[C@@H]1C(O)=C(C(N)=O)C(=O)[C@@]2(O)C(O)=C3C(=O)c4c(O)ccc(CC(=O)C[NH+](C)C)c4C[C@H]3C[C@@H]12] | NT | NT | NT |
| FZ | 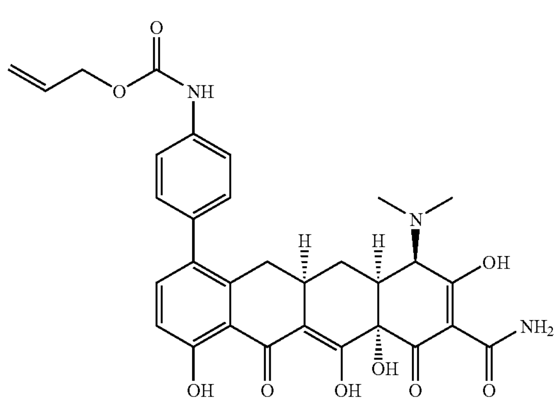 [SMILES: C=CCOC(=O)Nc1ccc(-c2ccc(O)c3c2C[C@H]2C[C@H]4[C@@H](N(C)C)C(O)=C(C(N)=O)C(=O)[C@@]4(O)C(O)=C2C3=O)cc1] | NT | NT | NT |

-continued
| ID | STRUCTURE | S. aureus | E. hirae | E. coli |
|---|---|---|---|---|
| GA | 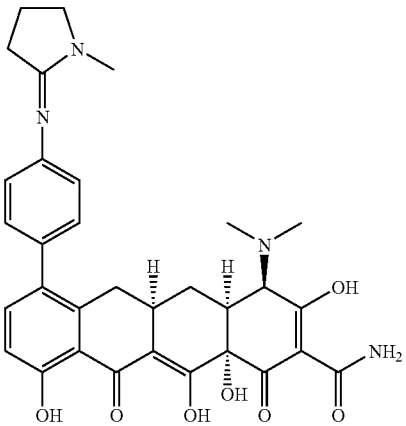 [SMILES: CN1CCCC1=Nc1ccc(-c2ccc(O)c3c2C[C@H]2C[C@H]4[C@@H](N(C)C)C(O)=C(C(N)=O)C(=O)[C@@]4(O)C(O)=C2C3=O)cc1] | NT | NT | NT |
| GB | 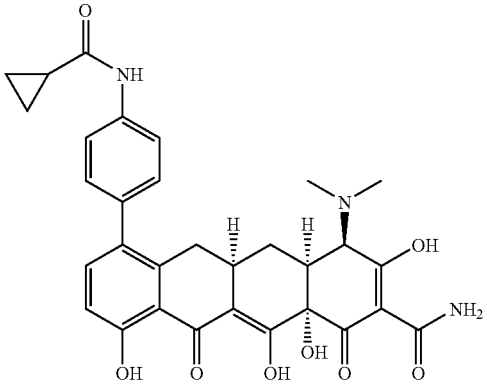 [SMILES: CN(C)[C@H]1C(O)=C(C(N)=O)C(=O)[C@@]2(O)C(O)=C3C(=O)c4c(O)ccc(-c5ccc(NC(=O)C6CC6)cc5)c4C[C@H]3C[C@@H]12] | NT | NT | NT |
| GC | 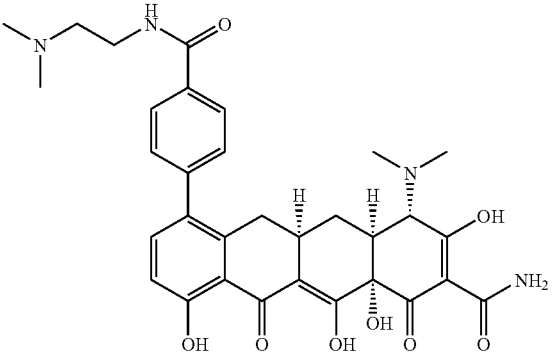 [SMILES: CN(C)CCNC(=O)c1ccc(-c2ccc(O)c3c2C[C@H]2C[C@H]4[C@H](N(C)C)C(O)=C(C(N)=O)C(=O)[C@@]4(O)C(O)=C2C3=O)cc1] | NT | NT | NT |
| GD | 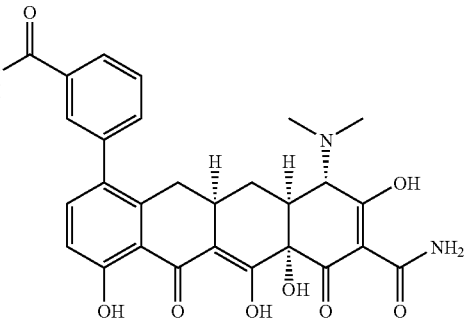 | NT | NT | NT |

-continued

| ID | STRUCTURE | S. aureus | E. hirae | E. coli |
|----|-----------|-----------|----------|---------|
| GE | 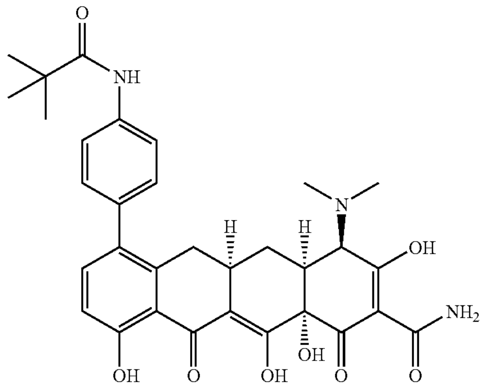 [SMILES: CN(C)[C@H]1C(O)=C(C(N)=O)C(=O)[C@@]2(O)C(O)=C3C(=O)c4c(O)ccc(-c5ccc(NC(=O)C(C)(C)C)cc5)c4C[C@H]3C[C@@H]12] | NT | NT | NT |
| GF | 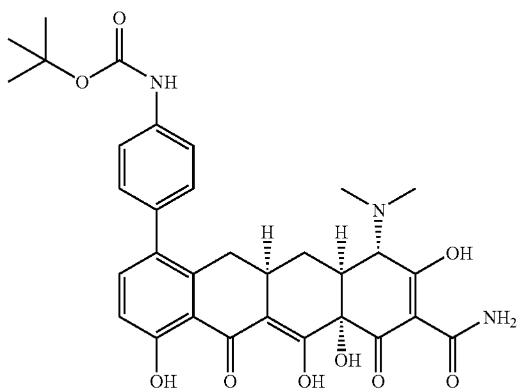 [SMILES: CN(C)[C@@H]1C(O)=C(C(N)=O)C(=O)[C@@]2(O)C(O)=C3C(=O)c4c(O)ccc(-c5ccc(NC(=O)OC(C)(C)C)cc5)c4C[C@H]3C[C@@H]12] | NT | NT | NT |
| GG | 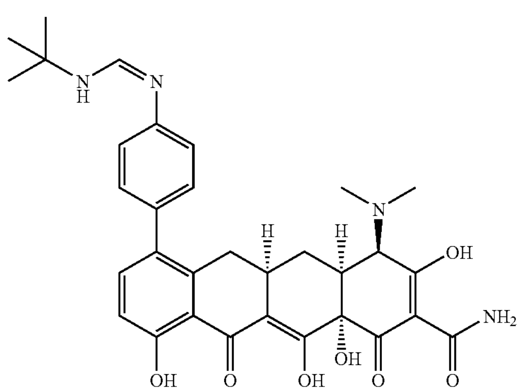 [SMILES: CN(C)[C@H]1C(O)=C(C(N)=O)C(=O)[C@@]2(O)C(O)=C3C(=O)c4c(O)ccc(-c5ccc(/N=C\NC(C)(C)C)cc5)c4C[C@H]3C[C@@H]12] | NT | NT | NT |

| ID | STRUCTURE | S. aureus | E. hirae | E. coli |
|---|---|---|---|---|
| GH | 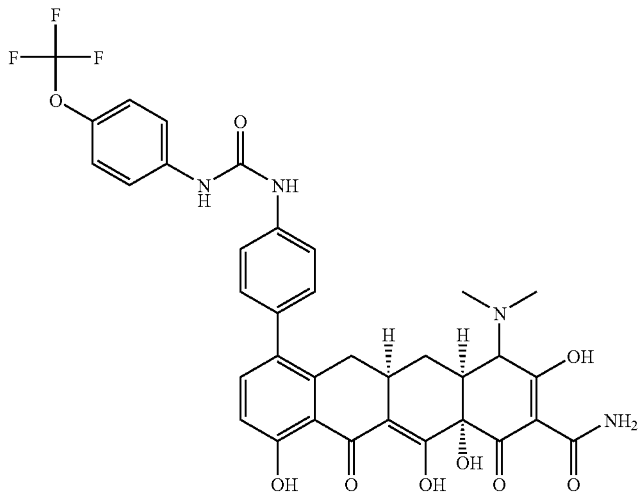 [SMILES: CN(C)C1C(O)=C(C(N)=O)C(=O)[C@@]2(O)C(O)=C3C(=O)c4c(O)ccc(-c5ccc(NC(=O)Nc6ccc(OC(F)(F)F)cc6)cc5)c4C[C@H]3C[C@@H]12] | NT | NT | NT |
| GI | 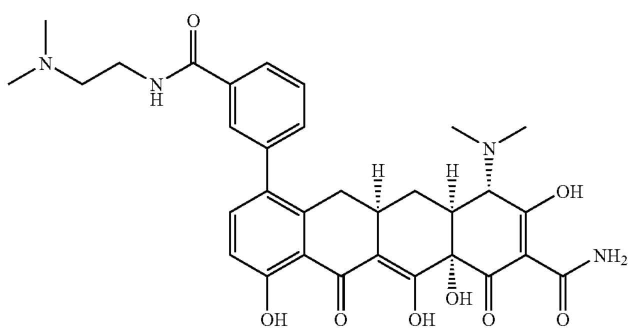 [SMILES: CN(C)CCNC(=O)c1cccc(-c2ccc(O)c3c2C[C@H]2C[C@H]4[C@H](N(C)C)C(O)=C(C(N)=O)C(=O)[C@@]4(O)C(O)=C2C3=O)c1] | NT | NT | NT |
| GJ | 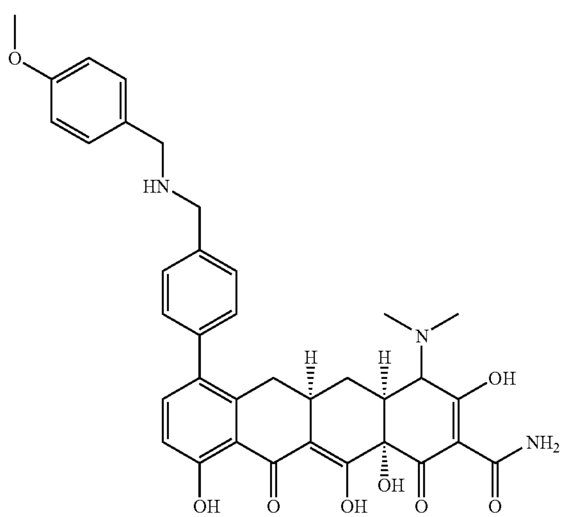 [SMILES: COc1ccc(CNCc2ccc(-c3ccc(O)c4c3C[C@H]3C[C@H]5C(N(C)C)C(O)=C(C(N)=O)C(=O)[C@@]5(O)C(O)=C3C4=O)cc2)cc1] | NT | NT | NT |

| ID | STRUCTURE | S. aureus | E. hirae | E. coli |
|---|---|---|---|---|
| GK | 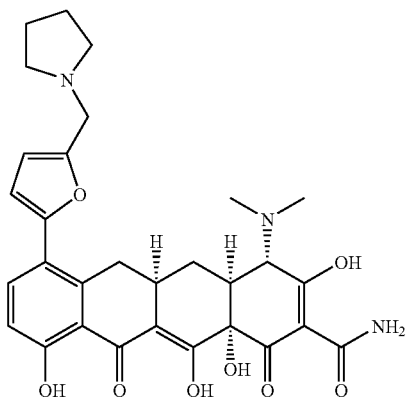 [SMILES: CN(C)[C@@H]1C(O)=C(C(N)=O)C(=O)[C@@]2(O)C(O)=C3C(=O)c4c(O)ccc(-c5ccc(CN6CCCC6)o5)c4C[C@H]3C[C@@H]12] | NT | NT | NT |
| GL | 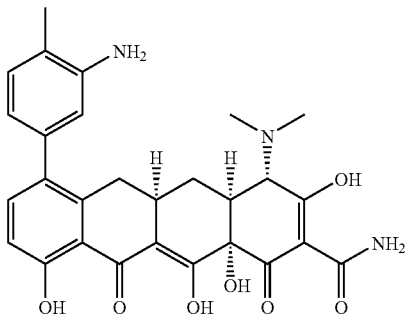 [SMILES: Cc1ccc(-c2ccc(O)c3c2C[C@H]2C[C@H]4[C@H](N(C)C)C(O)=C(C(N)=O)C(=O)[C@@]4(O)C(O)=C2C3=O)cc1N] | NT | NT | NT |
| GM | 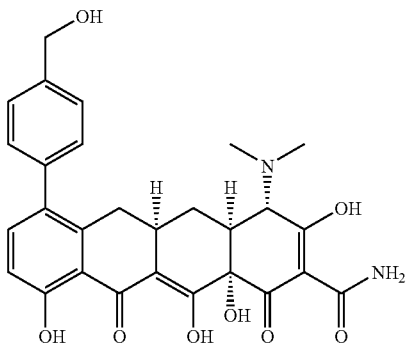 [SMILES: CN(C)[C@@H]1C(O)=C(C(N)=O)C(=O)[C@@]2(O)C(O)=C3C(=O)c4c(O)ccc(-c5ccc(CO)cc5)c4C[C@H]3C[C@@H]12] | NT | NT | NT |
| GN | 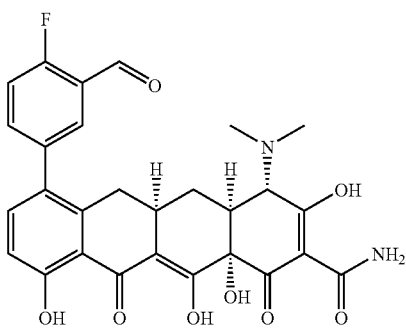 [SMILES: CN(C)[C@@H]1C(O)=C(C(N)=O)C(=O)[C@@]2(O)C(O)=C3C(=O)c4c(O)ccc(-c5ccc(F)c(C=O)c5)c4C[C@H]3C[C@@H]12] | NT | NT | NT |

| ID | STRUCTURE | S. aureus | E. hirae | E. coli |
|---|---|---|---|---|
| GO | 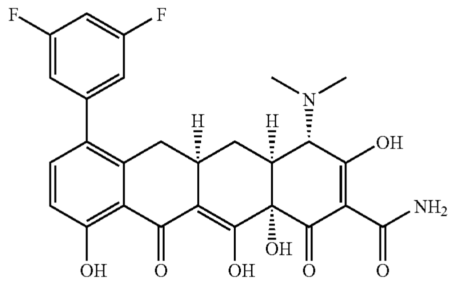 [SMILES: CN(C)[C@@H]1C(O)=C(C(N)=O)C(=O)[C@@]2(O)C(O)=C3C(=O)c4c(O)ccc(-c5cc(F)cc(F)c5)c4C[C@H]3C[C@@H]12] | NT | NT | NT |
| GP | 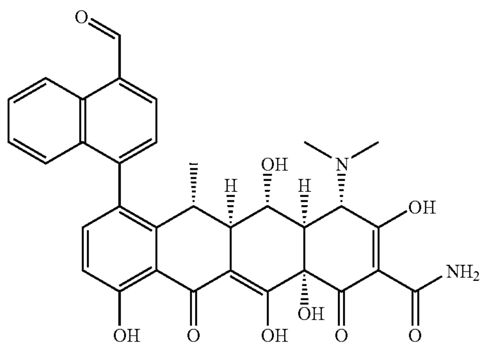 [SMILES: C[C@H]1c2c(-c3ccc(C=O)c4ccccc34)ccc(O)c2C(=O)C2=C(O)[C@]3(O)C(=O)C(C(N)=O)=C(O)[C@@H](N(C)C)[C@@H]3[C@@H](O)[C@@H]21] | NT | NT | NT |
| GQ | 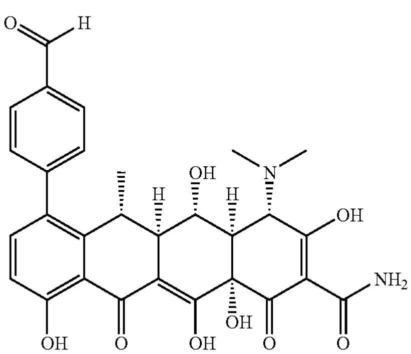 [SMILES: C[C@H]1c2c(-c3ccc(C=O)cc3)ccc(O)c2C(=O)C2=C(O)[C@]3(O)C(=O)C(C(N)=O)=C(O)[C@@H](N(C)C)[C@@H]3[C@@H](O)[C@@H]21] | NT | NT | NT |
| GR | 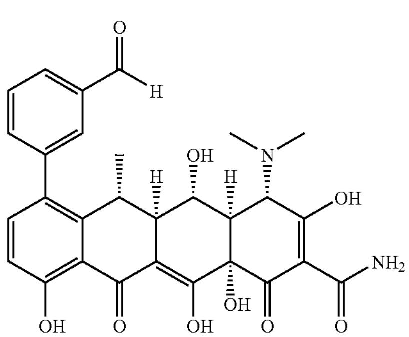 [SMILES: C[C@H]1c2c(-c3cccc(C=O)c3)ccc(O)c2C(=O)C2=C(O)[C@]3(O)C(=O)C(C(N)=O)=C(O)[C@@H](N(C)C)[C@@H]3[C@@H](O)[C@@H]21] | NT | NT | NT |

| ID | STRUCTURE | S. aureus | E. hirae | E. coli |
|---|---|---|---|---|
| GS | 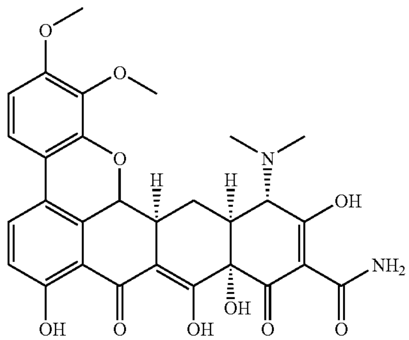 [SMILES: COc1ccc2c(c1OC)OC1c3c-2ccc(O)c3C(=O)C2=C(O)[C@]3(O)C(=O)C(C(N)=O)=C(O)[C@@H](N(C)C)[C@@H]3C[C@@H]21] | NT | NT | NT |
| GT | 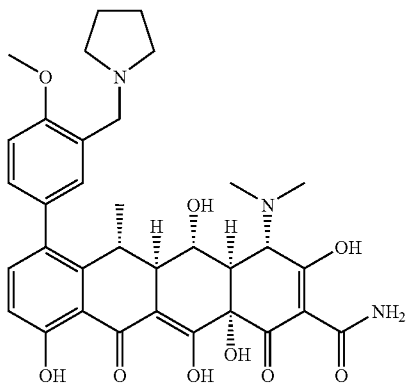 [SMILES: COc1ccc(-c2ccc(O)c3c2[C@H](C)[C@@H]2C(=C(O)[C@]4(O)C(=O)C(C(N)=O)=C(O)[C@@H](N(C)C)[C@@H]4[C@H]2O)C3=O)cc1CN1CCCC1] | NT | NT | NT |
| GU | 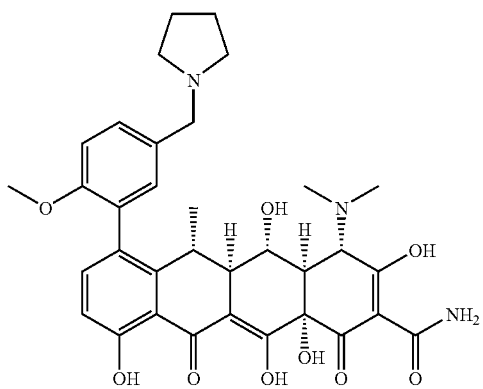 [SMILES: COc1ccc(CN2CCCC2)cc1-c1ccc(O)c2c1[C@H](C)[C@@H]1C(=C(O)[C@]3(O)C(=O)C(C(N)=O)=C(O)[C@@H](N(C)C)[C@@H]3[C@H]1O)C2=O] | NT | NT | NT |
| GV | 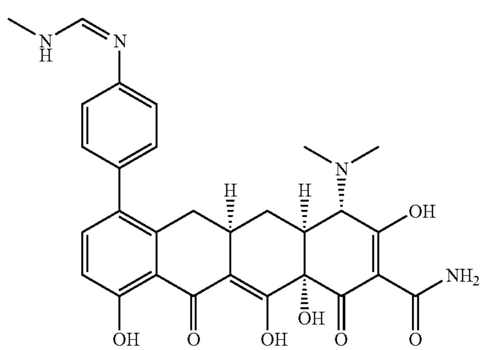 [SMILES: CN/C=N\c1ccc(-c2ccc(O)c3c2C[C@H]2C[C@H]4[C@H](N(C)C)C(O)=C(C(N)=O)C(=O)[C@@]4(O)C(O)=C2C3=O)cc1] | NT | NT | NT |

-continued
| ID | STRUCTURE | S. aureus | E. hirae | E. coli |
|---|---|---|---|---|
| GW | 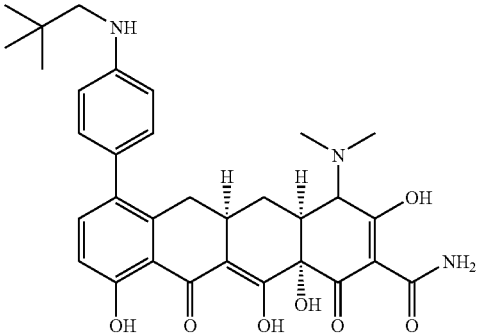 [SMILES: CN(C)C1C(O)=C(C(N)=O)C(=O)[C@@]2(O)C(O)=C3C(=O)c4c(O)ccc(-c5ccc(NCC(C)(C)C)cc5)c4C[C@H]3C[C@@H]12] | NT | NT | NT |
| GX | 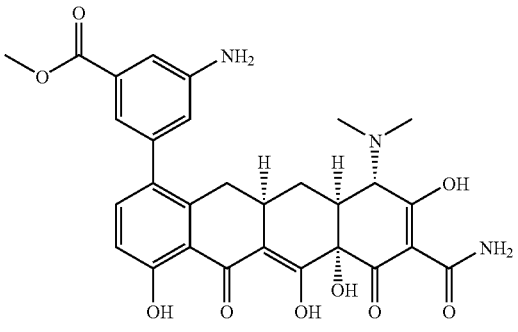 [SMILES: COC(=O)c1cc(N)cc(-c2ccc(O)c3c2C[C@H]2C[C@H]4[C@H](N(C)C)C(O)=C(C(N)=O)C(=O)[C@@]4(O)C(O)=C2C3=O)c1] | NT | NT | NT |
| GY | 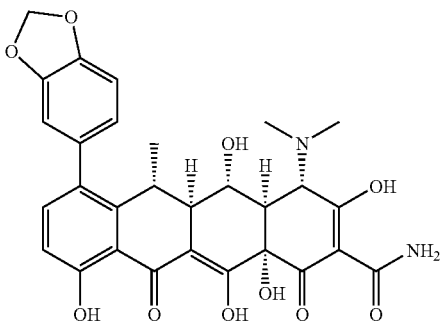 [SMILES: C[C@H]1c2c(-c3ccc4c(c3)OCO4)ccc(O)c2C(=O)C2=C(O)[C@]3(O)C(=O)C(C(N)=O)=C(O)[C@@H](N(C)C)[C@@H]3[C@@H](O)[C@@H]21] | NT | NT | NT |
| GZ | 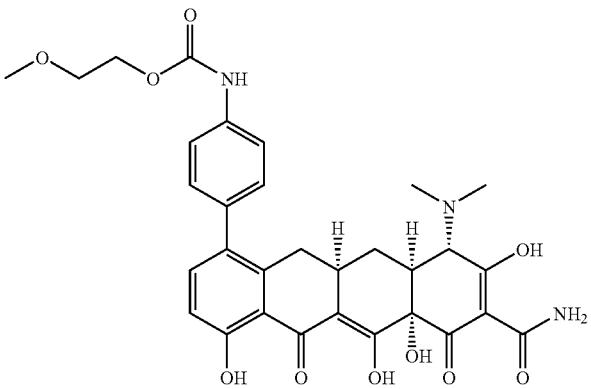 [SMILES: COCCOC(=O)Nc1ccc(-c2ccc(O)c3c2C[C@H]2C[C@H]4[C@H](N(C)C)C(O)=C(C(N)=O)C(=O)[C@@]4(O)C(O)=C2C3=O)cc1] | NT | NT | NT |

-continued

| ID | STRUCTURE | S. aureus | E. hirae | E. coli |
|---|---|---|---|---|
| HA | 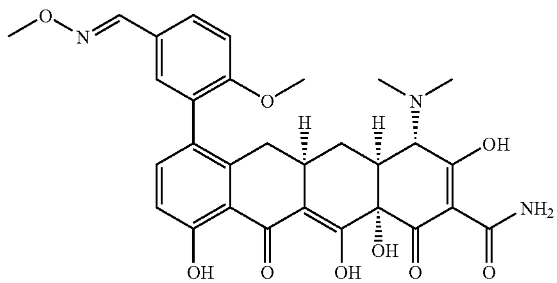 [SMILES: CO/N=C/c1ccc(OC)c(-c2ccc(O)c3c2C[C@H]2C[C@H]4[C@H](N(C)C)C(O)=C(C(N)=O)C(=O)[C@@]4(O)C(O)=C2C3=O)c1] | NT | NT | NT |
| HB | 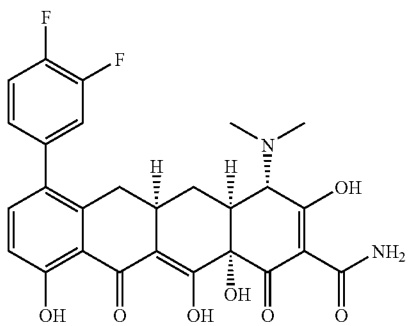 | NT | NT | NT |
| HC | 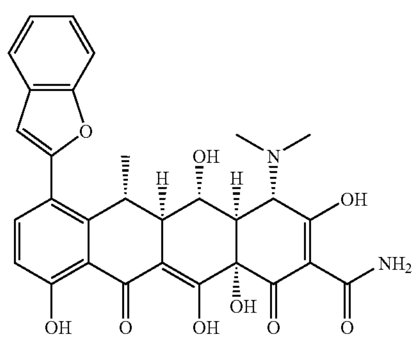 [SMILES: C[C@H]1c2c(-c3cc4ccccc4o3)ccc(O)c2C(=O)C2=C(O)[C@]3(O)C(=O)C(C(N)=O)=C(O)[C@@H](N(C)C)[C@@H]3[C@@H](O)[C@@H]21] | NT | NT | NT |
| HD | 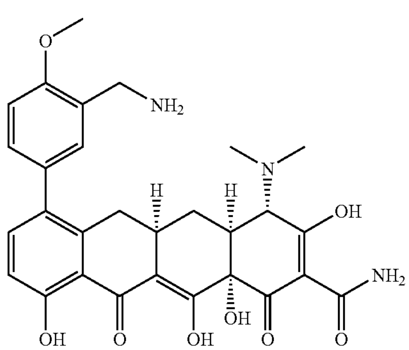 [SMILES: COc1ccc(-c2ccc(O)c3c2C[C@H]2C[C@H]4[C@H](N(C)C)C(O)=C(C(N)=O)C(=O)[C@@]4(O)C(O)=C2C3=O)cc1CN] | NT | NT | NT |

| ID | STRUCTURE | S. aureus | E. hirae | E. coli |
|---|---|---|---|---|
| HE | 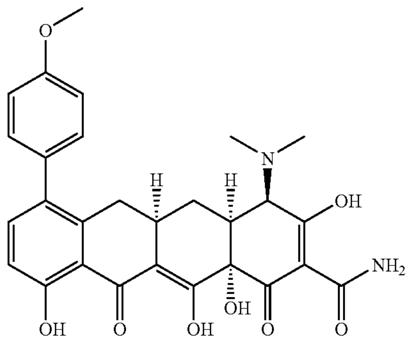 | NT | NT | NT |
| HF | 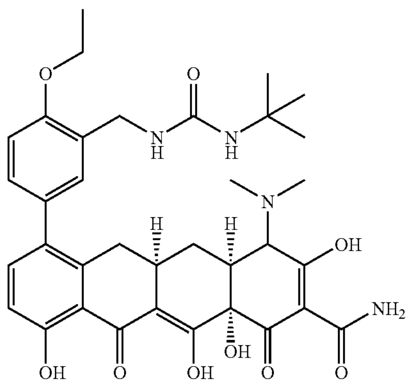 [SMILES: CCOc1ccc(-c2ccc(O)c3c2C[C@H]2C[C@H]4C(N(C)C)C(O)=C(C(N)=O)C(=O)[C@@]4(O)C(O)=C2C3=O)cc1CNC(=O)NC(C)(C)C] | NT | NT | NT |
| HG | 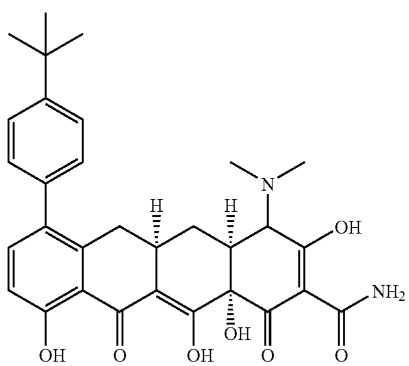 [SMILES: CN(C)C1C(O)=C(C(N)=O)C(=O)[C@@]2(O)C(O)=C3C(=O)c4c(O)ccc(-c5ccc(C(C)(C)C)cc5)c4C[C@H]3C[C@@H]12] | NT | NT | NT |
| HH | 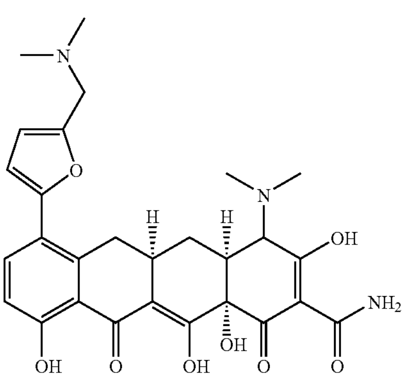 [SMILES: CN(C)Cc1ccc(-c2ccc(O)c3c2C[C@H]2C[C@H]4C(N(C)C)C(O)=C(C(N)=O)C(=O)[C@@]4(O)C(O)=C2C3=O)o1] | NT | NT | NT |

| ID | STRUCTURE | S. aureus | E. hirae | E. coli |
|---|---|---|---|---|
| HI | 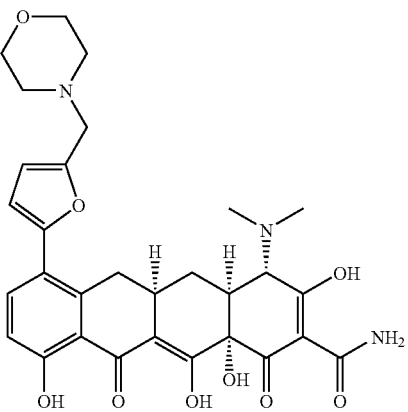 [SMILES: CN(C)[C@@H]1C(O)=C(C(N)=O)C(=O)[C@@]2(O)C(O)=C3C(=O)c4c(O)ccc(-c5ccc(CN6CCOCC6)o5)c4C[C@H]3C[C@@H]12] | NT | NT | NT |
| HJ | 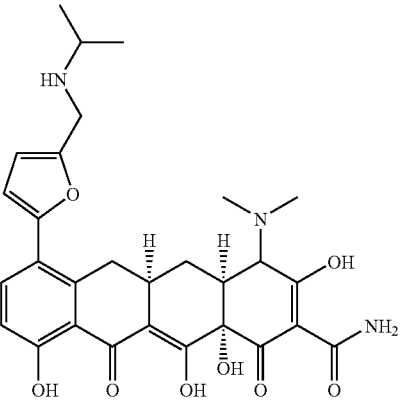 [SMILES: CC(C)NCc1ccc(-c2ccc(O)c3c2C[C@H]2C[C@H]4C(N(C)C)C(O)=C(C(N)=O)C(=O)[C@@]4(O)C(O)=C2C3=O)o1] | NT | NT | NT |
| HK | 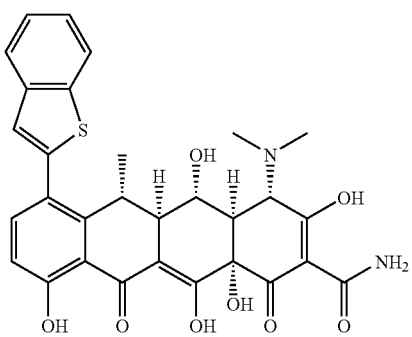 [SMILES: C[C@H]1c2c(-c3cc4ccccc4s3)ccc(O)c2C(=O)C2=C(O)[C@]3(O)C(=O)C(C(N)=O)=C(O)[C@@H](N(C)C)[C@@H]3[C@@H](O)[C@@H]21] | NT | NT | NT |

-continued
| ID | STRUCTURE | S. aureus | E. hirae | E. coli |
|---|---|---|---|---|
| HL | 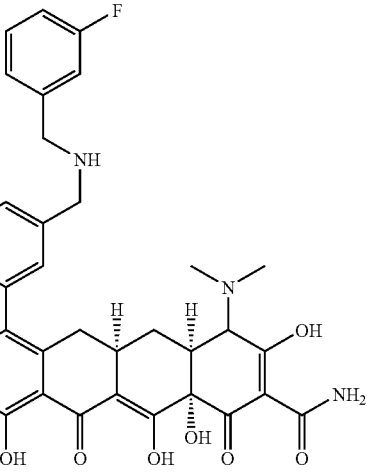 | NT | NT | NT |
| HM | 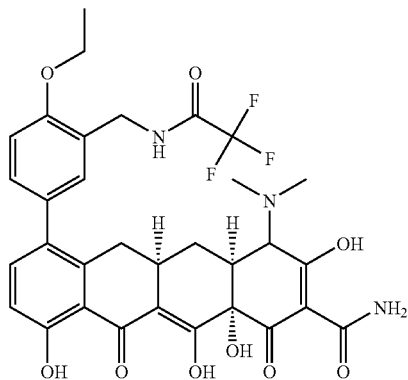 [SMILES: CCOc1ccc(-c2ccc(O)c3c2C[C@H]2C[C@H]4C(N(C)C)C(O)=C(C(N)=O)C(=O)[C@@]4(O)C(O)=C2C3=O)cc1CNC(=O)C(F)(F)F] | NT | NT | NT |
| HN | 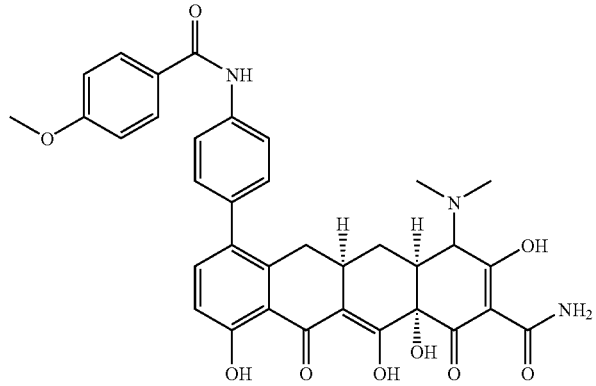 [SMILES: COc1ccc(C(=O)Nc2ccc(-c3ccc(O)c4c3C[C@H]3C[C@H]5C(N(C)C)C(O)=C(C(N)=O)C(=O)[C@@]5(O)C(O)=C3C4=O)cc2)cc1] | NT | NT | NT |
| HO | 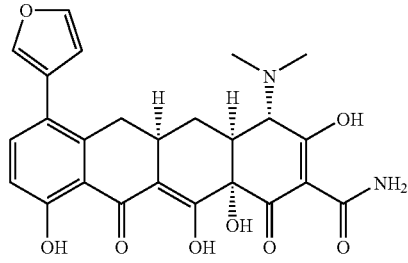 [SMILES: CN(C)[C@@H]1C(O)=C(C(N)=O)C(=O)[C@@]2(O)C(O)=C3C(=O)c4c(O)ccc(-c5ccoc5)c4C[C@H]3C[C@@H]12] | NT | NT | NT |

| ID | STRUCTURE | S. aureus | E. hirae | E. coli |
|---|---|---|---|---|
| HP | 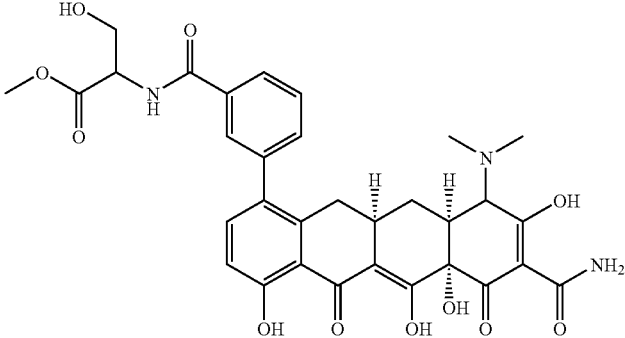 [SMILES: COC(=O)C(CO)NC(=O)c1cccc(-c2ccc(O)c3c2C[C@H]2C[C@H]4C(N(C)C)C(O)=C(C(N)=O)C(=O)[C@@]4(O)C(O)=C2C3=O)c1] | NT | NT | NT |
| HQ | 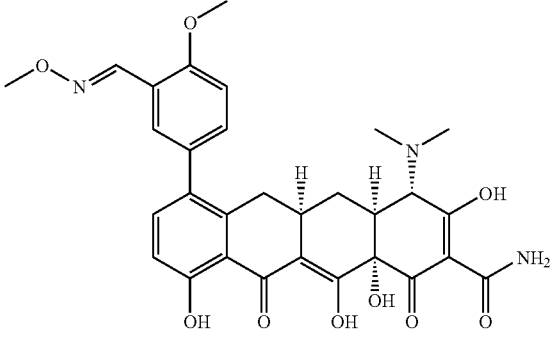 [SMILES: CO/N=C/c1cc(-c2ccc(O)c3c2C[C@H]2C[C@H]4[C@H](N(C)C)C(O)=C(C(N)=O)C(=O)[C@@]4(O)C(O)=C2C3=O)ccc1OC] | NT | NT | NT |
| HR | 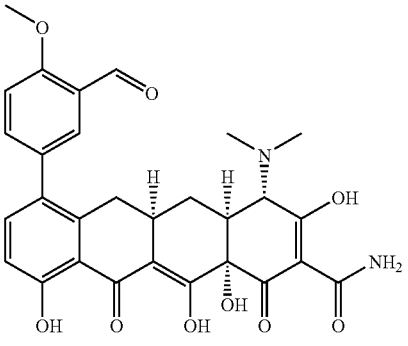 [SMILES: COc1ccc(-c2ccc(O)c3c2C[C@H]2C[C@H]4[C@H](N(C)C)C(O)=C(C(N)=O)C(=O)[C@@]4(O)C(O)=C2C3=O)cc1C=O] | NT | NT | NT |
| HS | 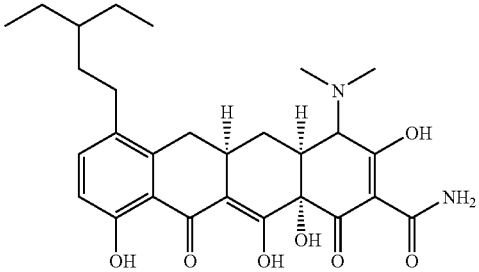 | NT | NT | NT |

| ID | STRUCTURE | S. aureus | E. hirae | E. coli |
|---|---|---|---|---|
| HT | 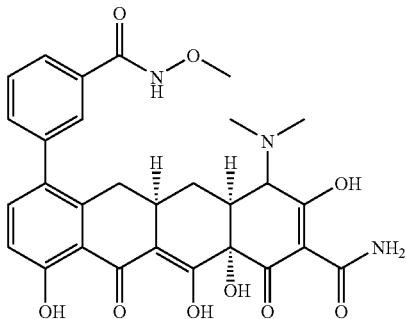 | NT | NT | NT |
| HU | 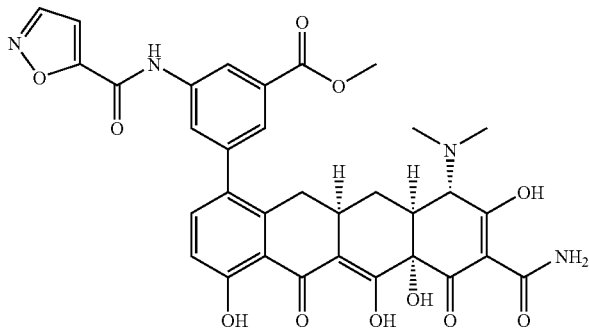 [SMILES: COC(=O)c1cc(NC(=O)c2ccno2)cc(-c2ccc(O)c3c2C[C@H]2C[C@H]4[C@H](N(C)C)C(O)=C(C(N)=O)C(=O)[C@@]4(O)C(O)=C2C3=O)c1] | NT | NT | NT |
| HV | 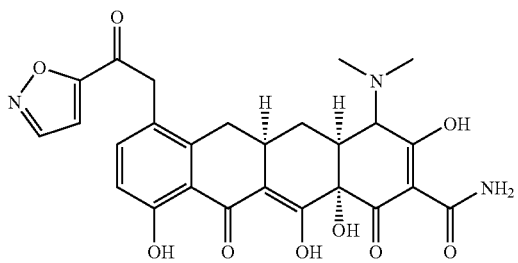 [SMILES: CN(C)C1C(O)=C(C(N)=O)C(=O)[C@@]2(O)C(O)=C3C(=O)c4c(O)ccc(CC(=O)c5ccno5)c4C[C@H]3C[C@@H]12] | NT | NT | NT |
| HW | 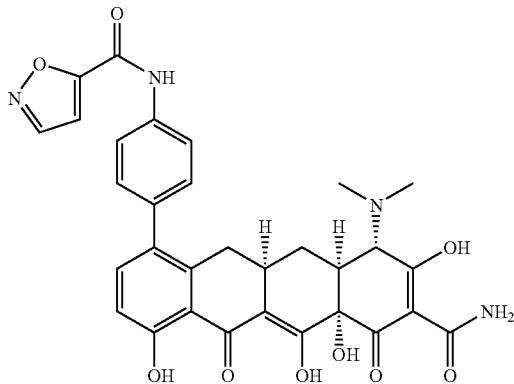 [SMILES: CN(C)[C@@H]1C(O)=C(C(N)=O)C(=O)[C@@]2(O)C(O)=C3C(=O)c4c(O)ccc(-c5ccc(NC(=O)c6ccno6)cc5)c4C[C@H]3C[C@@H]12] | NT | NT | NT |

| ID | STRUCTURE | S. aureus | E. hirae | E. coli |
|---|---|---|---|---|
| HX | 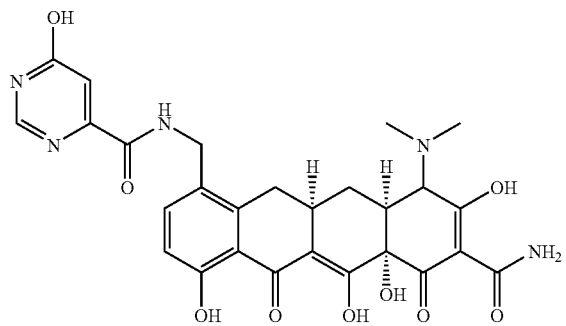 [SMILES: CN(C)C1C(O)=C(C(N)=O)C(=O)[C@@]2(O)C(O)=C3C(=O)c4c(O)ccc(CNC(=O)c5cc(O)ncn5)c4C[C@H]3C[C@@H]12] | NT | NT | NT |
| HY | 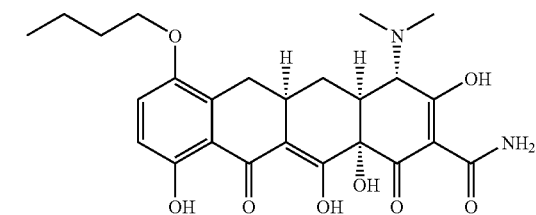 [SMILES: CCCCOc1ccc(O)c2c1C[C@H]1C[C@H]3[C@H](N(C)C)C(O)=C(C(N)=O)C(=O)[C@@]3(O)C(O)=C1C2=O] | NT | NT | NT |
| HZ | 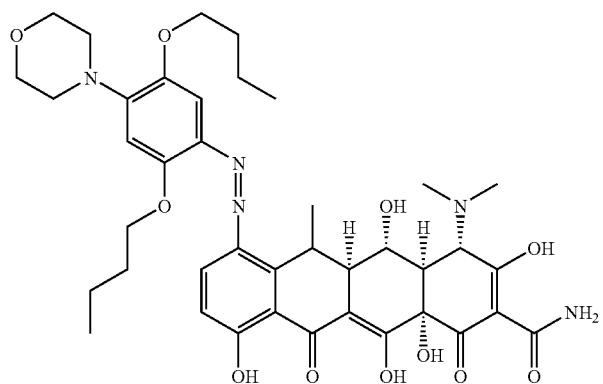 [SMILES: CCCCOc1cc(N2CCOCC2)c(OCCCC)cc1N=Nc1ccc(O)c2c1C(C)[C@@H]1C(=C(O)[C@]3(O)C(=O)C(C(N)=O)=C(O)[C@@H](N(C)C)[C@@H]3[C@H]1O)C2=O] | NT | NT | NT |
| IA | 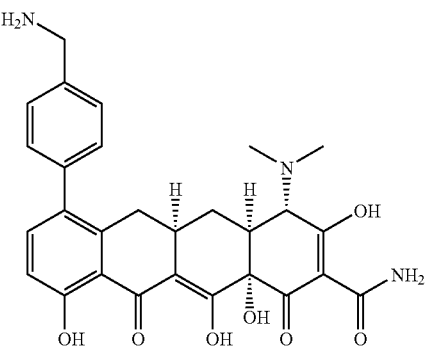 [SMILES: CN(C)[C@@H]1C(O)=C(C(N)=O)C(=O)[C@@]2(O)C(O)=C3C(=O)c4c(O)ccc(-c5ccc(CN)cc5)c4C[C@H]3C[C@@H]12] | NT | NT | NT |

-continued

| ID | STRUCTURE | S. aureus | E. hirae | E. coli |
|---|---|---|---|---|
| IB | 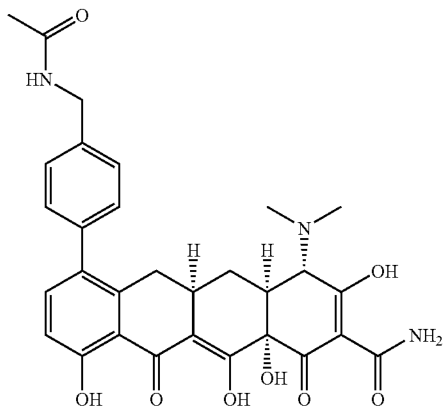 [SMILES: CC(=O)NCc1ccc(-c2ccc(O)c3c2C[C@H]2C[C@H]4[C@H](N(C)C)C(O)=C(C(N)=O)C(=O)[C@@]4(O)C(O)=C2C3=O)cc1] | NT | NT | NT |
| IC | 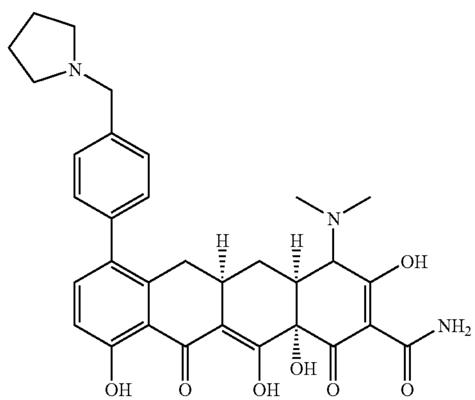 [SMILES: CN(C)C1C(O)=C(C(N)=O)C(=O)[C@@]2(O)C(O)=C3C(=O)c4c(O)ccc(-c5ccc(CN6CCCC6)cc5)c4C[C@H]3C[C@@H]12] | NT | NT | NT |
| ID | 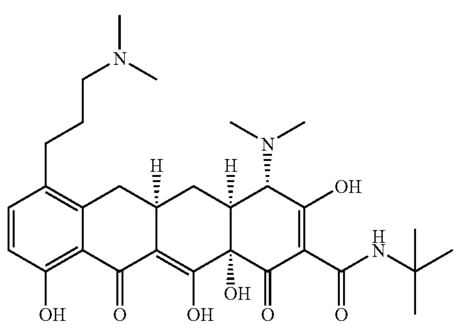 [SMILES: CN(C)CCCc1ccc(O)c2c1C[C@H]1C[C@H]3[C@H](N(C)C)C(O)=C(C(=O)NC(C)(C)C)C(=O)[C@@]3(O)C(O)=C1C2=O] | NT | NT | NT |
| IE | 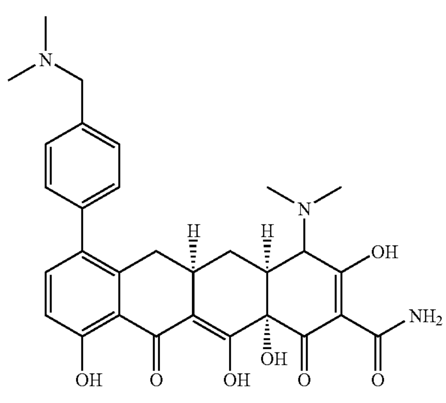 [SMILES: CN(C)Cc1ccc(-c2ccc(O)c3c2C[C@H]2C[C@H]4C(N(C)C)C(O)=C(C(N)=O)C(=O)[C@@]4(O)C(O)=C2C3=O)cc1] | NT | NT | NT |

-continued

| ID | STRUCTURE | S. aureus | E. hirae | E. coli |
|----|-----------|-----------|----------|---------|
| IF | 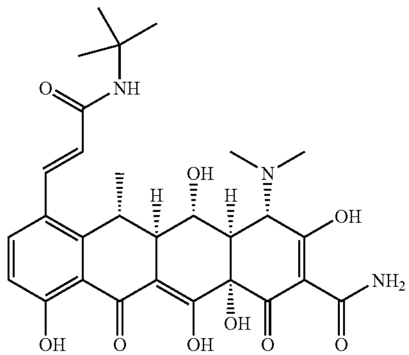 [SMILES: C[C@H]1c2c(/C=C/C(=O)NC(C)(C)C)ccc(O)c2C(=O)C2=C(O)[C@]3(O)C(=O)C(C(N)=O)=C(O)[C@@H](N(C)C)[C@@H]3[C@@H](O)[C@@H]21] | NT | NT | NT |
| IG | 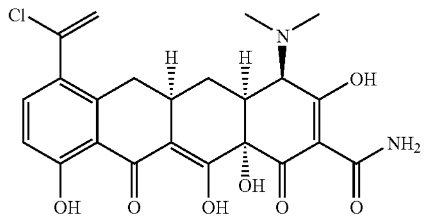 [SMILES: C=C(Cl)c1ccc(O)c2c1C[C@H]1C[C@H]3[C@@H](N(C)C)C(O)=C(C(N)=O)C(=O)[C@@]3(O)C(O)=C1C2=O] | NT | NT | NT |
| IH | 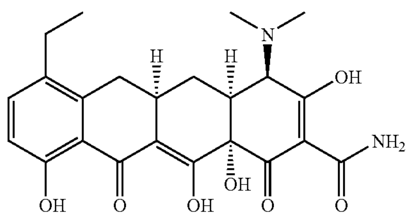 [SMILES: CCc1ccc(O)c2c1C[C@H]1C[C@H]3[C@@H](N(C)C)C(O)=C(C(N)=O)C(=O)[C@@]3(O)C(O)=C1C2=O] | NT | NT | NT |
| II | 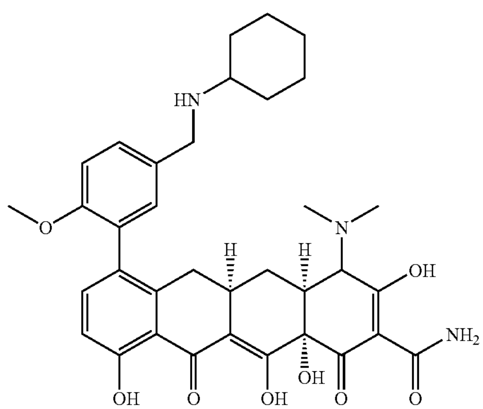 [SMILES: COc1ccc(CNC2CCCCC2)cc1-c1ccc(O)c2c1C[C@H]1C[C@H]3C(N(C)C)C(O)=C(C(N)=O)C(=O)[C@@]3(O)C(O)=C1C2=O] | NT | NT | NT |
| IJ | 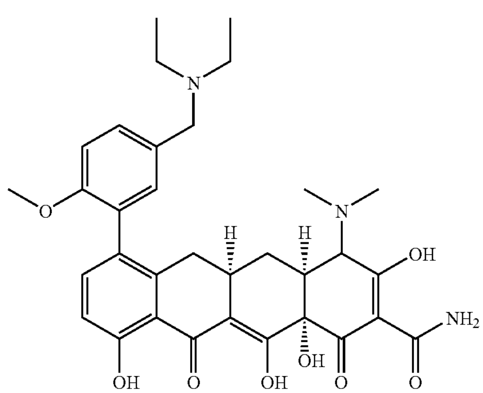 [SMILES: CCN(CC)Cc1ccc(OC)c(-c2ccc(O)c3c2C[C@H]2C[C@H]4C(N(C)C)C(O)=C(C(N)=O)C(=O)[C@@]4(O)C(O)=C2C3=O)c1] | NT | NT | NT |

| ID | STRUCTURE | S. aureus | E. hirae | E. coli |
|---|---|---|---|---|
| IK | 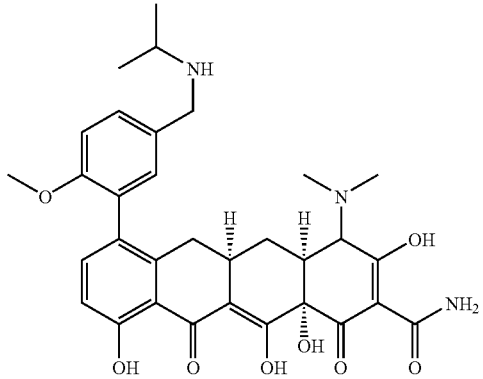 [SMILES: COc1ccc(CNC(C)C)cc1-c1ccc(O)c2c1C[C@H]1C[C@H]3C(N(C)C)C(O)=C(C(N)=O)C(=O)[C@@]3(O)C(O)=C1C2=O] | NT | NT | NT |
| IL | 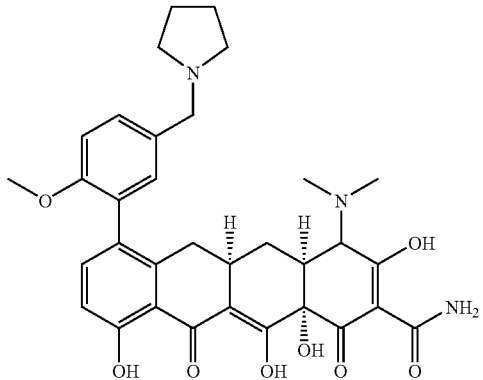 [SMILES: COc1ccc(CN2CCCC2)cc1-c1ccc(O)c2c1C[C@H]1C[C@H]3C(N(C)C)C(O)=C(C(N)=O)C(=O)[C@@]3(O)C(O)=C1C2=O] | NT | NT | NT |
| IM | 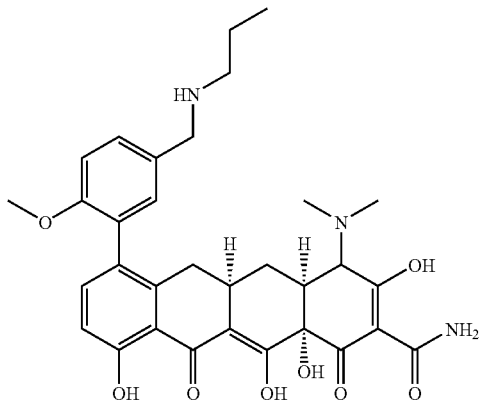 [SMILES: CCCNCc1ccc(OC)c(-c2ccc(O)c3c2C[C@H]2C[C@H]4C(N(C)C)C(O)=C(C(N)=O)C(=O)[C@@]4(O)C(O)=C2C3=O)c1] | NT | NT | NT |
| IN | 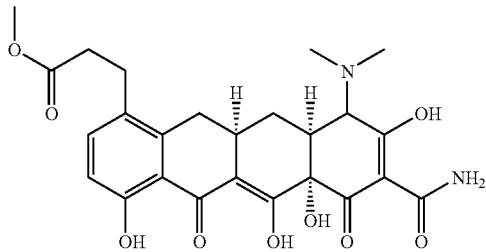 [SMILES: COC(=O)CCc1ccc(O)c2c1C[C@H]1C[C@H]3C(N(C)C)C(O)=C(C(N)=O)C(=O)[C@@]3(O)C(O)=C1C2=O] | NT | NT | NT |

| ID | STRUCTURE | S. aureus | E. hirae | E. coli |
|---|---|---|---|---|
| IO | 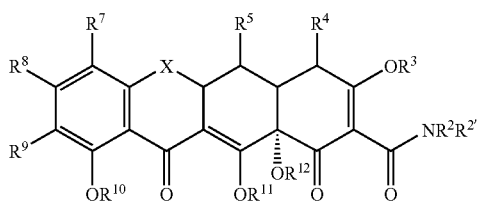 | NT | NT | NT |

The invention claimed is:
1. A substituted tetracycline compound of Formula I:

(I)

wherein:
X is CHC(R$^{13}$Y'Y), CR$^{6'}$R$^6$, C=CR$^{6'}$R$^6$, S, NR$^6$ or O;
R$^2$, R$^{2'}$, R$^{4'}$ and R$^{4''}$ are each independently hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;
R$^4$ is NR$^{4'}$R$^{4''}$, alkyl, alkenyl, alkynyl, hydroxyl, halogen or hydrogen;
R$^3$, R$^{10}$, R$^{11}$ and R$^{12}$ are each independently hydrogen or a pro-drug moiety;
R$^5$ is hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy or aryl carbonyloxy;
R$^6$ and R$^{6'}$ are each independently hydrogen, hydroxyl, halogen, thiol, alkyl, alkenyl, alkynyl, aryl, alkoxy, alkylthio, alkylsulfinyl, alkylsulfonyl, alkylamino or arylalkyl;
R$^7$ is substituted alkyl, substituted alkynyl or substituted amino,
  wherein said substituted alkyl is substituted with one or more groups selected from hydroxyl, heteroaryl, substituted phenyl, carbonyl and silyl,
  wherein said substituted alkynyl is substituted with one or more groups selected from hydroxyl, carbonyl, cycloalkyl and cycloalkenyl, and
  wherein said substituted amino is substituted with one or two groups selected from alkenyl, alkylnyl and aryl;
R$^9$ is hydrogen;
R$^8$ is hydrogen, hydroxyl, halogen, thiol, alkyl, alkenyl, alkynyl, aryl, alkoxy, alkylthio, alkylsulfinyl, alkylsulfonyl, alkylamino or arylalkyl;

R$^{13}$ is hydrogen, hydroxyl, alkyl, alkenyl, alkynyl, alkoxy, alkylthio, alkylsulfinyl, alkylsulfonyl, alkylamino or arylalkyl; and
Y' and Y are each independently hydrogen, halogen, hydroxyl, cyano, sulfhydryl, amino, amido, alkyl, alkenyl, alkynyl, alkoxy, alkylthio, alkylsulfinyl, alkylsulfonyl, alkylamino or arylalkyl,
or pharmaceutically acceptable salts thereof.

2. The tetracycline compound of claim 1, wherein R$^4$ is NR$^{4'}$R$^{4''}$; X is CR$^{6'}$R$^6$; R$^2$, R$^{2'}$, R$^6$, R$^{6'}$, R$^8$, R$^{10}$, R$^{11}$ and R$^{12}$ are each hydrogen; R$^{4'}$ and R$^{4''}$ are lower alkyl; and R$^5$ is hydroxyl or hydrogen.

3. The tetracycline compound of claim 2, wherein R$^{4'}$ and R$^{4''}$ are each methyl and R$^5$ is hydrogen.

4. The tetracycline compound of claim 1, wherein R$^7$ is alkyl substituted with heteroaryl or substituted phenyl.

5. The tetracycline compound of claim 4, wherein R$^7$ is alkyl substituted with substituted phenyl.

6. The tetracycline compound of claim 5, wherein said phenyl is substituted with one or more groups selected from alkyl, alkenyl, alkynyl, halogen, hydroxyl, alkoxy, arylalkyl, aminoalkyl, carboxylate, alkylcarbonyl, arylcarbonyl, alkenylcarbonyl, arylalkylcarbonyl, alkoxycarbonyl, aminocarbonyl, alkylaminocarbonyl, alkenylaminocarbonyl, alkylthiocarbonyl, thiocarboxylate, alkylcarbonyloxy, arylcarbonyloxy, alkoxycarbonyloxy, aryloxycarbonyloxy, amino, acylamino, alkoxycarbonylamino, amido, cyano, nitro, imino, silyl, alkylthio, arylthio, sulfate, alkylsulfinyl, sulfonato, sulfamoyl, sulfonamido, phosphate, phosphonato, phosphinato, sulfhydryl, azido, heterocyclyl, aryl and heteroaryl.

7. The tetracycline compound of claim 4, wherein R$^7$ is alkyl substituted with heteroaryl.

8. The tetracycline compound of claim 7, wherein said heteroaryl is substituted with one or more groups selected from alkyl, alkenyl, alkynyl, halogen, hydroxyl, alkoxy, arylalkyl, aminoalkyl, carboxylate, alkylcarbonyl, arylcarbonyl, alkenylcarbonyl, arylalkylcarbonyl, alkoxycarbonyl, aminocarbonyl, alkylaminocarbonyl, alkenylaminocarbonyl, alkylthiocarbonyl, thiocarboxylate, alkylcarbonyloxy, arylcarbonyloxy, alkoxycarbonyloxy, aryloxycarbonyloxy, amino, acylamino, alkoxycarbonylamino, amido, cyano, nitro, imino, silyl, alkylthio, arylthio, sulfate, alkylsulfinyl, sulfonato, sulfamoyl, sulfonamido, phosphate, phosphonato, phosphinato, sulfhydryl, azido, heterocyclyl, aryl and heteroaryl.

9. The tetracycline compound of claim 7, wherein said heteroaryl is pyridyl.

10. The tetracycline compound of claim 1, wherein $R^7$ is alkyl substituted with carbonyl, wherein said carbonyl is substituted with alkyl, alkenyl, alkynyl, aryl, arylalkyl, alkoxy or amino.

11. The tetracycline compound of claim 1, wherein $R^7$ is alkynyl substituted with carbonyl, wherein said carbonyl is substituted with alkyl, alkenyl, alkynyl, aryl, arylalkyl, alkoxy or amino.

12. The tetracycline compound of claim 1, wherein $R^7$ is alkynyl substituted with one or more groups selected from cyclopropyl, cyclobutyl, cyclopentyl, cyclohexyl, cycloheptyl, cyclooctyl, cyclopentenyl, cyclohexenyl, cycloheptenyl and cyclooctenyl.

13. The tetracycline compound of claim 1, wherein $R^7$ is amino substituted with one or two aryl.

14. The tetracycline compound of claim 13, wherein said aryl is heteroaryl selected from pyrazolyl, imidazolyl, furanyl, thienyl, oxazolyl, isoxazolyl, thiazolyl, isothiazolyl, pyridyl, pyrimidyl and pyrazinyl.

15. A substituted tetracycline compound selected from:

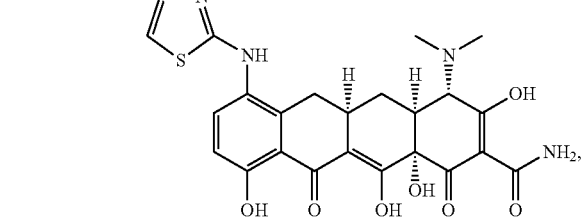

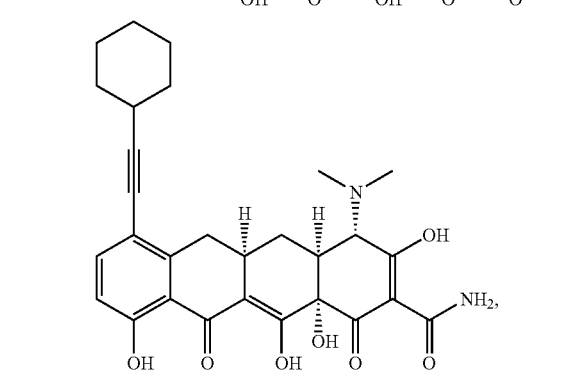

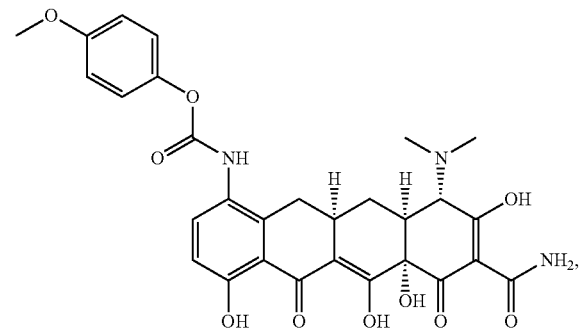

-continued

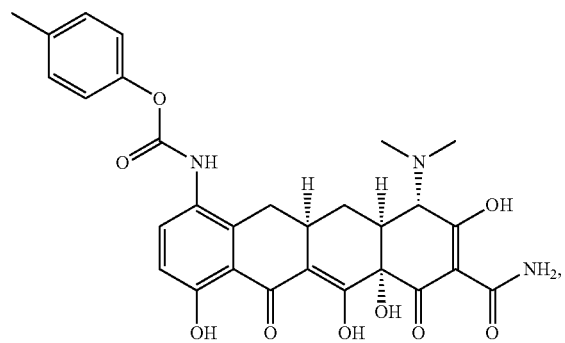

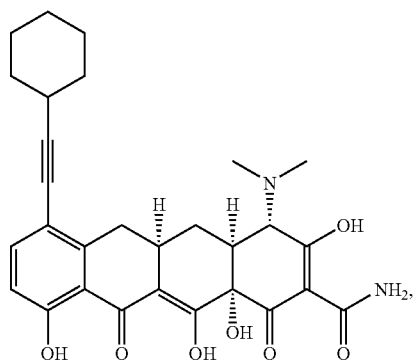

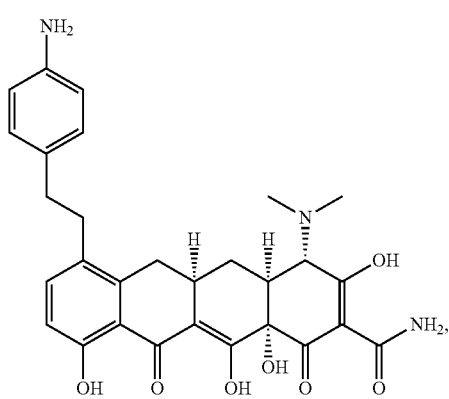

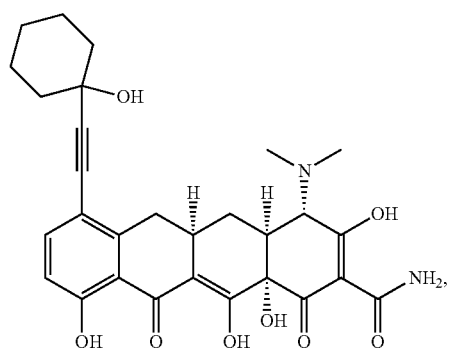

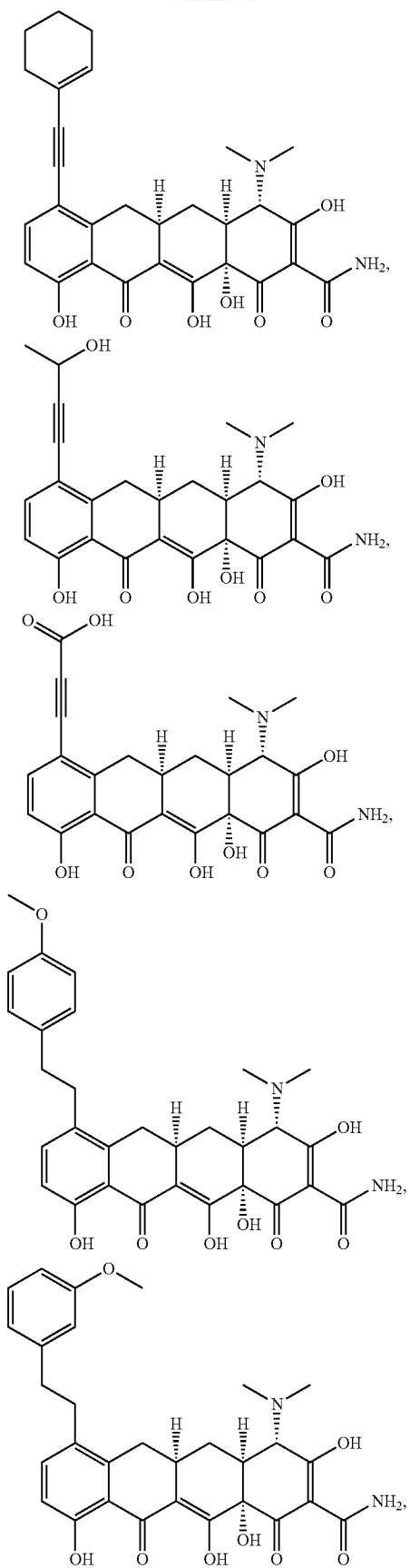
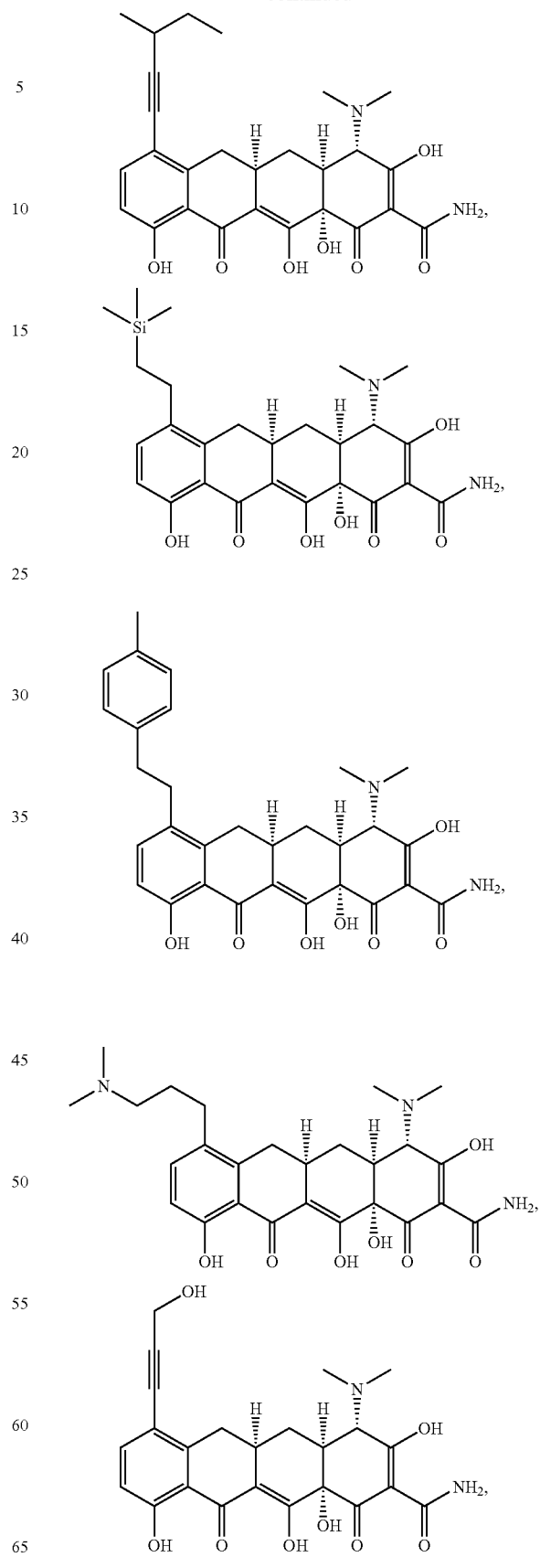

193
-continued
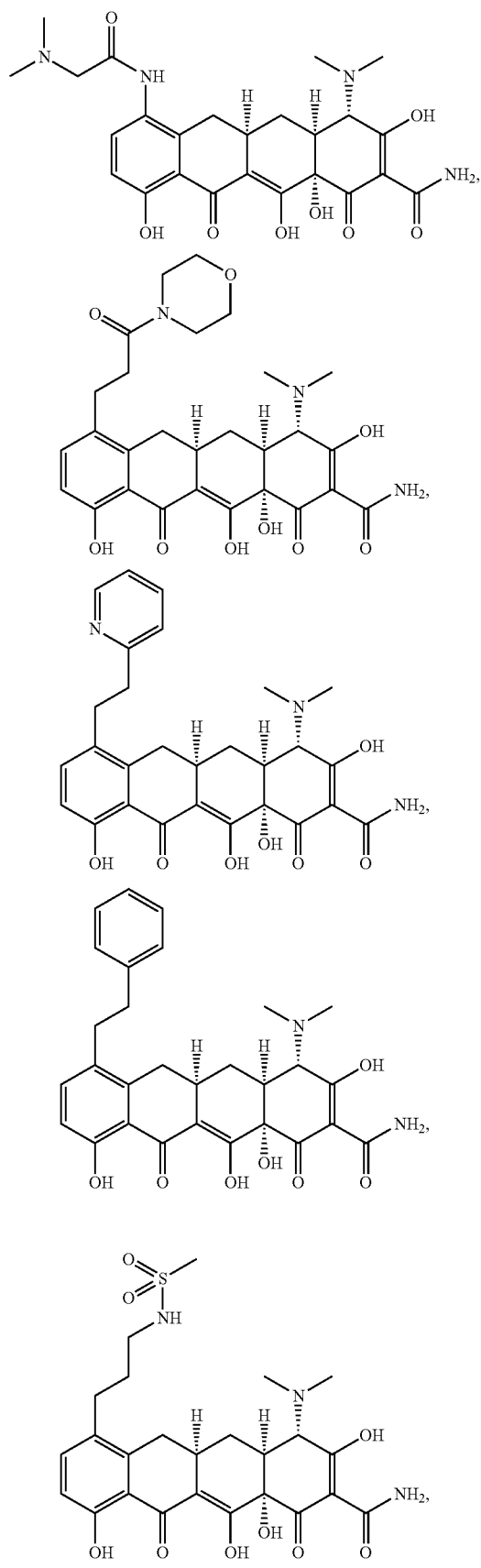
194
-continued
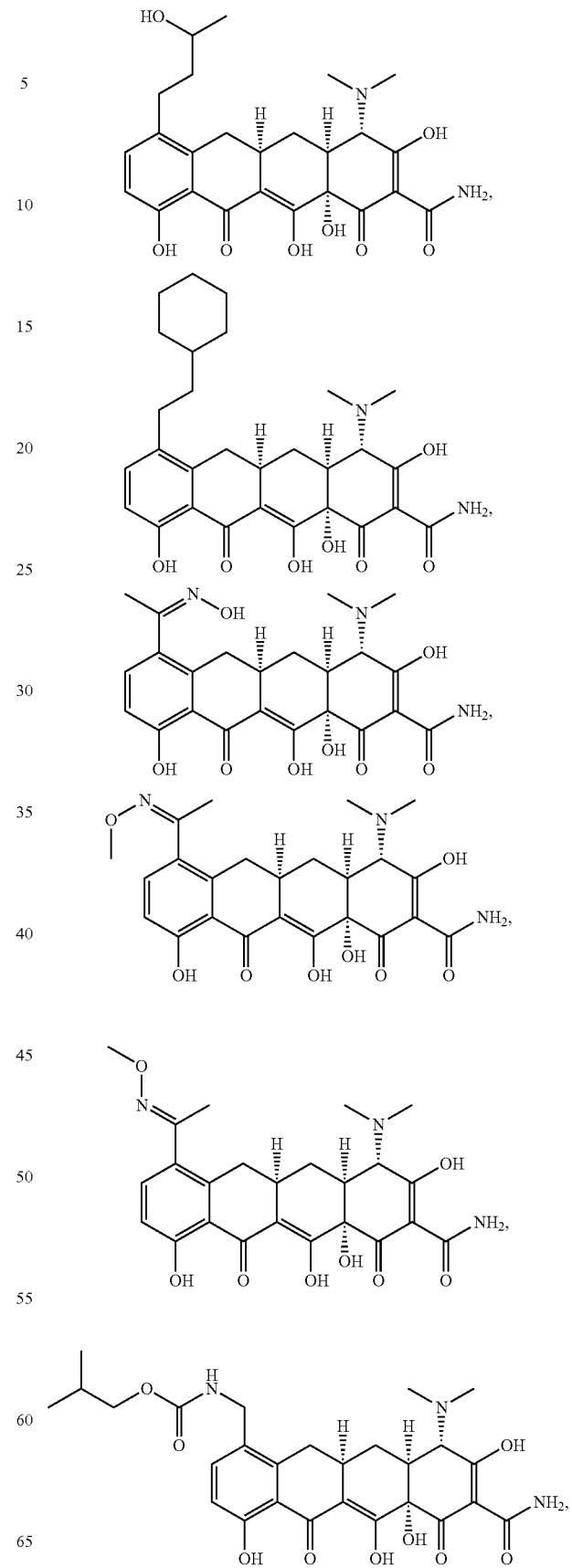

195
-continued
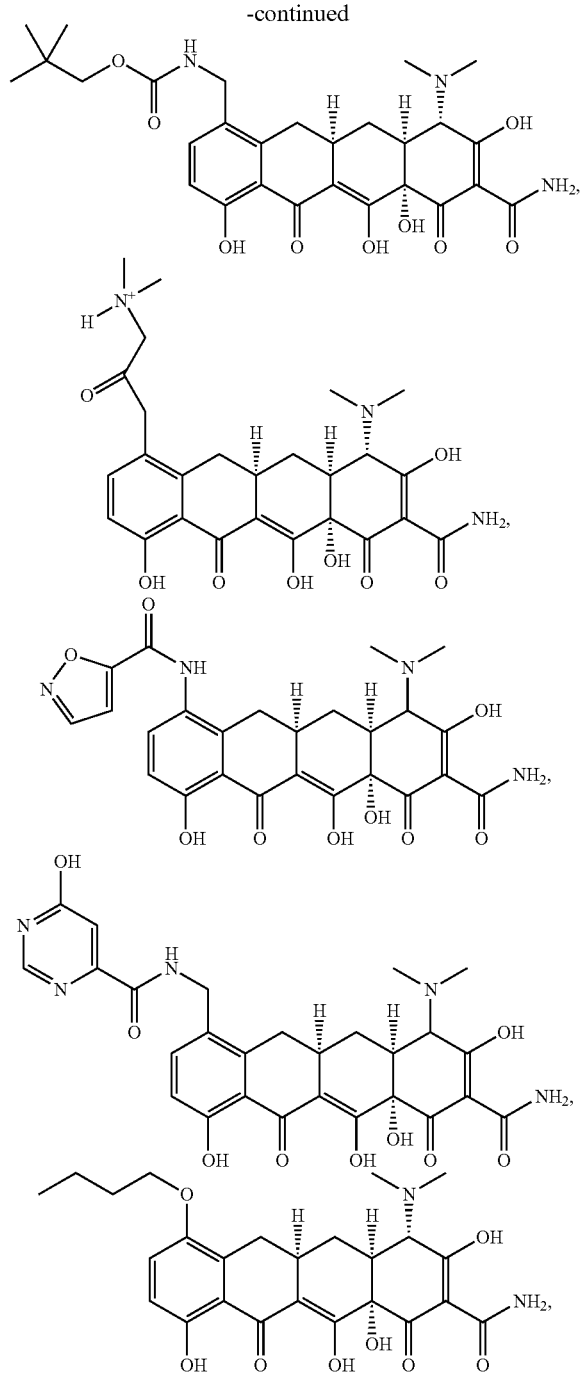
196
-continued
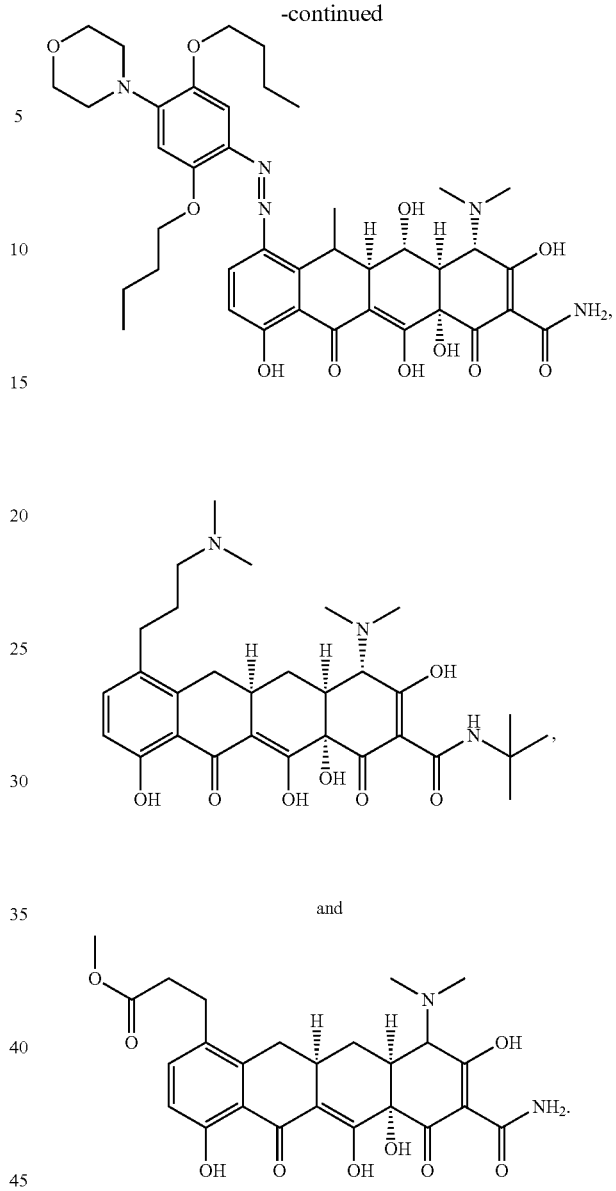
and
16. A pharmaceutical composition comprising a therapeutically effective amount of a tetracycline compound of claim 1 or 15 and a pharmaceutically acceptable carrier.
17. The tetracycline compound of claim 1, wherein $R^7$ is substituted methyl.
* * * * *